United States Patent
Kushida et al.

(10) Patent No.: US 11,935,241 B2
(45) Date of Patent: Mar. 19, 2024

(54) IMAGE PROCESSING APPARATUS, IMAGE PROCESSING METHOD AND COMPUTER-READABLE MEDIUM FOR IMPROVING IMAGE QUALITY

(71) Applicant: CANON KABUSHIKI KAISHA, Tokyo (JP)

(72) Inventors: Akihiro Kushida, Kanagawa (JP); Ritsuya Tomita, Kanagawa (JP)

(73) Assignee: CANON KABUSHIKI KAISHA, Tokyo (JP)

(*) Notice: Subject to any disclaimer, the term of this patent is extended or adjusted under 35 U.S.C. 154(b) by 421 days.

(21) Appl. No.: 17/224,562

(22) Filed: Apr. 7, 2021

(65) Prior Publication Data
US 2021/0224997 A1    Jul. 22, 2021

Related U.S. Application Data

(63) Continuation of application No. PCT/JP2019/039676, filed on Oct. 8, 2019.

(30) Foreign Application Priority Data

Oct. 10, 2018  (JP) ................................ 2018-191449
Oct. 3, 2019   (JP) ................................ 2019-183106

(51) Int. Cl.
*G06T 7/00*    (2017.01)
*A61B 3/00*    (2006.01)
(Continued)

(52) U.S. Cl.
CPC .......... *G06T 7/0014* (2013.01); *A61B 3/0025* (2013.01); *A61B 3/102* (2013.01);
(Continued)

(58) Field of Classification Search
None
See application file for complete search history.

(56) References Cited

U.S. PATENT DOCUMENTS

2017/0014025 A1    1/2017 Uchida
2018/0140257 A1*   5/2018 Govindjee ............. G16H 30/40
(Continued)

FOREIGN PATENT DOCUMENTS

CN    104127168 A    11/2014
JP    H09-179977 A   7/1997
(Continued)

OTHER PUBLICATIONS

International Search Report issued in International Application No. PCT/JP2019/039676 dated Dec. 17, 2019, pp. 1-2, English Translation.

(Continued)

*Primary Examiner* — Tahmina N Ansari
(74) *Attorney, Agent, or Firm* — Carter, DeLuca & Farrell LLP

(57) ABSTRACT

An image processing apparatus is provided that includes: an obtaining unit configured to obtain a first medical image of a subject; and an image quality improving unit configured to generate a second medical image with image quality higher than image quality of different regions including a first region and a second region that is different from the first region in the obtained first image, using the obtained first image as input data that is input into a learned model.

19 Claims, 25 Drawing Sheets

(51) Int. Cl.
    *A61B 3/10* (2006.01)
    *G06T 5/00* (2006.01)
    *G06T 5/50* (2006.01)

(52) U.S. Cl.
    CPC ............... *G06T 5/001* (2013.01); *G06T 5/50* (2013.01); *G06T 2200/04* (2013.01); *G06T 2207/10101* (2013.01); *G06T 2207/20081* (2013.01); *G06T 2207/20084* (2013.01); *G06T 2207/20092* (2013.01); *G06T 2207/30041* (2013.01)

(56) References Cited

U.S. PATENT DOCUMENTS

| 2018/0153395 | A1  | 6/2018 | Goto   |           |
|--------------|-----|--------|--------|-----------|
| 2019/0122360 | A1* | 4/2019 | Zhang  | G06F 18/24|
| 2021/0104313 | A1  | 4/2021 | Mizobe et al. |    |
| 2021/0158525 | A1* | 5/2021 | Iwase  | A61B 3/0025|
| 2021/0183019 | A1* | 6/2021 | Uchida | G06N 3/044|
| 2021/0224997 | A1* | 7/2021 | Kushida| G06T 5/001|

FOREIGN PATENT DOCUMENTS

| JP | 2009-151350 A | 7/2009 |
| JP | 2014-104275 A | 6/2014 |
| JP | 2015129987 A  | 7/2015 |
| JP | 2016195878 A  | 11/2016 |
| JP | 6046250 B2    | 12/2016 |
| JP | 2017-55916 A  | 3/2017 |
| JP | 2018-136537 A | 8/2018 |
| WO | 2018055545 A1 | 3/2018 |

OTHER PUBLICATIONS

International Preliminary Report on Patentability dated Apr. 8, 2021 by the International Bureau of WIPO on behalf of the Japan Patent Office acting as International Searching Authority in International Application No. PCT/JP2019/039676, with English translation.
Notice of Reasons for Refusal issued by the Japan Patent Office dated Jun. 21, 2022 in corresponding JP Patent Application No. 2019-183106, with English translation.
Notice of Reasons for Refusal issued by the Japan Patent Office dated Oct. 25, 2022 in corresponding JP Patent Application No. 2019-183106, with English translation.
Sheet, D. et al., "Deep Learning of Tissue Specific Speckle Representations in Optical Coherence Tomography and Deeper Exploration for In Situ Histology" IEEE International Symposium on Biomedical Imaging (Apr. 2015) pp. 777-780, vol. 4.
Office Action issued by the The National Intellectual Property Administration of the People's Republic of China dated Jan. 9, 2024 in corresponding CN Patent Application No. 201980066849.X, with English translation.

* cited by examiner

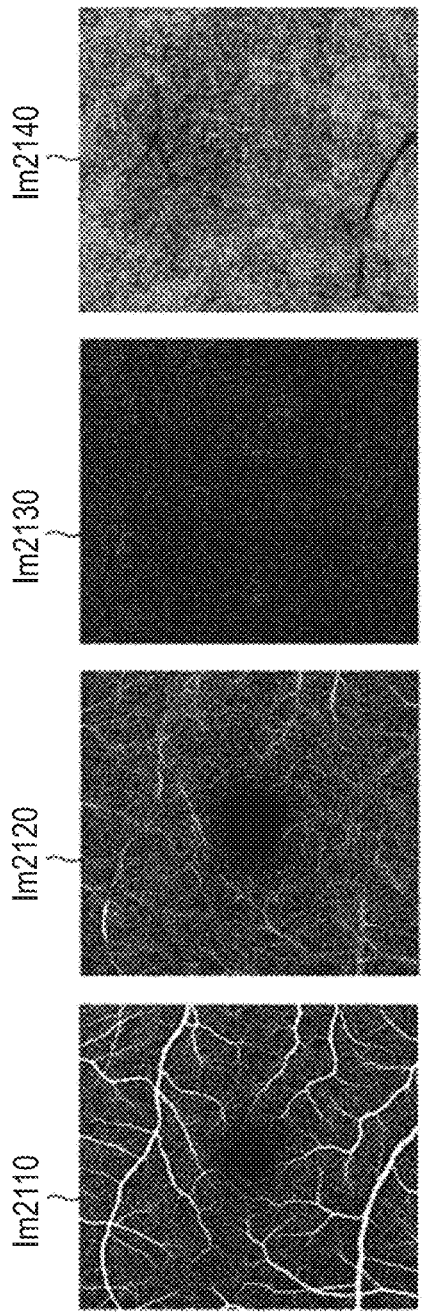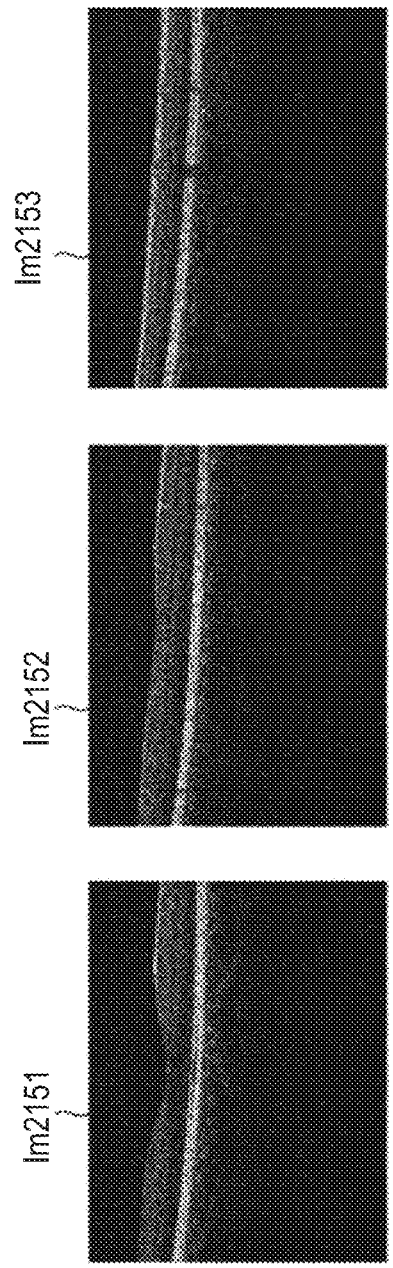
FIG. 21A
FIG. 21B

IMAGE PROCESSING APPARATUS, IMAGE PROCESSING METHOD AND COMPUTER-READABLE MEDIUM FOR IMPROVING IMAGE QUALITY

CROSS-REFERENCE TO RELATED APPLICATIONS

This application is a Continuation of International Patent Application No. PCT/JP2019/039676, filed Oct. 8, 2019, which claims the benefits of Japanese Patent Application No. 2018-191449, filed Oct. 10, 2018, and Japanese Patent Application No. 2019-183106, filed Oct. 3, 2019, all of which are hereby incorporated by reference herein in their entirety.

BACKGROUND OF THE INVENTION

Field of the Invention

The present invention relates to an image processing apparatus, an image processing method and a computer-readable medium.

Description of the Related Art

Various kinds of ophthalmic devices that utilize optical devices are currently in use. For example, various devices such as an anterior ocular segment imaging apparatus, a fundus camera, and a scanning laser ophthalmoscope (SLO) are being used as optical devices for observing the eye.

Among such devices, an optical coherence tomography apparatus (OCT apparatus) which is based on optical coherence tomography (OCT) that utilizes multi-wavelength light wave interference is capable of obtaining a tomographic image of a sample at a high resolution. Therefore, OCT apparatuses are indispensable as ophthalmic devices in outpatient clinics that specialize in retinal care. OCT apparatuses are also being utilized for endoscopes and the like, and not just for ophthalmology. The OCT apparatuses are widely utilized in ophthalmic diagnosis and the like to obtain tomographic images of the retina in the fundus of an eye to be examined, or tomographic images of the anterior ocular segment such as the cornea.

The source data of a tomographic image imaged with an OCT apparatus is generally about 32 bits of floating point data or 10 or more bits of integer data, and is data with a high dynamic range that includes data in a range from very low intensity information to high intensity information. On the other hand, data which can be displayed on a normal display is data of a relatively low dynamic range, for example, 8-bit integer data. Consequently, when such source data with a high dynamic range is converted as it is into data with a low dynamic range for display, the contrast of a retina portion, which is important for diagnosis of a fundus portion, significantly decreases.

Therefore, in a general OCT apparatus, when converting the source data of a tomographic image into data for display, favorable contrast of a retina portion is obtained by discarding a certain amount of low-intensity-side data. In this case, in the displayed tomographic image, the contrast of a region relating to a vitreous body portion or a choroid portion or the like that is displayed as a low-intensity region decreases, and observation of the internal structure of the vitreous body portion or choroid portion becomes difficult.

On the other hand, when the source data of a tomographic image is subjected to gradation conversion to ensure the contrast of a region relating to a vitreous body portion or a choroid portion or the like in order to observe the internal structure of the vitreous body portion or the choroid portion in more detail, the contrast of a region of a high-intensity retina portion decreases, and observation of the retina portion becomes difficult.

In recent years, there is a need to perform not only local observation of an eye to be examined, but also to perform comprehensive observation of an eye to be examined. In regard to such need, in International Publication No. WO 2014/203901 a method is proposed that performs segmentation of a tomographic image, sets a display condition for each partial region that is identified, and performs gradation conversion processing.

In a diseased eye, the shape of the retina becomes irregular due to the disappearance of layers, bleeding, and the occurrence of leucoma or a neovascular site. Therefore, in the conventional method of segmentation processing that determines the result of image feature extraction utilizing the regularity of the shape of the retina and detects boundaries of retinal layers, there has been a limit in that erroneous detection or the like occurs when detection of the boundaries of retinal layers is performed automatically. In such cases, due to erroneous detection or the like in the segmentation processing, there are cases where gradation conversion processing or the like cannot be appropriately performed for each partial region (observation target) in order to perform a comprehensive observation of the eye to be examined.

Therefore, one objective of the present invention is to provide an image processing apparatus, an image processing method and a computer-readable medium having stored thereon a program, which are capable of generating an image that seems to be an image for which image processing appropriate for each region that is an observation target has been performed.

SUMMARY OF THE INVENTION

An image processing apparatus according to one embodiment of the present invention includes: an obtaining unit configured to obtain a first medical image of a subject; and an image quality improving unit configured to generate a second medical image with image quality higher than image quality of different regions including a first region and a second region that is different from the first region in the obtained first image, using the obtained first image as input data that is input into a learned model.

An image processing method according to another embodiment of the present invention includes: obtaining a first medical image of a subject; and generating a second medical image with image quality higher than image quality of different regions including a first region and a second region that is different from the first region in the obtained first image, using the obtained first image as input data that is input into a learned model.

Further features of the present invention will become apparent from the following description of exemplary embodiments with reference to the attached drawings.

BRIEF DESCRIPTION OF THE DRAWINGS

FIG. 21A is a view illustrating an example of a plurality of OCTA en-face images.

FIG. 21B is a view illustrating an example of a plurality of tomographic images.

DESCRIPTION OF THE EMBODIMENTS

Figure 1:
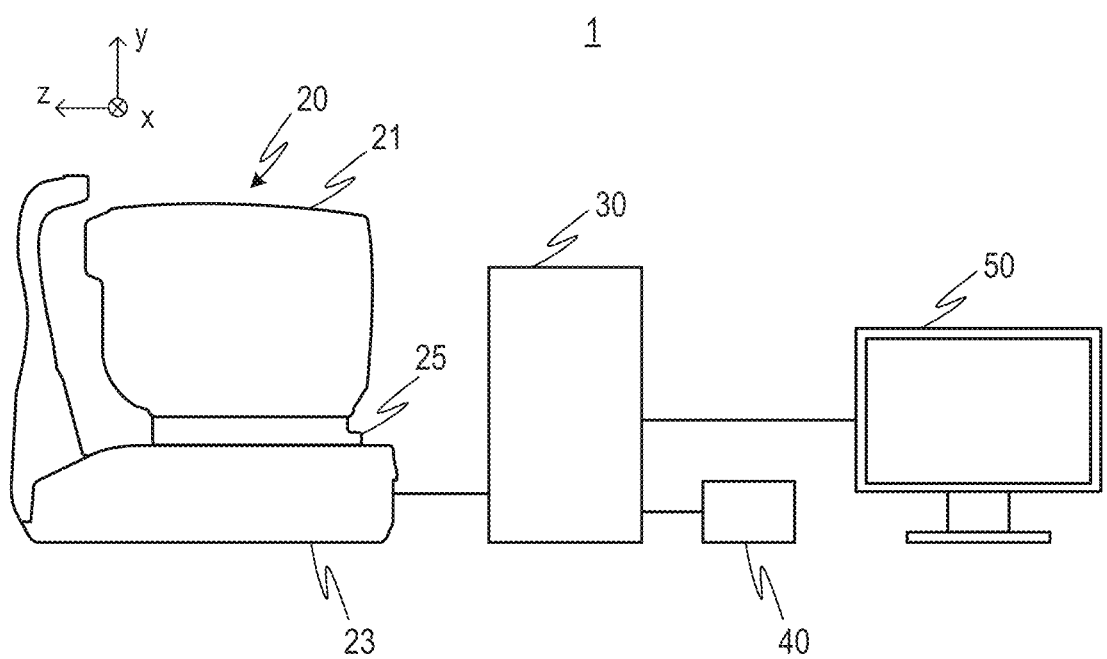
FIG. 1 is a view illustrating a schematic configuration example of an OCT apparatus according to Embodiment 1.

Exemplary embodiments for implementing the present invention will now be described in detail with reference to the accompanying drawings. However, the dimensions, materials, shapes and relative positions of the components described in the following embodiments are not determinate, and can be changed according to a configuration of an apparatus to which the present invention is applied or to various conditions. Further, identical or functionally similar elements are denoted by the same reference numerals in different drawings.

Hereinafter, the term "machine learning model" refers to a learning model that learned according to a machine learning algorithm. Specific examples of algorithms for machine learning include the nearest-neighbor method, the naive Bayes method, the decision tree, and the support vector machine. Further, deep learning (deep structured learning) which utilizes a neural network to generate, by itself, feature values and combining weighting factors for learning may also be mentioned. Algorithms that can be utilized among the aforementioned algorithms can be appropriately used and applied to the embodiments and modifications that are described hereunder. Further, the term "training data" refers to training data that is constituted by pairs of input data and output data. Furthermore, the term "correct answer data" refers to output data of training data.

Note that, the term "learned model" refers to a model which, with respect to a machine learning model that is in accordance with any machine learning algorithm such as deep learning, performed training (learning) using appropriate training data (learning data) in advance. However, although the learned model is a model obtained using appropriate training data in advance, it is assumed that the learned model is not a model that does not perform further learning, and is a model that can also perform incremental learning. Incremental learning can also be performed after the apparatus is installed at the usage destination.

Embodiment 1

An OCT apparatus according to Embodiment 1 will now be described referring to FIG. 1 to FIG. 13C. FIG. 1 is a view illustrating a schematic configuration example of an OCT apparatus according to the present embodiment.

(Main Body Configuration)

An OCT apparatus 1 includes an imaging unit 20, a controlling unit 30 (image processing apparatus), an inputting unit 40, and a display unit 50. A measurement optical system 21, a stage unit 25, and a base unit 23 are provided in the imaging unit 20. The measurement optical system 21 can obtain an anterior ocular segment image, an SLO fundus image of an eye to be examined, and a tomographic image. The measurement optical system 21 is provided on the base unit 23 through the stage unit 25. The stage unit 25 supports the measurement optical system 21 so as to be movable in the front, rear, right, and left directions. A spectrometer and the like that will be described later are provided in the base unit 23.

The controlling unit 30 is connected to the imaging unit 20 and the display unit 50, and can control these units. The controlling unit 30 can generate a tomographic image and perform image processing or the like based on tomographic information obtained from the imaging unit 20 or the like. Note that, the controlling unit 30 may be connected to other arbitrary apparatuses that are not illustrated in the drawings, through any network such as the Internet.

The inputting unit 40 is also connected to the controlling unit 30. The inputting unit 40 is operated by an operator (examiner), and is used for inputting instructions to the controlling unit 30. The inputting unit 40 may include any input device, and for example can include a keyboard and a mouse or the like. The display unit 50 is constituted by any display, and can display information pertaining to the subject and various kinds of images and the like in accordance with control by the controlling unit 30.

(Configuration of Imaging Unit)

Figure 2:
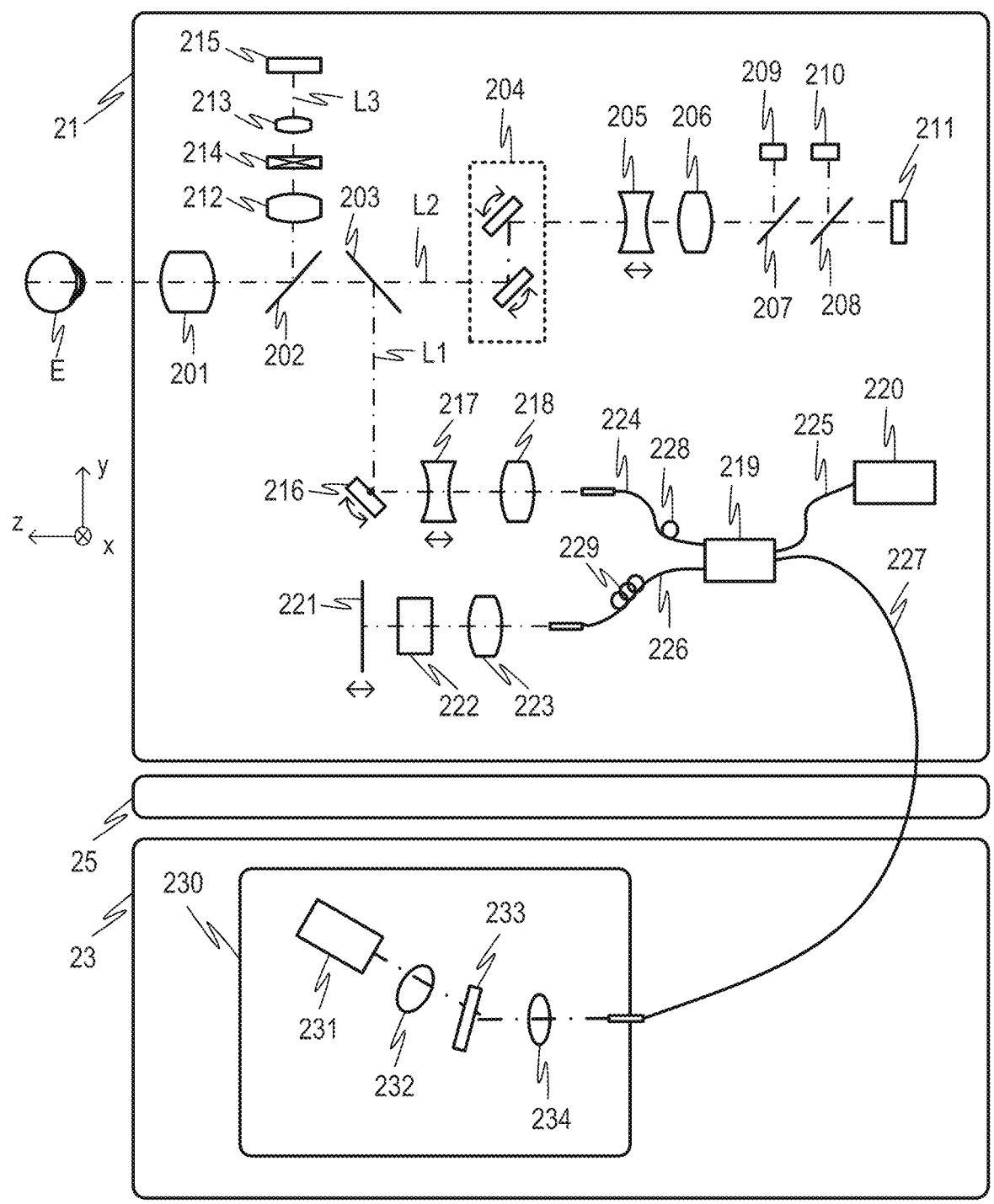
FIG. 2 is a view illustrating a schematic configuration example of an imaging unit according to Embodiment 1.

Next, a configuration of the imaging unit 20 will be described referring to FIG. 2. FIG. 2 is a view that illustrates a schematic configuration example of the imaging unit 20 according to the present embodiment.

First, a configuration of the measurement optical system 21 will be described. In the measurement optical system 21, an objective lens 201 is arranged so as to face an eye to be examined E. and a first dichroic mirror 202 and a second dichroic mirror 203 are arranged on the optical axis of the objective lens 201. The optical path from the objective lens 201 is branched by the dichroic mirrors according to the respective wavelength bands into an optical path L1 of an OCT optical system, an optical path L2 for a fixation lamp and an SLO optical system that serves for both observation of the eye to be examined E and acquisition of an SLO fundus image, and an optical path L3 for observation of the anterior ocular segment.

Note that, in the present embodiment, the optical path L3 for observation of the anterior ocular segment is provided in a reflecting direction of the first dichroic mirror 202, and the optical path L1 of the OCT optical system and the optical path L2 for the SLO optical system and the fixation lamp are provided in a transmitting direction of the first dichroic mirror 202. Further, the optical path L1 of the OCT optical system is provided in a reflecting direction of the second dichroic mirror 203, and the optical path L2 for the SLO optical system and the fixation lamp is provided in a transmitting direction of the second dichroic mirror 203. However, the directions in which the optical paths of the respective optical systems are provided are not limited to these, and may be arbitrarily changed according to a desired configuration.

An SLO scanning unit 204, lenses 205 and 206, a mirror 207, a third dichroic mirror 208, a photodiode 209, an SLO light source 210 and a fixation lamp 211 are provided on the optical path L2 for the SLO optical system and the fixation lamp. Note that, in the present embodiment, the SLO light source 210 is provided in a reflecting direction of the third dichroic mirror 208, and the fixation lamp 211 is provided in a transmitting direction of the third dichroic mirror 208. However, the fixation lamp 211 may be provided in the reflecting direction of the third dichroic mirror 208, and the SLO light source 210 may be provided in the transmitting direction of the third dichroic mirror 208.

The SLO scanning unit 204 is a scanning unit that scans light emitted from the SLO light source 210 and the fixation lamp 211 over the eye to be examined E, and includes an X-scanner that scans in an X-axis direction and a Y-scanner that scans in a Y-axis direction. In the present embodiment, because the X-scanner is required to perform high-speed scanning, the X-scanner is constituted by a polygon mirror, while the Y-scanner is constituted by a galvanometer mirror. Note that, the configuration of the SLO scanning unit 204 is not limited to this configuration, and may be arbitrarily changed according to a desired configuration.

The lens 205 can be driven in an optical axis direction indicated by arrows in the drawing by a motor (not illustrated) or the like that is controlled by the controlling unit 30 for focusing the SLO optical system and the fixation lamp. The mirror 207 is a prism on which a perforated mirror or hollow mirror has been deposited, and can separate projection light from the SLO light source 210 and return light from the eye to be examined E. The third dichroic mirror 208 separates the optical path to the SLO light source 210 and the optical path to the fixation lamp 211 for each wavelength band.

The SLO light source 210, for example, generates light with a wavelength in the vicinity of 780 nm. The photodiode 209 detects the return light from the eye to be examined E with respect to the projection light irradiated from the SLO light source 210. The fixation lamp 211 is used to generate visible light to promote visual fixation of the subject.

The projection light emitted from the SLO light source 210 is reflected by the third dichroic mirror 208, is transmitted through the mirror 207, passes through the lenses 206 and 205, and is scanned over the eye to be examined E by the SLO scanning unit 204. The return light from the eye to be examined E returns along the same path as the projection light, and is thereafter reflected by the mirror 207 and guided to the photodiode 209. The controlling unit 30 can generate an SLO fundus image based on the drive position of the SLO scanning unit 204 and the output from the photodiode 209.

The light emitted from the fixation lamp 211 is transmitted through the third dichroic mirror 208 and the mirror 207, passes through the lenses 206 and 205, and is scanned over the eye to be examined E by the SLO scanning unit 204. At such time, by causing the fixation lamp 211 to flash in accordance with movement of the SLO scanning unit 204, the controlling unit 30 can create an arbitrary shape at any position on the eye to be examined E to thereby promote visual fixation of the subject.

Lenses 212 and 213, a split prism 214, and a CCD 215 for observation of the anterior ocular segment that detects infrared light are disposed on the optical path L3 for observation of the anterior ocular segment. The CCD 215 has sensitivity to a wavelength of irradiation light for observation of the anterior ocular segment (not illustrated), specifically, a wavelength in the vicinity of 970 nm. The split prism 214 is disposed at a position conjugate with a pupil of the eye to be examined E. The controlling unit 30 can generate an anterior ocular segment image based on output of the CCD 215. The controlling unit 30 can detect a distance in a Z-axis direction (front-back direction) of the measurement optical system 21 with respect to the eye to be examined E by using a split image of the anterior ocular segment that is based on light that passed through the split prism 214.

An OCT optical system for capturing a tomographic image of the eye to be examined E is provided on the optical path L1 of the OCT optical system. More specifically, the OCT optical system is used for obtaining interference signals for generating a tomographic image of the eye to be examined E.

An X-Y-scanner 216, lenses 217 and 218, and a fiber end of an optical fiber 224 are provided on the optical path L1 of the OCT optical system. The X-Y-scanner 216 is an OCT scanning unit for scanning measuring light, described later, over the eye to be examined E. Although the X-Y-scanner 216 is illustrated as a single mirror, it is constituted by two galvanometer mirrors for scanning the measuring light in two directions, namely, the X-axis direction and the Y-axis direction. Note that, the configuration of the X-Y-scanner 216 is not limited to this configuration, and may be arbitrarily changed according to a desired configuration. For example, the X-Y-scanner 216 may be constituted by an MEMS mirror that is capable of deflecting light in two-dimensional directions with one mirror.

The lens 217 can be driven in the optical axis direction indicated by arrows in the drawing by a motor (not illustrated) or the like that is controlled by the controlling unit 30. The controlling unit 30 can focus measuring light emitted from the optical fiber 224 that is connected to an optical coupler 219 on the eye to be examined E, by driving the lens 217 using the motor (not illustrated) or the like. As the result of such focusing, return light of the measuring light from the eye to be examined E is imaged into a spot shape at the tip of the optical fiber 224 and simultaneously enters the optical fiber 224.

Next, configurations of an optical path extending from an OCT light source 220, a reference optical system, and a spectrometer 230 will be described. The OCT light source 220 is connected to the optical coupler 219 through an optical fiber 225. Optical fibers 224, 225, 226 and 227 are connected to the optical coupler 219. The optical fibers 224, 225, 226 and 227 are single-mode optical fibers that are connected to and integrated with the optical coupler 219.

A fiber end of the optical fiber 224 is disposed on the OCT optical path L1, and measuring light passes through the optical fiber 224 and a polarization adjustment unit 228 on a measuring light side provided on the optical fiber 224 to thereby enter the OCT optical path L 1. On the other hand, a fiber end of the optical fiber 226 is disposed on an optical path of the reference optical system, and a reference light, described later, passes through the optical fiber 226 and a polarization adjustment unit 229 on the reference light side provided on the optical fiber 226 to thereby enter the optical path of the reference optical system. A lens 223, a dispersion compensation glass 222, and a reference mirror 221 are provided on the optical path of the reference optical system. The spectrometer 230 is connected to the optical fiber 227.

A Michelson interference system is formed by these components. Note that, although a Michelson interference system is used as an interference system in the present embodiment, a Mach-Zehnder interference system may also be used. Depending on the light amount difference between measuring light and reference light, the Mach-Zehnder interference system can be used in a case where the light amount difference is large, and the Michelson interference system can be used in a case where the light amount difference is relatively small.

The OCT light source 220 emits light that is to be used for measurement by OCT. In the present embodiment, a super luminescent diode (SLD) that is a typical low-coherence light source is used as the OCT light source 220. The SLD used in the present embodiment has a central wavelength of 855 nm and a wavelength bandwidth of about 100 nm. In this case, the bandwidth influences the optical axial resolution of the obtained tomographic image and is therefore an important parameter. Further, with respect to the kind of light source, although an SLD is selected in this case, it suffices that the light source is capable of emitting low-coherence light, and an amplified spontaneous emission (ASE) or the like can also be used. In view of the purpose of imaging the eye, the central wavelength can fall within the near infrared range. Further, because the central wavelength influences the lateral resolution of the obtained tomographic image, the central wavelength can be made as short as possible. In the present embodiment, the central wavelength is set to 855 nm because of the two reasons described above.

The light emitted from the OCT light source 220 enters the optical coupler 219 through the optical fiber 225. The light that entered the optical coupler 219 is divided by the optical coupler 219 into measuring light that travels toward the optical fiber 224 side, and reference light that travels toward the optical fiber 226 side. The measuring light passes along the aforementioned optical path L1 of the OCT optical system and is irradiated onto the eye to be examined E that is the object under examination. Return light of the measuring light which is produced as the result of reflection and scattering of the measuring light by the eye to be examined E travels along the same optical path as the measuring light and reaches the optical coupler 219.

On the other hand, the reference light reaches the reference mirror 221 via the optical fiber 226, the lens 223, and the dispersion compensation glass 222 that is inserted for causing the dispersion of the measuring light and the dispersion of the reference light to match, and is then reflected by the reference mirror 221. Thereafter, the reference light returns along the same optical path and reaches the optical coupler 219. The reference mirror 221 is adjustably held in the optical axis direction indicated by an arrow in the drawing, by a motor (not illustrated) or the like controlled by the controlling unit 30.

The measuring light and the reference light are coupled together into interference light by the optical coupler 219. In this case, the interference occurs when the optical path length of the measuring light and the optical path length of the reference light become substantially equal to each other. The controlling unit 30 can cause the optical path length of the reference light to match the optical path length of the measuring light which varies depending on the eye to be examined E by controlling the motor (not illustrated) or the like to move the reference mirror 221 in the optical axis direction.

Note that, the polarization adjustment unit 228 on the measuring light side and the polarization adjustment unit 229 on the reference light side each have several portions where the optical fiber is looped. By causing the loop portions to rotate around the longitudinal direction of each optical fiber to twist the relevant fiber, the polarization adjustment units 228 and 229 can adjust and match polarization states of the measuring light and the reference light.

The interference light generated at the optical coupler 219 is guided via the optical fiber 227 to the spectrometer 230 provided in the base unit 23. Lenses 234 and 232, a diffraction grating 233, and a line sensor 231 are provided in the spectrometer 230. The interference light which exited from the optical fiber 227 is converted into parallel light by the lens 234, and then spectrally separated by the diffraction grating 233, and imaged onto the line sensor 231 by the lens 232. The controlling unit 30 can generate a tomographic image of the eye to be examined E using an interference signal based on the interference light that is output from the line sensor 231.

By means of the above configuration, a tomographic image of the eye to be examined E can be obtained using the imaging unit 20, and even in the case of near infrared light, an SLO fundus image of the eye to be examined E with high contrast can be obtained.

(Method for Imaging Tomographic Image)

Next, a method for imaging a tomographic image using the OCT apparatus 1 will be described. In the OCT apparatus 1, a tomographic image of a predetermined site of the eye to be examined E can be imaged by control of the X-Y-scanner 216 by the controlling unit 30. Here, a trajectory along which measuring light is scanned over the eye to be examined E is referred to as a "scan pattern". Examples of scan patterns include a cross scan for which scanning is performed vertically and horizontally in a cross shape that is centered on one point, and a 3D scan that obtains a three-dimensional tomographic image as a result of performing scanning so as to fill an entire area. A cross scan is suitable in a case where it is desired to perform a detailed observation with respect to a specific site, and a 3D scan is suitable in a case where it is desired to observe a layer structure or a layer thickness of the entire retina.

Here, an imaging method in a case where a 3D scan is executed will be described. First, scanning of measuring light in the X-axis direction (main scanning direction) in the drawing is performed, and information pertaining to a predetermined number of rounds of imaging from an imaging range in the X-axis direction of the eye to be examined E is obtained by the line sensor 231.

Here, obtaining tomographic information in the depth direction at one point in the X-axis direction of the eye to be examined E is referred to as an "A-scan". The intensity distribution on the line sensor 231 that is obtained by the A-scan is subjected to a fast Fourier transformation (FFT), and the linear intensity distribution obtained by the FFT is converted into density information in order to display the obtained information on the display unit 50. Thus, an A-scan image that is based on information obtained by the A-scan can be generated. Further, by aligning a plurality of A-scan images, a B-scan image that is a two-dimensional image can be obtained.

By performing imaging of a plurality of A-scan images for forming one B-scan image, and thereafter moving the scanning position in the Y-axis direction (subscanning direction) and performing scanning again in the X-axis direction, a plurality of B-scan images can be obtained. By displaying a plurality of B-scan images or a three-dimensional tomographic image constructed from a plurality of B-scan images on the display unit 50, the examiner can observe the three-dimensional tomographic state of the eye to be examined E. The examiner can perform diagnosis of the eye to be examined E based on the image. Although an example in which a three-dimensional tomographic image is obtained by obtaining a plurality of B-scan images in the X-axis direction has been described here, a three-dimensional tomographic image may also be obtained by obtaining a plurality of B-scan images in the Y-axis direction. Note that, the scanning directions are not limited to the X-axis direction and the Y-axis direction, and it suffices that the scanning directions are axial directions which are orthogonal to the Z-axis direction and which intersect with each other.

(Configuration of Controlling Unit)

Figure 3:
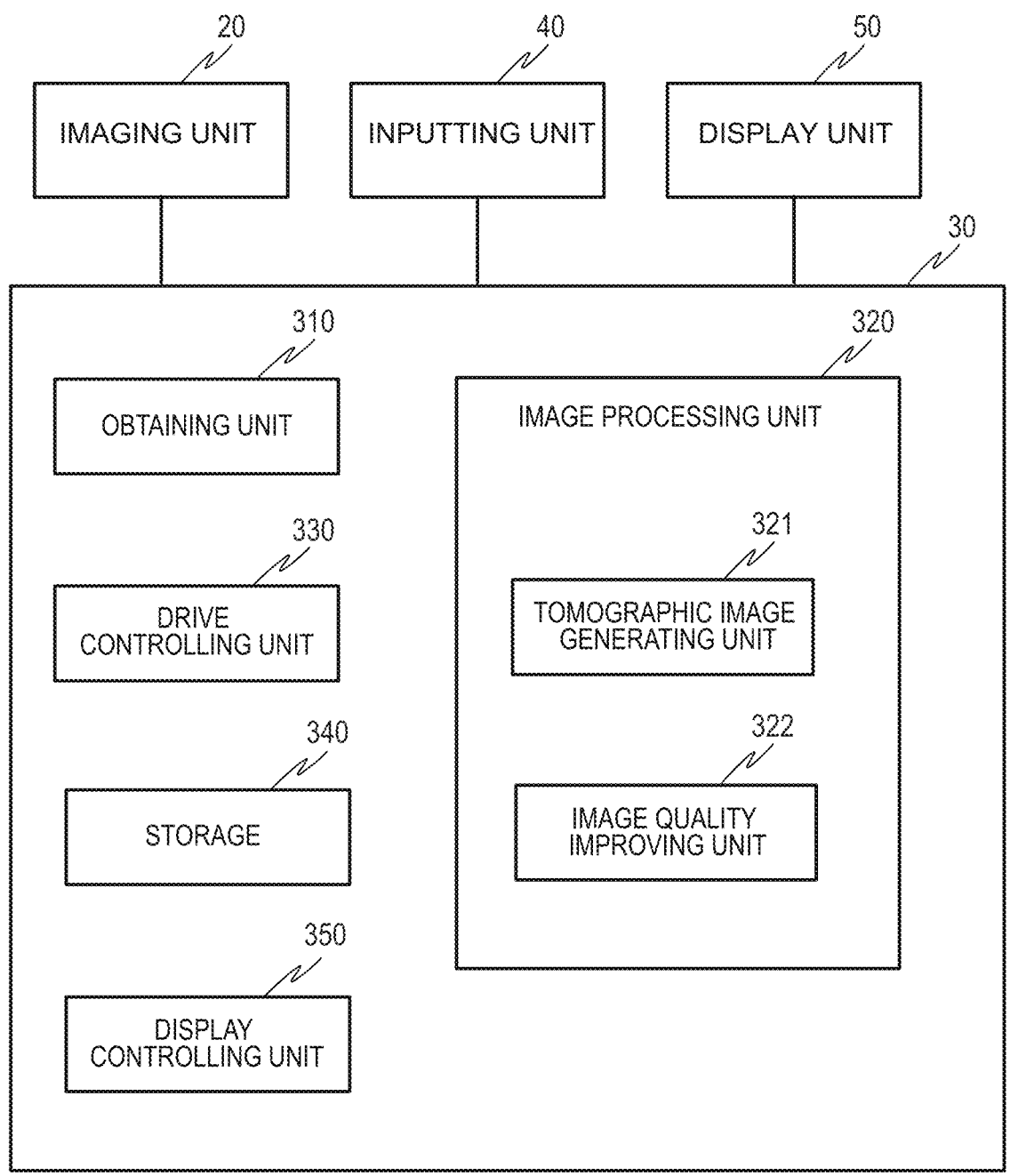
FIG. 3 is a view illustrating a schematic configuration example of a controlling unit according to Embodiment 1.

Next, the controlling unit 30 will be described referring to FIG. 3. FIG. 3 illustrates a schematic configuration example of the controlling unit 30. An obtaining unit 310, an image processing unit 320, a drive controlling unit 330, a storage 340 and a display controlling unit 350 are provided in the controlling unit 30.

The obtaining unit 310 can obtain data of output signals of the CCD 215 and the photodiode 209 as well as data of an output signal of the line sensor 231 corresponding to an interference signal of the eye to be examined E from the imaging unit 20. Note that, the data of the output signal that the obtaining unit 310 obtains may be an analog signal or a digital signal. In a case where the obtaining unit 310 obtains an analog signal, the controlling unit 30 can convert the analog signal into a digital signal.

Further, the obtaining unit 310 can obtain various kinds of data such as tomographic data generated by the image processing unit 320, and various kinds of images such as a tomographic image, an SLO fundus image and an anterior ocular segment image. Here, the term "tomographic data" refers to data including information relating to a cross-section of an object under examination, and includes a signal obtained by subjecting an interference signal obtained by OCT to Fourier transformation, and a signal or the like obtained by subjecting the relevant signal to any processing.

In addition, the obtaining unit 310 can obtain an imaging conditions group (for example, information relating to the imaging date and time, an imaged site name, an imaged region, an imaging angle of view, an imaging system, an image resolution and gradation, an image size, an image filter, and the image data format) of the image to be subjected to image processing. Note that the imaging conditions group is not limited to the example of an imaging conditions group described in the foregoing. Further, the imaging conditions group need not include all of the conditions mentioned in the foregoing example, and may include some of these conditions.

Specifically, the obtaining unit 310 obtains the imaging conditions of the imaging unit 20 when imaging the relevant image. Further, depending on the data format of the image, the obtaining unit 310 can also obtain an imaging conditions group that is stored in a data structure constituting the image. Note that, in a case where imaging conditions are not stored in the data structure of the image, the obtaining unit 310 can also separately obtain an imaging information group that includes an imaging conditions group from a storage apparatus or the like that stores imaging conditions.

Further, the obtaining unit 310 can also obtain information for identifying the eye to be examined, such as a subject identification number, from the inputting unit 40 or the like. Note that the obtaining unit 310 may obtain various kinds of data, various kinds of images or various kinds of information from the storage 340 or another apparatus (not illustrated) connected to the controlling unit 30. The obtaining unit 310 can store various kinds of data or images that were obtained in the storage 340.

The image processing unit 320 can generate a tomographic image from data obtained by the obtaining unit 310 or data stored in the storage 340, and can perform image processing on a generated or obtained tomographic image. A tomographic image generating unit 321 and an image quality improving unit 322 are provided in the image processing unit 320.

The tomographic image generating unit 321 can subject the interference signal data obtained by the obtaining unit 310 to wavenumber conversion, Fourier transformation, absolute value conversion (acquisition of amplitude) or the like to generate tomographic data, and can generate a tomographic image of the eye to be examined E based on the tomographic data. The interference signal data obtained by the obtaining unit 310 may be data of a signal that was output from the line sensor 231, or may be data of an interference signal obtained from the storage 340 or an apparatus (not illustrated) connected to the controlling unit 30. Note that, any known method may be adopted as a method for generating a tomographic image, and a detailed description thereof is omitted here.

The image quality improving unit 322 uses a learned model that is described later to generate a high quality tomographic image based on a tomographic image generated by the tomographic image generating unit 321. Note that, the image quality improving unit 322 can also generate a high quality tomographic image based on a tomographic image that the obtaining unit 310 obtained from the storage 340 or another apparatus (not illustrated) connected to the controlling unit 30, and not just based on a tomographic image or the like that was imaged using the imaging unit 20.

The drive controlling unit 330 can control driving of components such as the OCT light source 220, the X-Y-scanner 216, the lens 217, the reference mirror 221, the SLO light source 210, the SLO scanning unit 204, the lens 205 and the fixation lamp 211 of the imaging unit 20 which is connected to the controlling unit 30.

The storage 340 can store various kinds of data obtained by the obtaining unit 310, and various kinds of data and images such as a tomographic image which was generated and processed by the image processing unit 320. Further, the storage 340 can store attributes (name, age, or the like) of a subject, information relating to the eye to be examined such as measurement results (axial length of eyeball, intraocular pressure, or the like) obtained using other inspection equipment, imaging parameters, image analysis parameters, and parameters set by the operator. In addition, the storage 340 can also store statistical information of a normal database. Note that, a configuration may also be adopted in which these images and information are stored in an external storage apparatus (not illustrated). The storage 340 can also store a program for carrying out the functions of the respective components of the controlling unit 30 by being executed by a processor.

The display controlling unit 350 can cause various kinds of information obtained by the obtaining unit 310 and various kinds of images such as a tomographic image which was generated and processed by the image processing unit 320 to be displayed on the display unit 50. The display controlling unit 350 can also cause information that was input by a user and the like to be displayed on the display unit 50.

The controlling unit 30 may be constituted, for example, by using a general-purpose computer. Note that, the controlling unit 30 may be constituted by using a dedicated computer of the OCT apparatus 1. The controlling unit 30 is equipped with a CPU (central processing unit) (not illustrated) or MPU (micro processing unit) and a storage medium including a memory such as an optical disk or ROM (read only memory). The respective components other than the storage 340 of the controlling unit 30 may be constituted by a software module that is executed by a processor such as a CPU or an MPU. Further, the respective components in question may be constituted by a circuit that serves a specific function such as an ASIC, or an independent apparatus or the like. The storage 340, for example, may be constituted by any storage medium such as an optical disk or a memory.

Note that, the controlling unit 30 may include one or a plurality of processors such as a CPU and storage media such as ROM. Therefore, each component of the controlling unit 30 may be configured to function in a case where at least one processor and at least one storage medium are connected, and the at least one processor executes a program stored in the at least one storage medium. Note that, the processor is not limited to a CPU or an MPU, and may be a GPU (graphics processing unit) or an FPGA (field-programmable gate array) or the like.

Next, to describe image quality improving processing with respect to a tomographic image according to the present embodiment, segmentation processing and gradation conversion processing will be described referring to FIG. 4 to FIG. 5D.

(Segmentation Processing)

Figure 4:
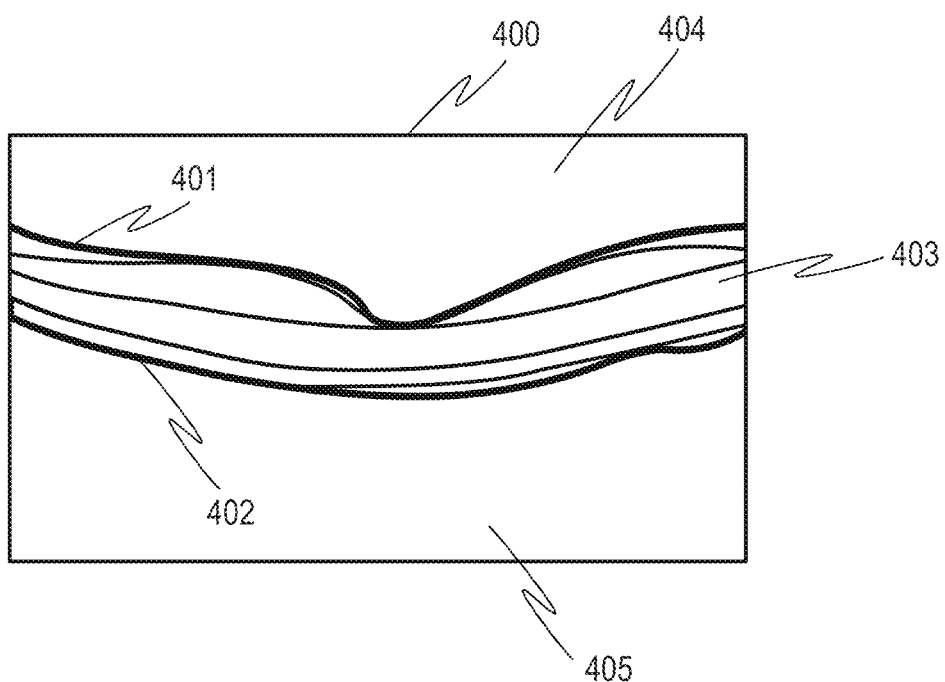
FIG. 4 is an explanatory drawing for describing segmentation of a retina portion, a vitreous body portion and a choroid portion.

FIG. 4 is a view illustrating an example of a tomographic image in which boundaries of respective regions of retinal layers were detected by segmentation processing. Segmentation processing of a tomographic image is capable of detecting the boundaries of respective regions included in the tomographic image. In the case of a tomographic image 400 illustrated in FIG. 4, a boundary 401 between a vitreous body portion and a retina portion, and a boundary 402 between the retina portion and a choroid portion are detected. By detecting the boundaries 401 and 402 in the tomographic image 400, a region 403 of the retina portion between the boundary 401 and the boundary 402, a region 404 of the vitreous body portion that is on a shallow layer side from the boundary 401, and a region 405 of the choroid portion that is on a deep layer side from the boundary 402 can be identified.

Any known method can be used as the segmentation processing. As one example, first, a median filter and a Sobel filter are each applied to the tomographic image that is the object to be processed, to thereby generate a median image and a Sobel image. Next, from the generated median image and Sobel image, a profile is generated for each item of tomographic data corresponding to an A-scan. Here, the generated profiles are intensity value profiles in the case of a median image, and gradient profiles in the case of a Sobel image. Thereafter, peaks in the profiles generated from the Sobel image are detected. By referring to median image profiles corresponding to preceding and succeeding regions of detected peaks or regions between peaks, boundaries between respective regions in the retinal layers can be detected.

(Gradation Conversion Processing)

Figure 5A:
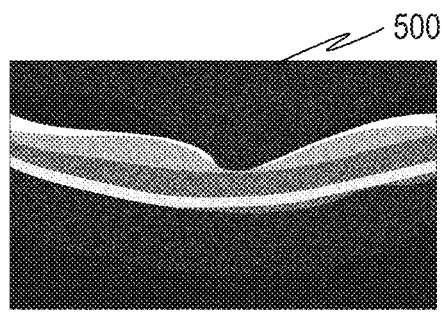
FIG. 5A is an explanatory drawing for describing general display image processing.

Next, referring to FIG. 5A to FIG. 5D, gradation conversion processing for enhancing the contrast in the region 404 of the vitreous body portion and the region 405 of the choroid portion, the region 403 of the retina portion, or all of these regions will be described. FIG. 5A illustrates a tomographic image 500 as one example of a source tomographic image obtained by imaging the eye to be examined E (hereunder, referred to as an "original tomographic image"). The tomographic image 500 is usually in integer format of 10 or more bits, and is data with a high dynamic range including data in a range from extremely low intensity information to high intensity information. On the other hand, as described above, the data that can be displayed on the display unit 50 is low dynamic range data, for example, 8-bit integer data. Therefore, gradation conversion processing is performed so that the data of the original tomographic image 500 becomes low dynamic range data for display.

Figure 5B:
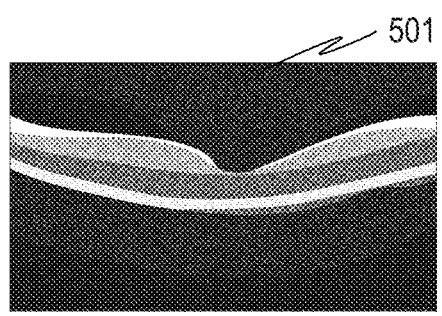
FIG. 5B is an explanatory drawing for describing the general display image processing.

FIG. 5B is a view illustrating a tomographic image 501 obtained by subjecting the original tomographic image 500 to gradation conversion processing so that the region of the retina portion is easy to observe, in other words, to ensure the contrast of the region of the retina portion. The gradation conversion processing for ensuring the contrast of the region of the retina portion will now be described referring to FIG. 6A and FIG. 6B.

Figure 6A:
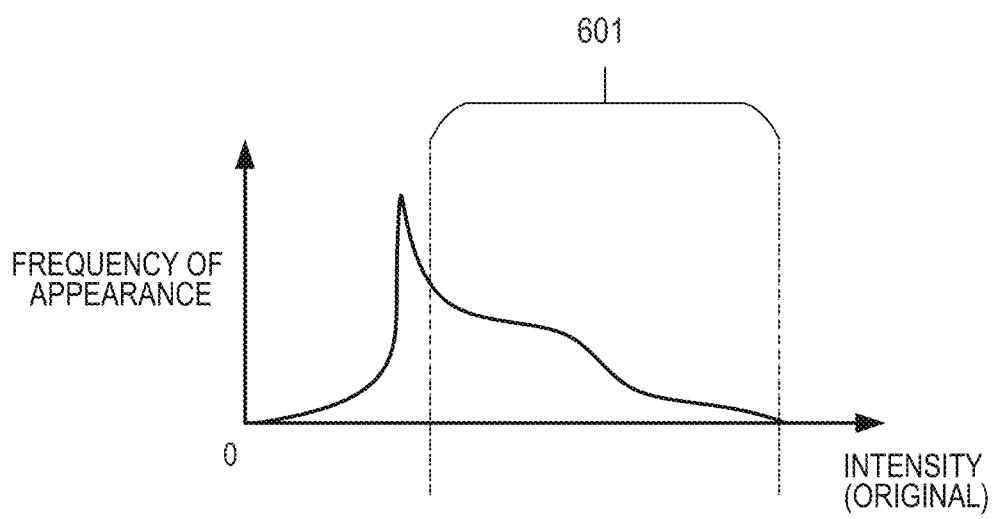
FIG. 6A is an explanatory drawing for describing conversion processing that facilitates observation of a retina portion.
Figure 6B:
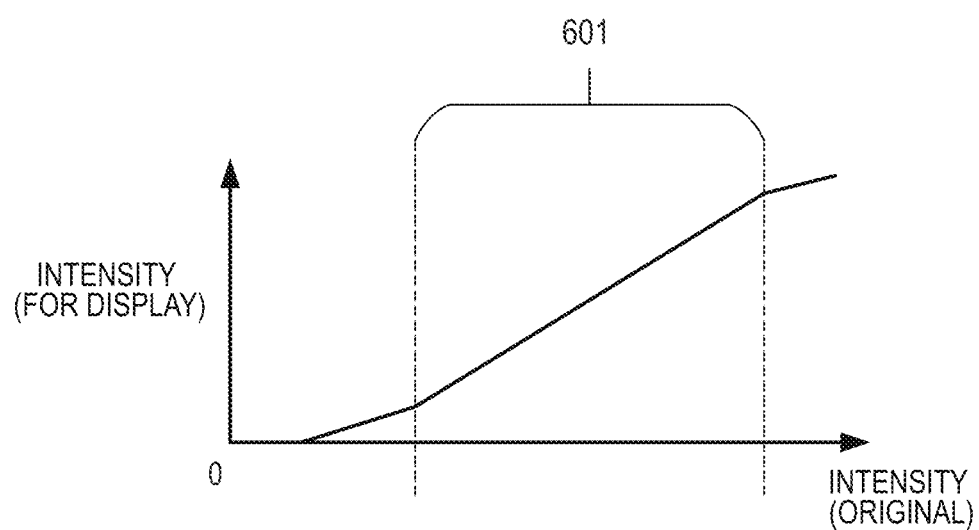
FIG. 6B is an explanatory drawing for describing the conversion processing that facilitates observation of a retina portion.

FIG. 6A is a view illustrating the frequency of appearance of intensity values in the tomographic image 500, and illustrates a range 601 of intensity values corresponding to intensity values of the region of the retina portion. Note that, the range of intensity values corresponding to intensity values of the region of the retina portion may be determined based on an average intensity range that is obtained empirically with respect to the region of the retina portion. In the gradation conversion processing in question, conversion processing is performed so that the intensity range 601 corresponding to intensity values of the region of the retina portion becomes a wide range of intensity values relating to data for display, as illustrated in FIG. 6B. By this means, the tomographic image 501 for display in which the region of the retina portion is easy to observe can be generated.

Figure 5C:
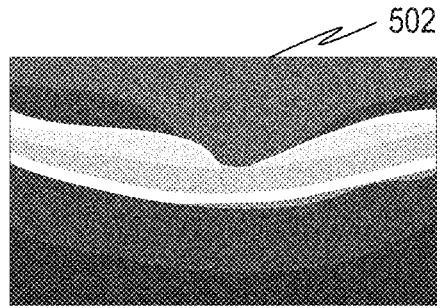
FIG. 5C is an explanatory drawing for describing the general display image processing.

FIG. 5C is a view illustrating a tomographic image 502 obtained by subjecting the original tomographic image 500 to gradation conversion processing so that regions of a vitreous body portion and a choroid portion are easy to observe, in other words, to ensure the contrast of the regions of the vitreous body portion and the choroid portion. The gradation conversion processing for ensuring the contrast of the regions of the vitreous body portion and the choroid portion will now be described referring to FIG. 7A and FIG. 7B.

Figure 7A:
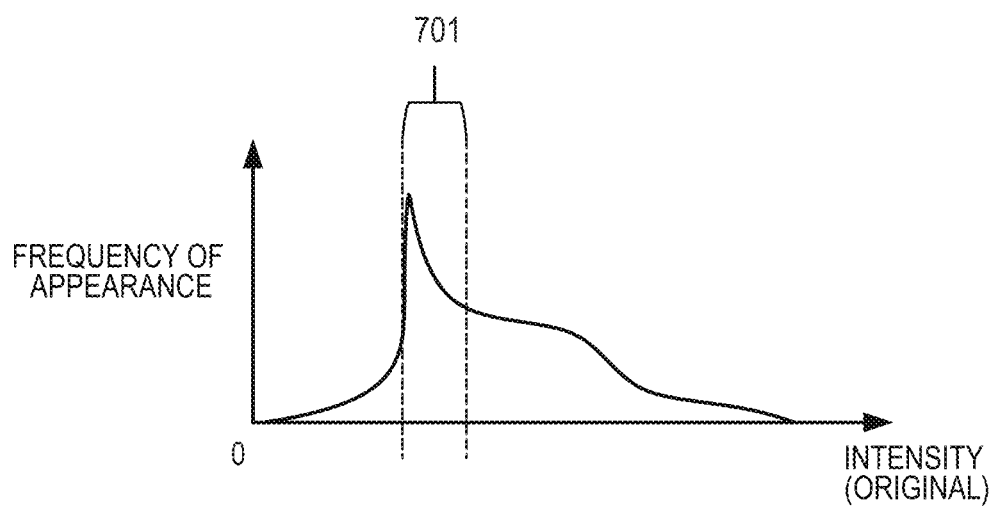
FIG. 7A is an explanatory drawing for describing conversion processing that facilitates observation of a vitreous body portion and a choroid portion.
Figure 7B:
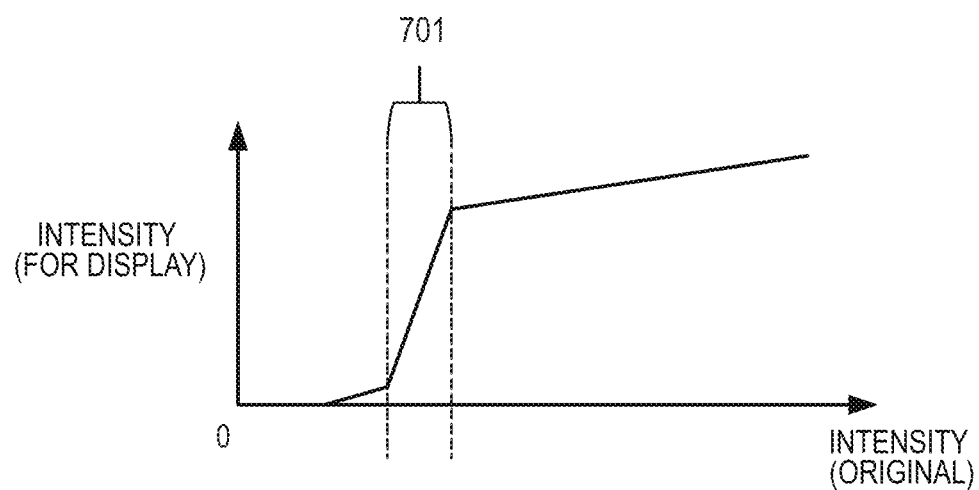
FIG. 7B is an explanatory drawing for describing the conversion processing that facilitates observation of a vitreous body portion and a choroid portion.

FIG. 7A is a view illustrating the frequency of appearance of intensity values in the tomographic image 500, and illustrates a range 701 of intensity values corresponding to intensity values of the regions of the vitreous body portion and the choroid portion. Note that, the range of intensity values corresponding to intensity values of the regions of the vitreous body portion and the choroid portion may be determined based on an average intensity range that is obtained empirically with respect to a region of the vitreous body portion and a region of the choroid portion. In the gradation conversion processing in question, conversion processing is performed so that the intensity range 701 corresponding to intensity values of the regions of the vitreous body portion and the choroid portion becomes a wide range of intensity values relating to data for display, as illustrated in FIG. 7B. By this means, the tomographic image 502 for display in which the regions of the vitreous body portion and the choroid portion are easy to observe can be generated.

Figure 5D:
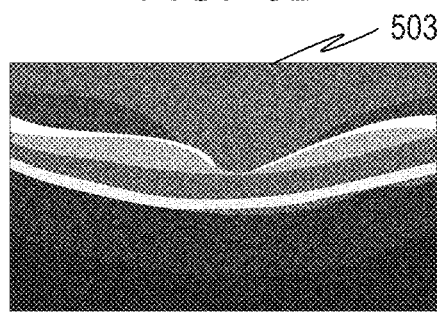
FIG. 5D is an explanatory drawing for describing the general display image processing.

FIG. 5D is a view illustrating a tomographic image 503 obtained by performing gradation conversion processing so that the regions of the retina portion, the vitreous body portion and the choroid portion are easy to observe, in other words, so as to ensure the contrast of these regions. In this case, first, the boundary 401 between the vitreous body portion and the retina portion and the boundary 402 between the retina portion and the choroid portion are detected by the aforementioned segmentation processing, and the region 403 of the retina portion, the region 404 of the vitreous body portion, and the region 405 of the choroid portion are identified.

Thereafter, gradation conversion processing is performed with respect to the region 403 of the retina portion so that the range 601 of intensity values corresponding to the region of the retina portion becomes a wide range of intensity values relating to data for display, as illustrated in FIG. 6B. On the other hand, gradation conversion processing is performed with respect to the region 404 of the vitreous body portion and the region 405 of the choroid portion so that the range 701 of intensity values corresponding to the regions of the vitreous body portion and the choroid portion becomes a wide range of intensity values relating to data for display, as illustrated in FIG. 7B. By this means, the tomographic image 503 for display in which the regions of the retina portion, the vitreous body portion and the choroid portion are easy to observe can be generated.

Note that, not only can the same conversion processing be performed on the vitreous body portion and the choroid portion, but conversion processing that differs between the vitreous body portion and the choroid portion can also be performed. Further, it is possible to perform not only linear conversion processing, but also to perform S-curve conversion processing such as sigmoidal conversion or γ-conversion.

In the gradation conversion processing for generating a tomographic image in which the overall regions of the retina portion, the vitreous body portion and the choroid portion are easy to observe that is described above, detection of the regions in the tomographic image is performed by segmentation processing. Therefore, if erroneous detection by segmentation processing occurs due to a change in a layer structure caused by a lesion in a diseased eye, in some cases the gradation conversion processing will not be properly performed, and a tomographic image in which the overall regions are easy to observe cannot be generated.

In contrast, in the case of the controlling unit 30 according to the present embodiment, a high quality tomographic image which is easy to observe and seems to be an image for which different image processing has been performed on each region in a tomographic image is generated by using a learned model of a machine learning model according to an arbitrary machine learning algorithm such as deep learning. When performing segmentation processing using a learned model, for example, even if a layer structure changes due to a lesion in a diseased eye, image processing can be appropriately performed according to the learned tendency.

Note that, in the present description the term "high quality image" refers to an image that has been converted into an image with image quality that is more suitable for image diagnosis, and the term "image quality improving processing" refers to converting an input image into an image with image quality that is more suitable for image diagnosis. In this case, the content of image quality which is suitable for image diagnosis depends on what it is desired to diagnose using various kinds of image diagnosis. Therefore, while it is not possible to say so unconditionally, for example, image quality that is suitable for image diagnosis includes image quality in which the imaging target is displayed in colors and gradations which make the imaging target easy to observe, in which the amount of noise is low, the contrast is high, the image size is large and the resolution is high. In addition, image quality that is suitable for image diagnosis can include image quality such that objects or gradations which do not actually exist and that were rendered during the process of image generation are removed from the image.

(Learning of Machine Learning)

A learned model according to the present embodiment will now be described referring to FIG. 8A to FIG. 10. First, training data relating to a learned model will be described referring to FIG. 8A to FIG. 9B.

The training data is composed of one or more pair groups of input data and output data. In the present embodiment, specifically, training data is composed of pair groups in which an original tomographic image obtained by an OCT apparatus such as the tomographic image 500 is adopted as input data, and a tomographic image subjected to image processing so as to enable comprehensive observation such as the tomographic image 503 is adopted as output data. Note that, an image obtained by performing image processing on the tomographic image serving as the input data can be adopted as the output data.

Figure 8A:
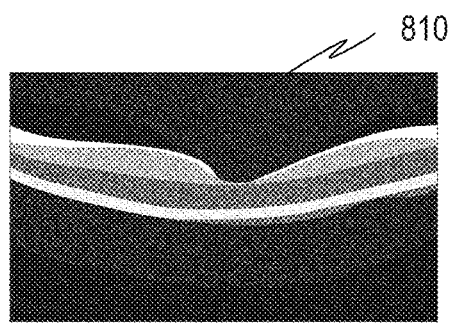
FIG. 8A is a view illustrating an example of training data.
Figure 8B:
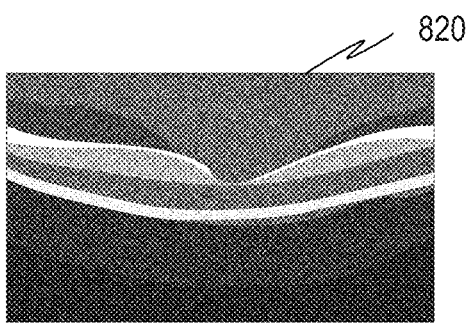
FIG. 8B is a view illustrating an example of the training data.

First, a case is described in which one pair group constituting the training data is taken as being composed of an original tomographic image 810 and a high quality tomographic image 820 illustrated in FIG. 8A and FIG. 8B. In this case, as illustrated in FIG. 8A and FIG. 8B, a pair is formed in which the entire original tomographic image 810 is taken as input data, and the entire high quality tomographic image 820 is taken as output data. Note that, although in the example illustrated in FIG. 8A and FIG. 8B a pair composed of input data and output data is formed by using each image in its entirety, a pair is not limited thereto.

Figure 9A:
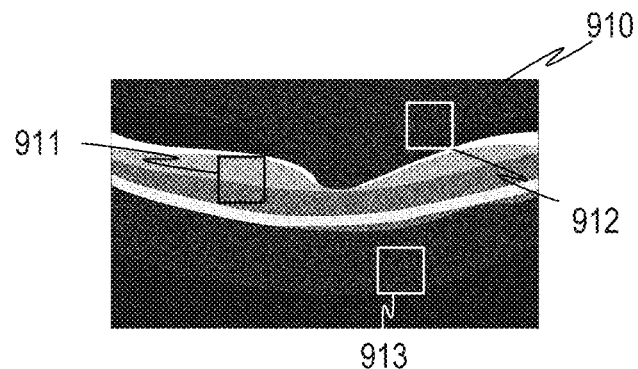
FIG. 9A is a view illustrating an example of the training data.
Figure 9B:
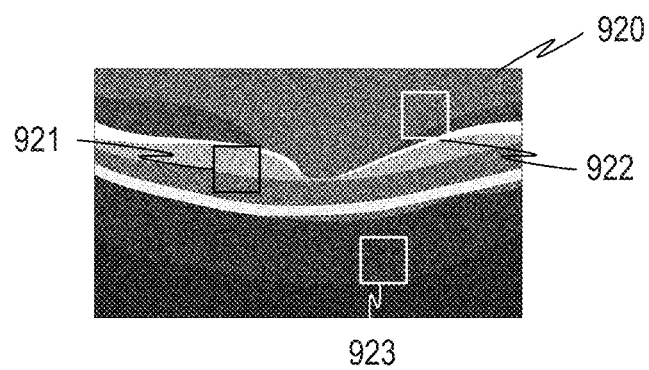
FIG. 9B is a view illustrating an example of the training data.

For example, as illustrated in FIG. 9A and FIG. 9B, a pair may be formed in which a rectangular region image 911 in an original tomographic image 910 is adopted as input data, and a rectangular region image 921 that is a corresponding imaged region in a high quality tomographic image 920 is adopted as output data. Here, the rectangular region image 911 and the rectangular region image 921 are images in a corresponding positional relationship in the tomographic image 910 and the high quality tomographic image 920.

Note that, when performing learning, the scanning range (imaging angle of view) and scanning density (number of A-scans and number of B-scans) can be normalized to make the image sizes uniform, so that the rectangular region sizes when performing learning can be made uniform. Further, the rectangular region images illustrated in FIG. 8A to FIG. 9B are examples of rectangular region sizes when the respective rectangular region sizes are used for performing learning separately from each other.

Further, the number of rectangular regions can be set to one in the example illustrated in FIG. 8A and FIG. 8B, and can be set to a plurality of rectangular regions in the example illustrated in FIG. 9A and FIG. 9B. For example, in the example illustrated in FIG. 9A and FIG. 9B, a pair can also be constituted in which a rectangular region images 912 and 913 in the tomographic image 910 are adopted as input data and rectangular region images 922 and 923 that are corresponding imaged regions in the high quality tomographic image 920 are adopted as output data. Thus, pairs of rectangular region images which are different to each other can be created from a pair composed of one tomographic image and one high quality tomographic image. Note that, the content of pair groups constituting the training data can be enhanced by creating a large number of pairs of rectangular region images while changing the positions of the rectangular regions to different coordinates in the tomographic image and the high quality tomographic image that are the source images.

Here, the rectangular region image 911 is an image of a region of the retina portion in the original tomographic image 910, and the rectangular region image 921 is an image of a region of the retina portion in the high quality tomographic image 920 that was subjected to image processing such as gradation conversion processing so as to enable a comprehensive observation. Similarly, the rectangular region image 912 is an image of a region of the vitreous body portion in the original tomographic image 910, and the rectangular region image 922 is an image of a region of the vitreous body portion in the high quality tomographic image 920. Further, the rectangular region image 913 is an image of a region of the choroid portion in the original tomographic image 910, and the rectangular region image 923 is an image of a region of the choroid portion in the high quality tomographic image 920.

Although the rectangular regions are illustrated discretely in the example illustrated in FIG. 9A and FIG. 9B, the tomographic image and the high quality tomographic image that are the source images can each be divided into a group of rectangular region images of a uniform size continuously and without gaps. Alternatively, the tomographic image and the high quality tomographic image that are the source images may each be divided into a rectangular region image group at random positions which correspond to each other. In this way, by selecting images of smaller regions as a pair composed of input data and output data as the rectangular regions, a large amount of pair data can be generated from the tomographic image 910 and the high quality tomographic image 920 constituting the original pair. Consequently, the time required for training the machine learning model can be shortened.

Note that, the output data is not limited to a high quality tomographic image generated from a single tomographic image. A tomographic image for display may also be used that was generated with respect to a tomographic image obtained by performing arithmetic averaging processing or the like using a plurality of tomographic images obtained by imaging the same site of an eye to be examined a plurality of times.

Note that, the rectangular region is not limited to a square shape, and may be an oblong shape. In addition, the rectangular region may be a region that corresponds to one A-scan. Further, when preparing output data for learning, better data can be prepared by performing manual adjustment, and not just by generating data by predetermined automatic processing.

In addition, among the pair groups constituting the training data, pairs that do not contribute to improving image quality can be removed from the training data. For example, if the image quality of a high quality image that is output data included in one pair of the training data is not suitable for image diagnosis, there is a probability that an image that is output by a learned model that learned using the relevant training data will have image quality that is not suitable for image diagnosis. Therefore, by removing pairs of which the image quality of the output data is not suitable for image diagnosis from the training data, the probability of the learned model generating an image with image quality that is not suitable for image diagnosis can be reduced.

In addition, in a case where the structure or position of an imaging target to be rendered differs greatly in an image group which is a pair, there is a probability that a learned model that learned using the relevant training data will output an image which is not suitable for image diagnosis in which the imaging target is rendered with a structure or at a position that greatly differs from the input image. Therefore, a pair of input data and output data in which the structure or position of the imaging target to be rendered differs greatly between the input data and output data can also be removed from the training data.

Figure 10:
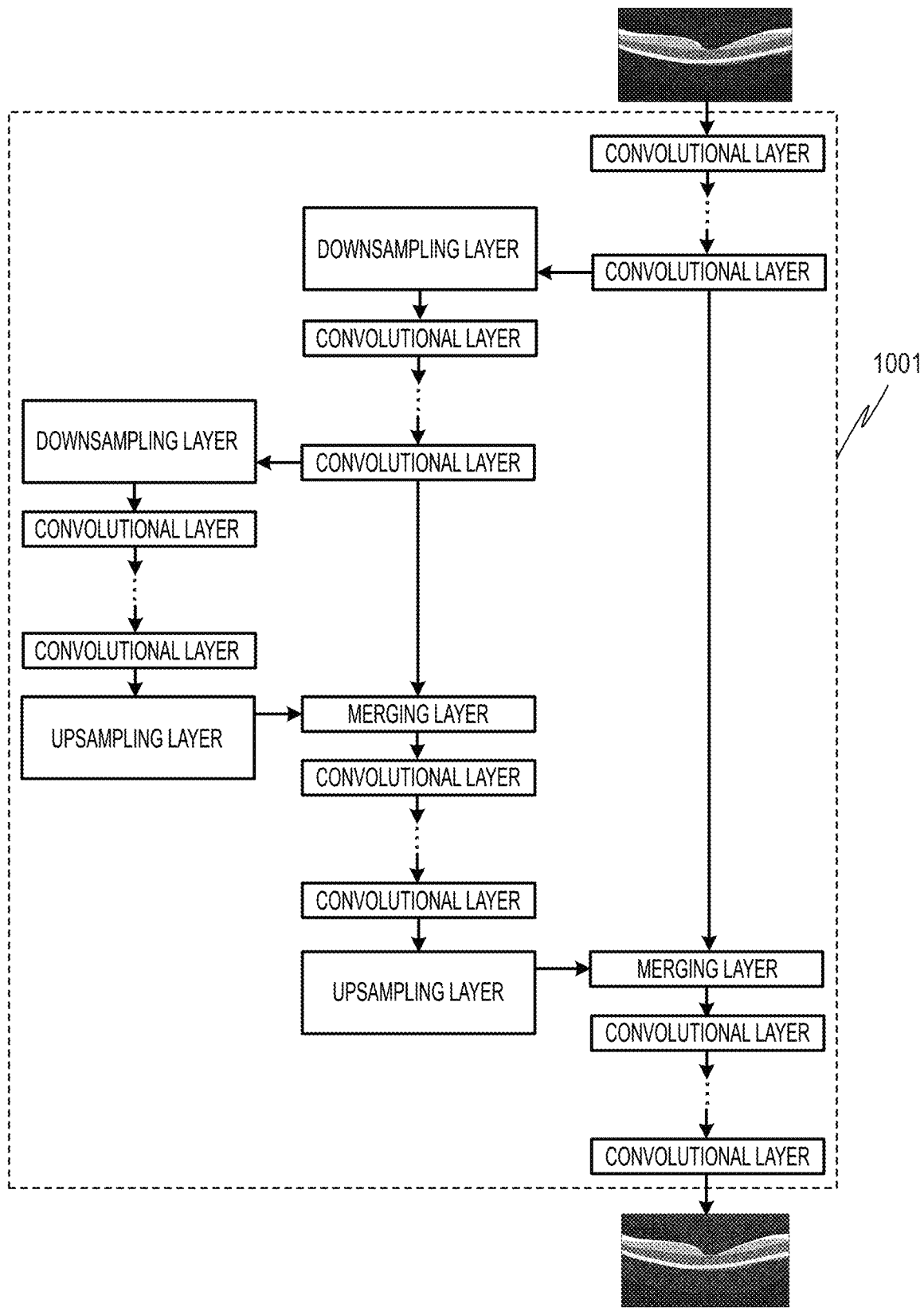
FIG. 10 is a view illustrating an example of the configuration of a learned model.

Next, as one example of a learned model according to the present embodiment, a convolutional neural network (CNN) that performs image quality improving processing with respect to an input tomographic image is described using FIG. 10.

The learned model illustrated in FIG. 10 is constituted by a plurality of layer groups that are responsible for processing to process an input value group for output. Note that, the types of layers included in a configuration 1001 of the learned model are a convolutional layer, a downsampling layer, an upsampling layer, and a merging layer.

The convolutional layer is a layer that performs convolutional processing with respect to an input value group according to parameters such as the kernel size of the filters, the number of filters, the value of a stride, and the dilation value which are set. Note that, the number of dimensions of the kernel size of the filter may be changed according to the number of dimensions of an input image.

The downsampling layer is a layer that performs processing for making the number of output value groups less than the number of input value groups by thinning out or combining the input value groups. Specifically, for example, max pooling processing is available as such processing.

The upsampling layer is a layer that performs processing for making the number of output value groups greater than the number of input value groups by duplicating an input value group or adding a value interpolated from an input value group. Specifically, for example, linear interpolation processing is available as such processing.

The merging layer is a layer that performs processing that inputs, from a plurality of sources, value groups such as an output value group of a certain layer or a pixel value group constituting an image, and merges the value groups by concatenating or adding the value groups.

Note that, as parameters that are set for convolutional layer groups included in the configuration 1001 illustrated in FIG. 10, it is possible to perform image quality improving processing of a certain accuracy by, for example, setting the kernel size of the filters to a width of three pixels and a height of three pixels, and the number of filters to 64. However, it is necessary to pay attention in this regard because if the settings of parameters with respect to layer groups and node groups constituting a neural network differ, in some cases the degrees to which a tendency trained based on training data is reproducible in the output data will differ. That is, in many cases, the appropriate parameters will differ according to the form at the time of implementation, and therefore parameters can be changed to preferable values as needed.

Further, there are also cases where the CNN can obtain better characteristics by changing the configuration of the CNN, and not just by using a method that changes parameters as described above. The term "better characteristics" refers to, for example, the accuracy of image quality improving processing increasing, the time taken for image quality improving processing becoming shorter, and the time required for training of the machine learning model becoming shorter.

Note that, the configuration 1001 of the CNN used in the present embodiment is a U-Net type machine learning model that has a function of an encoder that is composed of a plurality of levels including a plurality of downsampling layers, and a function of a decoder that is composed of a plurality of levels including a plurality of upsampling layers. In the U-Net type machine learning model, positional information (spatial information) that has been made ambiguous in a plurality of levels configured as an encoder is configured (for example, using a skip connection) so that the information can be used in levels of the same dimension (levels corresponding to each other) in a plurality of levels configured as a decoder.

Although not illustrated in the drawings, as a modification of the configuration of the CNN, for example, a batch normalization layer or an activation layer that uses a rectifier linear unit may be incorporated after the convolutional layer or the like.

When data is input to a learned model of a machine learning model of this kind, data in accordance with the design of the machine learning model is output. For example, output data is output that has a high probability of corresponding to the input data in accordance with a tendency for which the machine learning model was trained using training data. When an original tomographic image is input to the learned model according to the present embodiment, a high quality tomographic image in which a retina portion, a vitreous body portion and a choroid portion are easy to observe that is used for comprehensive observation is output.

Note that, in a case where learning is performed in a manner which involves dividing a tomographic image into regions, the learned model outputs rectangular region images that are high quality tomographic images corresponding to the respective rectangular regions. In this case, first, the image quality improving unit 322 divides the tomographic image that is the input image into a rectangular region image group based on the image size when performing learning, and inputs the group of divided rectangular region images into the learned model. Thereafter, the image quality improving unit 322 arranges the respective images of a group of rectangular region images that are high quality tomographic images obtained using the learned model according to the same positional relationship as that of the respective images of the rectangular region image group that was input to the learned model, and combines the rectangular region images. By this means, the image quality improving unit 322 can generate a high quality tomographic image corresponding to the input tomographic image.

(Flowchart)

Figure 11:
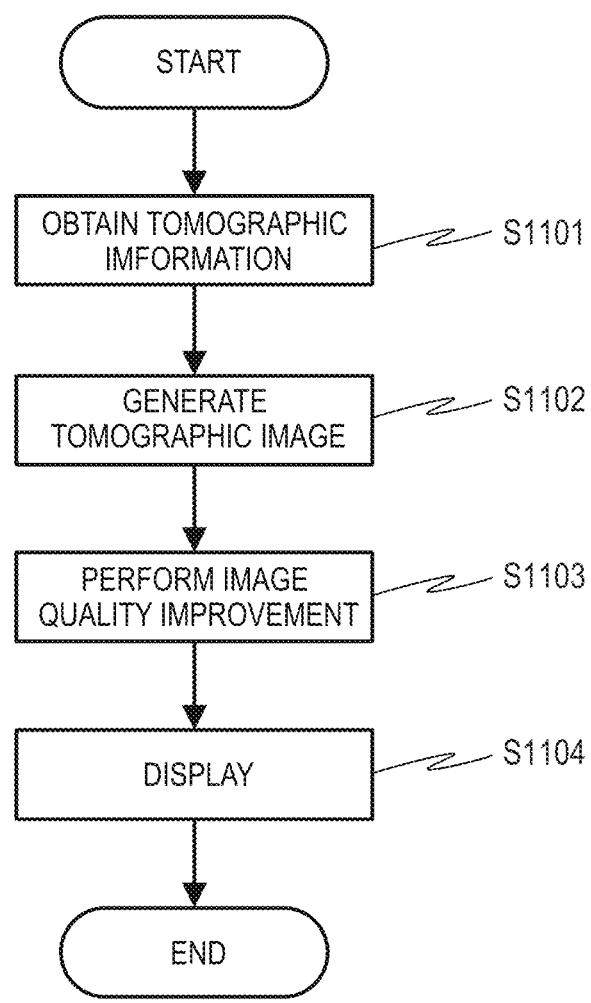
FIG. 11 is a flowchart of a series of image processing operations according to Embodiment 1.

Next, a series of image processing operations according to the present embodiment will be described referring to FIG. 11. FIG. 11 is a flowchart of the series of image processing operations according to the present embodiment.

First, in step S1101, the obtaining unit 310 obtains tomographic information that was obtained by imaging the eye to be examined E. The obtaining unit 310 may obtain the tomographic information of the eye to be examined E using the imaging unit 20, or may obtain the tomographic information from the storage 340 or another apparatus that is connected to the controlling unit 30.

In the case of obtaining tomographic information of the eye to be examined E using the imaging unit 20, scanning of the eye to be examined E can be started after selecting the imaging mode and performing setting and adjustment of various imaging parameters such as the scan pattern, scanning range, focus, and fixation lamp position.

In step S1102, the tomographic image generating unit 321 generates a tomographic image based on the obtained tomographic information of the eye to be examined E. Note that, in a case where, in step S1101, the obtaining unit 310 obtains a tomographic image from the storage 340 or another apparatus that is connected to the controlling unit 30, step S1102 can be omitted.

In step S1103, the image quality improving unit 322 generates a high quality tomographic image that seems to be an image for which different image processing is performed on each region based on the tomographic image generated in step S1102 or the tomographic image obtained in step S1101, by using the learned model.

Note that, in a case where the learned model performed learning in a manner in which images are divided into regions, the image quality improving unit 322 first divides the tomographic image that is the input image into a rectangular region image group based on the image size at the time of learning, and inputs the group of divided rectangular region images into the learned model. Thereafter, the image quality improving unit 322 arranges the respective images of a group of rectangular region images that are high quality tomographic images obtained using the learned model according to the same positional relationship as that of the respective images of the rectangular region image group that was input to the learned model, and combines the rectangular region images to thereby generate a final high quality tomographic image.

In step S1104, the display controlling unit 350 causes the high quality tomographic image generated in step S1103 to be displayed on the display unit 50. When the display processing by the display controlling unit 350 ends, the series of image processing operations ends.

According to such processing, a high quality tomographic image that seems to be an image for which different image processing has been performed on different regions using a learned model can be generated and displayed. Particularly, in the present embodiment, even with respect to a diseased eye or the like, an image suitable for comprehensive observation in which the contrast of the vitreous body, the choroid and the retina is enhanced can be generated and displayed.

As described above, the controlling unit 30 according to the present embodiment includes the obtaining unit 310 and the image quality improving unit 322. The obtaining unit 310 obtains a first tomographic image (tomographic image obtained utilizing light interference) of the eye to be examined E that is the object under examination. The image quality improving unit 322 uses a learned model to generate, from the first tomographic image (first medical image), a second tomographic image (second medical image) that seems to be an image for which different image processing is performed on different regions in the first tomographic image. Further, in the present embodiment, the training data of the learned model includes a tomographic image for which gradation conversion processing was performed according to the regions of the eye to be examined E.

According to the foregoing configuration, a high quality tomographic image that seems to be an image for which different image processing was performed for different regions using a learned model can be generated and displayed. Particularly, in the present embodiment, with respect to a diseased eye or the like, even in a case where a favorable result cannot be obtained by segmentation of a tomographic image, a display image with which it is possible to observe the internal structure of the retina, the vitreous body and the choroid in detail can be obtained.

Further, in the present embodiment, the image quality improving unit 322 can generate a high quality tomographic image in which the image quality of each region has been improved using the learned model. Therefore, the image quality improving unit 322 can generate, from a first tomographic image, a second tomographic image in which the image quality of different regions of a first region in the first tomographic image and a second region that is different from the first region has been improved using the learned model. Here, for example, the first region may be a region of a retina portion, and the second region may be a region of a vitreous body portion. Further, the number of regions for which image quality improving is performed is not limited to two, and may be three or more. In this case, for example, a third region which is different from the first and second regions and which is subjected to image quality improving may be a region of a choroid portion. Note that, the respective regions subjected to image quality improving may be arbitrarily changed according to a desired configuration. From this viewpoint also, the controlling unit 30 according to the present embodiment can generate an image that seems to be an image for which appropriate image processing has been performed for each region that is an observation target.

Although in the learned model according to the present embodiment an image for which gradation conversion processing that is appropriate for each region has been performed is used as output data of the training data, the training data is not limited thereto. For example, a high quality image obtained by performing, for each region of a tomographic image, averaging processing such as arithmetic averaging or maximum a posteriori processing (MAP estimation processing) with respect to a source image group may be used as output data of the training data. Here, the term "source image" refers to a tomographic image serving as input data.

In the MAP estimation processing, a likelihood function is obtained based on the probability density of each pixel value in a plurality of images, and a true signal value (pixel value) is estimated using the obtained likelihood function. A high quality image obtained by the MAP estimation processing is a high contrast image that is based on pixel values that are close to the true signal values. Further, since the estimated signal values are determined based on the probability density, randomly generated noise is reduced in a high quality image obtained by the MAP estimation processing. Therefore, by using a learned model that performed learning using a high quality image obtained by the MAP estimation processing as training data, a high quality image that is suitable for image diagnosis in which noise is reduced and which has high contrast can be generated from an input image. Note that, with regard to the method for generating a pair of input data and output data of the training data, a method that is similar to a case where an averaged image is used as training data may be performed.

Further, as output data of the training data, a high quality image obtained by applying smoothing filter processing that uses a mean value filter or the like to a source image may be used. In this case, by using the learned model, a high quality image in which random noise is reduced can be generated from an input image. Note that, with regard to the method for generating a pair of input data and output data of the training data, a method that is similar to a case where an image on which gradation conversion processing was performed is used as training data may be performed.

Note that, an image obtained from an imaging apparatus having the same image quality tendency as the imaging unit 20 may be used as the input data of the training data. Further, as the output data of the training data, a high quality image obtained by high-cost processing such as processing using the method of successive approximation may be used, or a high quality image obtained by imaging an object under examination that corresponds to the input data using an imaging apparatus with higher performance than the imaging unit 20 may be used. In addition, a high quality image obtained by performing rule-based noise reduction processing that is based on the structure of the object under examination or the like may be used as the output data. Here, the noise reduction processing can include, for example, processing that replaces a high intensity pixel that is only one pixel which is clearly noise that appears in a low intensity region with the average value of neighboring low-intensity pixel values. Thus, an image imaged by an imaging apparatus with higher performance than the imaging apparatus used to image an input image, or an image obtained by an imaging process that involves a greater number of steps than the imaging process used to obtain the input image may be used as training data that is used for learning by the learned model.

In addition, the output data of the training data may be an image that was subjected to the averaging processing, the MAP estimation processing or the like as described above, or may be an image obtained by performing different gradation conversion processing for each region that is an observation target with respect to an image imaged by an imaging apparatus with higher performance than the imaging unit 20. Accordingly, the output data of the training data may be a tomographic image that was generated using a combination of gradation conversion processing that differs for each region that is an observation target, and a tomographic image obtained by performing other processing relating to image quality improving or by imaging using a high-performance imaging apparatus. In this case, a tomographic image that is more suitable for diagnosis can be generated and displayed.

Further, although in the present embodiment an original tomographic image is adopted as input data, the input data is not limited thereto. For example, a tomographic image subjected to gradation conversion so that a retina portion is easy to observe or a tomographic image subjected to gradation conversion so that a vitreous body portion and a choroid portion are easy to observe may be adopted as input data. In this case, the image quality improving unit 322 can input, to the learned model, a tomographic image subjected to gradation conversion so as to make the retina portion or the vitreous body portion and the choroid portion easy to observe that corresponds to the input data of the training data, and can thereby generate a high quality tomographic image.

In addition, data with a high dynamic range which was adjusted to be data that allows appropriate gradation conversion to be easily performed for each region may be adopted as the output data. In this case, the image quality improving unit 322 can generate a high quality tomographic image by performing appropriate gradation conversion on data with a high dynamic range obtained using the learned model.

Note that, although it has been described that the image quality improving unit 322 generates a high quality image for which appropriate gradation conversion with respect to displaying by the display unit 50 has been performed using a learned model, image quality improving processing by the image quality improving unit 322 is not limited thereto. It suffices that the image quality improving unit 322 can generate an image with image quality that is more suitable for image diagnosis.

In a tomographic image obtained using a learned model, a case can also occur in which, depending on the learning tendency, tissue such as a blood vessel that does not actually exist is visualized or tissue that should be present is not visualized. Therefore, when displaying a high quality tomographic image obtained using a learned model, the display controlling unit 350 may also display information on the effect that the image is a tomographic image that was obtained using a learned model. In this case, the occurrence of a misdiagnosis by the operator can be suppressed. Note that, the display form may be any form as long as the form is such that it can be understood that the image is an image obtained using a learned model.

(Modification 1)

In Embodiment 1, a case has been described in which an image of a partial region (rectangular region) of a tomographic image that was subjected to gradation conversion processing so that comprehensive observation can be performed is used as the output data of training data. In contrast, in Modification 1, tomographic images that differ for each region that is an observation target are used as output data of the training data. Hereunder, training data in the present modification is described referring to FIG. 12A to FIG. 12C. Note that, since the components and processing operations except the training data of the machine learning model according to the present modification are the same as in Embodiment 1, such components and processing operations are denoted by the same reference characters as in Embodiment 1 and a description thereof is omitted hereunder.

Figure 12A:
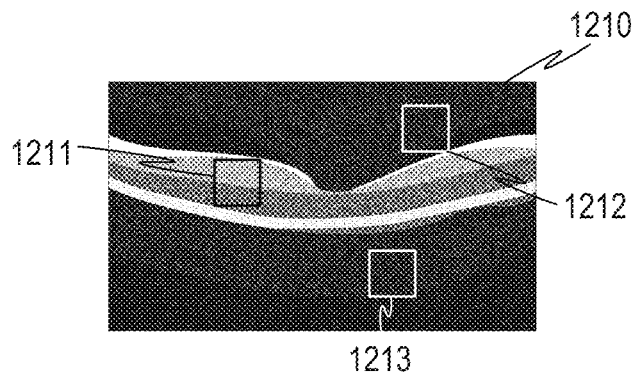
FIG. 12A is a view illustrating a different example of the training data.

FIG. 12A illustrates one example of an original tomographic image 1210 pertaining to input data of training data. In FIG. 12A, a rectangular region image 1212 of a region of a vitreous body portion, a rectangular region image 1211 of a region of a retina portion, and a rectangular region image 1213 of a region of a choroid portion are illustrated.

Figure 12B:
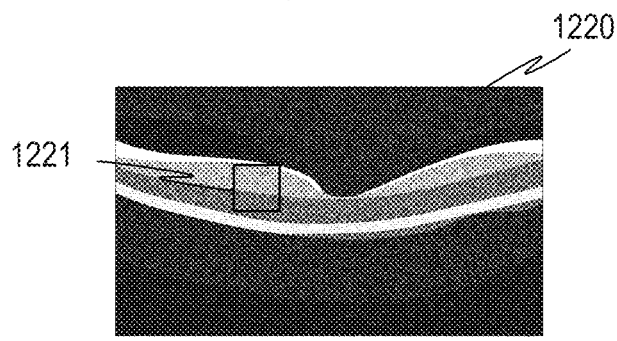
FIG. 12B is a view illustrating a different example of the training data.

FIG. 12B illustrates a tomographic image 1220 obtained by performing gradation conversion processing so as to ensure the contrast of the region of the retina portion with respect to the original tomographic image 1210. In FIG. 12B, a rectangular region image 1221 that has a corresponding positional relationship with the rectangular region image 1211 of the region of the retina portion is illustrated.

Figure 12C:
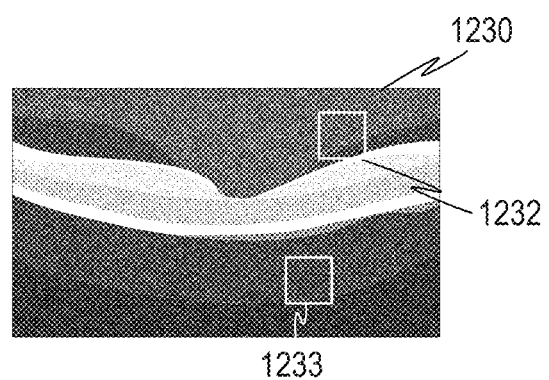
FIG. 12C is a view illustrating a different example of the training data.

FIG. 12C illustrates a tomographic image 1230 obtained by performing gradation conversion processing so as to ensure the contrast of the regions of the vitreous body portion and the choroid portion with respect to the original tomographic image 1210. In FIG. 12C, a rectangular region image 1232 that has a corresponding positional relationship with the rectangular region image 1212 of the region of the vitreous body portion, and a rectangular region image 1233 that has a corresponding positional relationship with the rectangular region image 1213 of the region of the choroid portion are illustrated.

In the present modification, one pair of training data is created by adopting the rectangular region image 1211 of the region of the retina portion in the original tomographic image 1210 as input data, and adopting the rectangular region image 1211 of the region of the retina portion in the tomographic image 1220 as output data. Similarly, one pair of training data is created by adopting the rectangular region image 1212 of the region of the vitreous body portion in the original tomographic image 1210 as input data, and adopting the rectangular region image 1232 of the region of the vitreous body portion in the tomographic image 1230 as output data. Further, one pair of training data is created by adopting the rectangular region image 1213 of the region of the choroid portion in the original tomographic image 1210 as input data, and adopting the rectangular region image 1233 of the region of the choroid portion in the tomographic image 1230 as output data.

In such a case also, a tomographic image obtained by performing appropriate gradation conversion processing for each region that is an observation target can be used as output data of the training data. Therefore, similarly to Embodiment 1, the image quality improving unit 322 can use a learned model that performed learning using such training data to generate a high quality tomographic image that seems to be an image for which different image processing was performed for each region that is an observation target.

(Modification 2)

In Embodiment 1, training data of a machine learning model is used in which a tomographic image obtained by subjecting an original tomographic image to image quality improving processing such as gradation conversion processing regardless of the imaging mode is adopted as output data. In this regard, in an OCT apparatus, the tendency with respect to the strength or weakness of the signal intensity in a tomographic image differs depending on the imaging mode. Therefore, in Modification 2, for each region that is an observation target, a tomographic image obtained in an imaging mode in which there is a tendency for the signal intensity to be high with respect to the relevant region is used as output data of the training data.

Hereunder, the training data according to the present modification is described referring to FIG. 13A to FIG. 15C. Note that, since the components and processing operations except the training data of the machine learning model according to the present modification are the same as in Embodiment 1, such components and processing operations are denoted by the same reference characters as in Embodiment 1 and a description thereof is omitted hereunder. First, imaging methods in a vitreous body mode and a choroid mode will be described as imaging methods for respective imaging modes of the OCT apparatus 1.

(Imaging Method In Vitreous Body Mode)

Figure 13A:
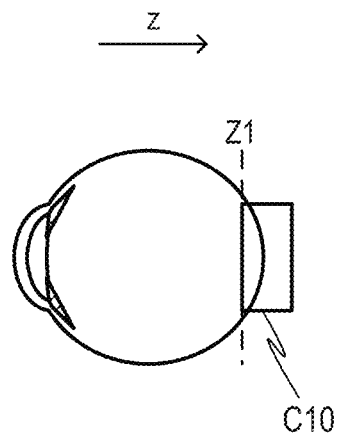
FIG. 13A is an explanatory drawing for describing imaging in a vitreous body mode.
Figure 13B:
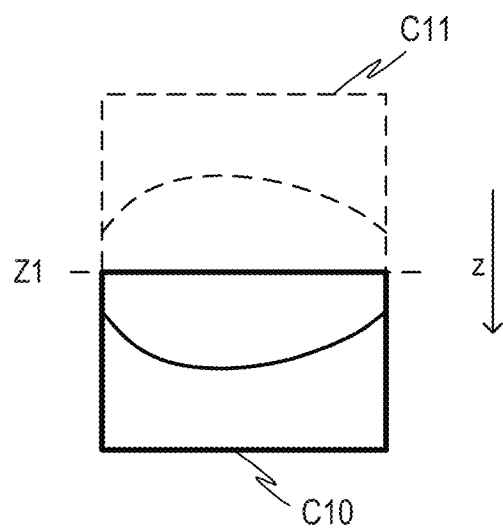
FIG. 13B is an explanatory drawing for describing imaging in the vitreous body mode.
Figure 13C:
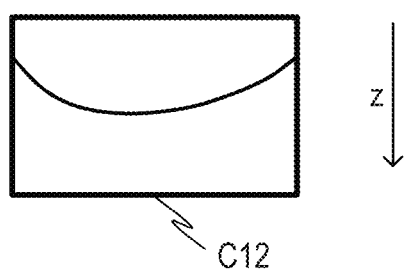
FIG. 13C is an explanatory drawing for describing imaging in the vitreous body mode.

Referring to FIG. 13A to FIG. 13C, an imaging method in a vitreous body mode of the OCT apparatus 1 will be described. In the vitreous body mode, as illustrated in FIG. 13A, the reference mirror 221 is moved so that a position Z1 in the depth direction (Z-axis direction) at which the optical path lengths of the reference light and the measuring light match is located on the shallow side (vitreous body side) in the depth direction of an imaging range C10, and imaging is performed.

In this case, as illustrated in FIG. 13B, with respect to the position Z1, a normal image is obtained in the imaging range C10 in a positive direction in the Z-direction, and a virtual image is obtained in an imaging range C11 in a negative direction. Imaging in the vitreous body mode of an OCT apparatus is generally performed by obtaining a normal image of the imaging range C10 as a tomographic image. A tomographic image C12 that is one example of a tomographic image obtained in the vitreous body mode is illustrated in FIG. 13C. Note that, a virtual image on the imaging range C11 side can also be obtained as the tomographic image C12. In a case where a virtual image on the imaging range C11 side is obtained as the tomographic image C12, the image may be vertically inverted and displayed.

In an OCT apparatus, the closer a region is to a position in the depth direction at which the optical path lengths of the reference light and the measuring light match, the higher the signal intensity obtained with respect to the relevant region becomes. Therefore, in the tomographic image C12 imaged in the vitreous body mode, the signal intensity on the side closer to the position Z1, that is, the vitreous body side, will be high.

(Imaging Method in Choroid Mode)

Figure 14A:
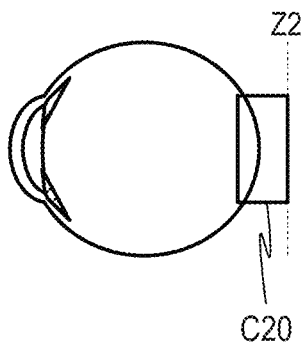
FIG. 14A is an explanatory drawing for describing imaging in a choroid mode.

Next, referring to FIG. 14A to FIG. 14C, an imaging method in a choroid mode of the OCT apparatus will be described. In the choroid mode, as illustrated in FIG. 14A, the reference mirror 221 is moved so that a position Z2 in the depth direction at which the optical path lengths of the reference light and the measuring light match is located on the deep side (choroid side) in the depth direction of the imaging range, and imaging is performed.

Figure 14B:
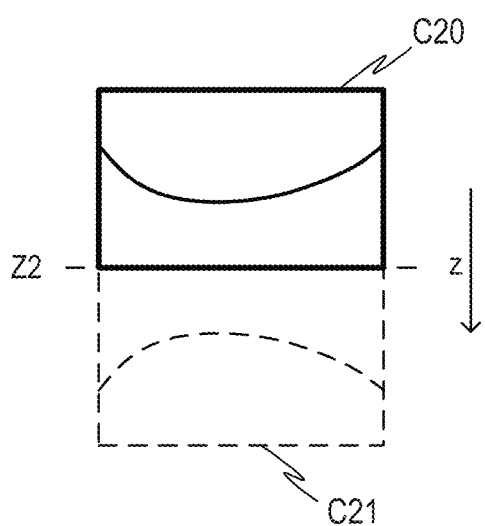
FIG. 14B is an explanatory drawing for describing imaging in the choroid mode.
Figure 14C:
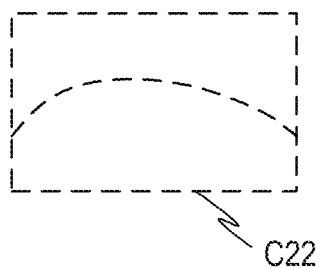
FIG. 14C is an explanatory drawing for describing imaging in the choroid mode.

In this case, as illustrated in FIG. 14B, with respect to the position Z2, a normal image is obtained in an imaging range C20 in the negative direction in the Z-direction, and a virtual image is obtained in an imaging range C21 in the positive direction. Imaging in the choroid mode of an OCT apparatus is generally performed by obtaining a virtual image on the imaging range C21 side as a tomographic image. A tomographic image C22 that is one example of a tomographic image obtained in the choroid mode is illustrated in FIG. 14C. Note that, a normal image on the imaging range C20 side can also be obtained as the tomographic image C22. Further, in a case where a virtual image on the imaging range C21 side is obtained as the tomographic image C22, the image may be inverted vertically and displayed.

As described above, in an OCT apparatus, the closer a region is to a position in the depth direction at which the optical path lengths of the reference light and the measuring light match, the higher the signal intensity obtained with respect to the relevant region becomes. Therefore, in the tomographic image C22 imaged in the choroid mode, the signal intensity on the side closer to the position Z2, that is, the choroid side, will be high.

In view of such characteristics of OCT apparatuses, in the present modification, in accordance with the region that is the observation target, a tomographic image obtained in an imaging mode having a tendency such that the signal intensity of the relevant region, in particular, is high is used as output data of the training data of the machine learning model. More specifically, in the OCT apparatus, the signal intensity on the vitreous body side will be high in a tomographic image imaged in the vitreous body mode, and the signal intensity on the choroid side will be high in a tomographic image imaged in the choroid mode. Therefore, the same site of the same eye to be examined is imaged in the choroid mode and the vitreous body mode, and for each partial region image (rectangular region image) of the input data, a tomographic image in which the signal intensity of the corresponding partial region is high is used as output data. In other words, in the present modification, the training data of the learned model includes a medical image which is obtained by imaging an object under examination and which is obtained in an imaging mode corresponding to any of the different regions in the relevant medical image.

Figure 15A:
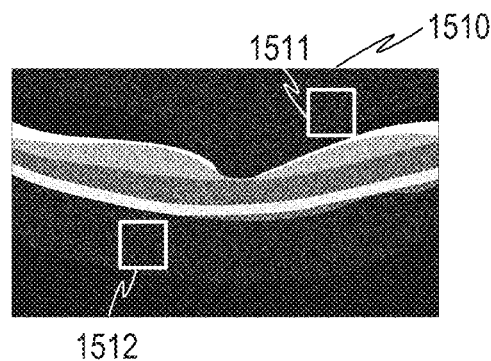
FIG. 15A is a view illustrating a different example of the training data.

FIG. 15A illustrates one example of an original tomographic image 1510 pertaining to input data of training data, that was imaged in the vitreous body mode. In FIG. 15A, a rectangular region image 1511 of a region of a vitreous body portion, and a rectangular region image 1512 of a region of a choroid portion are illustrated.

Figure 15B:
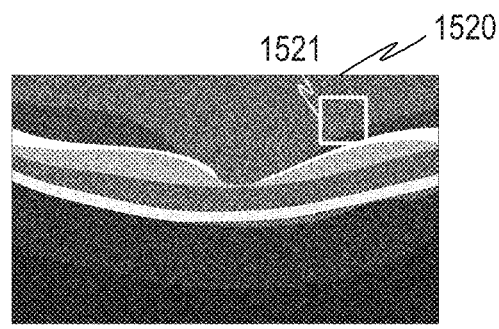
FIG. 15B is a view illustrating a different example of the training data.

FIG. 15B illustrates a tomographic image 1520 obtained by performing gradation conversion processing so as to ensure the contrast of regions of a retina portion, a vitreous body portion and a choroid portion with respect to tomographic image obtained by imaging the same site of the same eye to be examined in the vitreous body mode. Further, in FIG. 15B, a rectangular region image 1521 that has a corresponding positional relationship with the rectangular region image 1511 of the region of the vitreous body portion is illustrated.

Figure 15C:
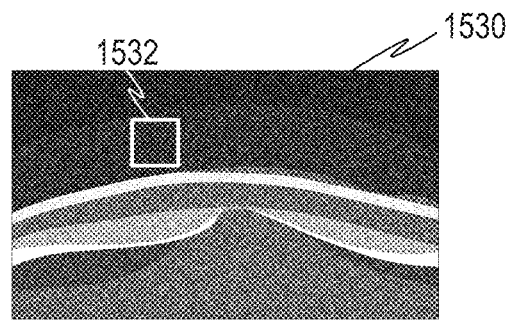
FIG. 15C is a view illustrating a different example of the training data.

FIG. 15C illustrates a tomographic image 1530 obtained by performing gradation conversion processing so as to ensure the contrast of regions of a retina portion, a vitreous body portion and a choroid portion with respect to tomographic image obtained by imaging the same site of the same eye to be examined in the choroid mode. Further, in FIG. 15C, a rectangular region image 1532 that has a corresponding positional relationship with the rectangular region image 1512 of the region of the choroid portion is illustrated.

In the present modification, one pair of training data is created by adopting the rectangular region image 1511 of the region of the vitreous body portion in the original tomographic image 1510 as input data, and adopting the rectangular region image 1521 of the region of the vitreous body in the tomographic image 1520 as output data. Similarly, one pair of training data is created by adopting the rectangular region image 1512 of the region of the choroid portion in the original tomographic image 1510 as input data, and adopting the rectangular region image 1532 of the region of the choroid portion in the tomographic image 1530 as output data. Note that, in the present modification, because the tomographic image 1530 imaged in the choroid mode is inverted vertically relative to the original tomographic image 1510 pertaining to the input data, a rectangular region image obtained by vertically inverting the rectangular region image 1532 is used as output data of the training data.

In such a case, with respect to a tomographic image obtained in an imaging mode in accordance with a region that is an observation target which is an imaging mode that has a tendency such that the signal intensity of the relevant region in particular is high, a tomographic image obtained by subjecting the relevant tomographic image to gradation conversion processing according to the region can be used as output data of the training data. In other words, the training data of the learned model can include a medical image which is obtained by imaging an object under examination and which is a medical image obtained by subjecting the medical image obtained in an imaging mode corresponding to any of the different regions in the relevant medical image to gradation conversion processing that corresponds to any of the different regions in the relevant medical image. By using a learned model that performed learning by means of such training data, the image quality improving unit 322 can generate a tomographic image that seems to be an image for which the image quality has been improved further for each region that is an observation target.

Note that, the input data of the training data is not limited to an original tomographic image that was imaged in the vitreous body mode, and may be an original tomographic image that was imaged in the choroid mode. In this case, because the tomographic image imaged in the vitreous body mode is inverted vertically relative to the original tomographic image pertaining to the input data, an image obtained by vertically inverting the rectangular region image pertaining to the tomographic image imaged in the vitreous body mode is used as output data of the training data.

Further, the gradation conversion processing applied to tomographic images imaged in the respective imaging modes is not limited to gradation conversion processing for ensuring the contrast of regions of a retina portion, a vitreous body portion and a choroid portion so that a comprehensive observation can be performed. For example, similarly to Modification 1, a tomographic image obtained by subjecting a tomographic image imaged in the vitreous body mode to gradation conversion for ensuring the contrast of the region of the vitreous body portion may be used as output data of the training data. Likewise, a tomographic image obtained by subjecting a tomographic image imaged in the choroid mode to gradation conversion for ensuring the contrast of the region of the choroid portion may be used as output data of the training data.

Note that, output data based on a tomographic image imaged in the vitreous body mode or output data based on a tomographic image imaged in the choroid mode may be used as output data of the training data that relates to the region of the retina portion. Further, the imaging modes are not limited to a vitreous body mode and a choroid mode, and may be arbitrarily set according to a desired configuration. In this case also, based on the tendency with respect to the strength or weakness of the signal intensity in a tomographic image according to the imaging mode, for each region that is an observation target, a tomographic image having a tendency such that the signal intensity of the relevant region is high can be used as output data of the training data.

Further, in Modification 1 and 2 also, similarly to Embodiment 1, the input data of the training data is not limited to an original tomographic image, and may be a tomographic image that was subjected to arbitrary gradation conversion. Further, the output data of the training data is not limited to a tomographic image that was subjected to gradation conversion, and may be a tomographic image obtained by performing an adjustment with respect to an original tomographic image so that gradation conversion can be easily performed.

(Modification 3)

In Embodiment 1, the image quality improving unit 322 uses one learned model to generate a high quality image that seems to be an image for which different image processing for each region of the target image. In contrast, according to Modification 3, firstly, with respect to a tomographic image that is the input data, the image quality improving unit 322 generates a label image for which labeling (annotation) of regions has been performed for each pixel using a first learned model. Thereafter, with respect to the generated label image, the image quality improving unit 322 generates a high quality image that seems to be an image for which image processing has been performed according to each region using a second learned model that is different from the first learned model. In other words, from a tomographic image (first medical image) that is the input data, the image quality improving unit 322 generates a label image in which different label values are given to different regions using a learned model that is different from a learned model for generating a high quality image (second medical image). Further, the image quality improving unit 322 generates a high quality image from the label image by using a learned model for generating a high quality image (second medical image).

In the present modification, with regard to the first learned model, learning is performed using training data in which a tomographic image is adopted as input data, and a label image in which labeling of regions has been performed for each pixel of the tomographic image is adopted as output data. Note that, with regard to the label image, an image that was appropriately processed by conventional segmentation processing may be used, or a label image that was manually labeled may be used. The labels may be, for example, a vitreous body label, a retina label, a choroid label and the like. Note that, the labels may be displayed using a character string, or may be numerical values corresponding to each region that are set in advance. Further, the labels are not limited to the aforementioned examples, and may indicate arbitrary regions according to a desired configuration.

Further, with regard to the second learned model, learning is performed using training data in which a label image is adopted as input data, and a tomographic image obtained by subjecting the relevant label image to image quality improving processing according to the label of each pixel is adopted as output data. Note that, with regard to the image quality improving processing according to the label of each pixel, as mentioned above, the image quality improving processing can include gradation conversion processing according to the region that is the observation target and the like.

In such a case, similarly to Embodiment 1, the image quality improving unit 322 can generate a high quality tomographic image that seems to be an image for which different image processing has been performed for each region that is an observation target using the first and second learned models. Further, a learned model outputs output data which has a high probability of corresponding to the input data according to a learning tendency. In this regard, when the learned model performs learning using a group of images having a similar image quality tendency to each other as training data, an image that underwent image quality improving more effectively can be output with respect to an image that has the similar tendency in question. Therefore, by using a learned model that used training data which was labeled for each region as in the present modification, it can be expected that an image that underwent image quality improving more effectively will be generated.

Note that, with respect to the training data pertaining to the present modification also, similarly to Embodiment 1, an entire image may be used or a rectangular region image (partial image) may be used. Further, according to a desired configuration, the input data and the output data may be images after arbitrary gradation conversion or may be images before gradation conversion.

(Modification 4)

In Embodiment 1, a case was described in which the image quality improving unit 322 integrates partial images of a tomographic image obtained using a learned model to thereby generate a final high quality tomographic image. In particular, in the example described in Embodiment 1, the partial images obtained using a learned model are images that seems to be images for which different gradation conversion processing was performed for each region that is an observation target, in accordance with the learning tendency. Therefore, if the partial images are simply integrated, in some cases the distribution of intensities will be markedly different between a location where different regions come in contact (connecting portion) and a location of a region adjacent to such a location (for example, a region of a vitreous body portion or a region of a retina portion), and image edges will be conspicuous.

Therefore, in Modification 4, when integrating partial images obtained using a learned model, the image quality improving unit 322 modifies pixel values of connecting portions of regions that are observation targets based on pixel values of the surrounding pixels so that the image edges become inconspicuous. By this means, an image that is suitable for diagnosis in which a sense of incongruity caused by image edges is reduced can be generated.

In this case, with respect to a connecting portion of a region that is an observation target, the image quality improving unit 322 can modify intensity values by performing any known blending processing. Note that, the image quality improving unit 322 may also perform blending processing with respect to a location that is adjacent to a connecting portion of a region that is an observation target. Further, the processing to make image edges inconspicuous is not limited to the blending processing, and may be other arbitrary processing.

Embodiment 2

In Embodiment 1, image quality improving processing using a learned model is performed uniformly with respect to generated/obtained tomographic images. In contrast, in an OCT apparatus according to Embodiment 2, image processing to be applied to a tomographic image is selected according to an instruction of an operator.

Hereunder, the OCT apparatus according to the present embodiment is described referring to FIG. 16 to FIG. 18C. Note that, the configuration other than a controlling unit according to the present embodiment is the same as the configuration of the OCT apparatus 1 according to Embodiment 1, and hence like components are denoted by the same reference numeral as in Embodiment 1, and a description thereof is omitted hereunder. Hereunder, the OCT apparatus according to the present embodiment will be described centering on differences from the OCT apparatus according to Embodiment 1.

Figure 16:
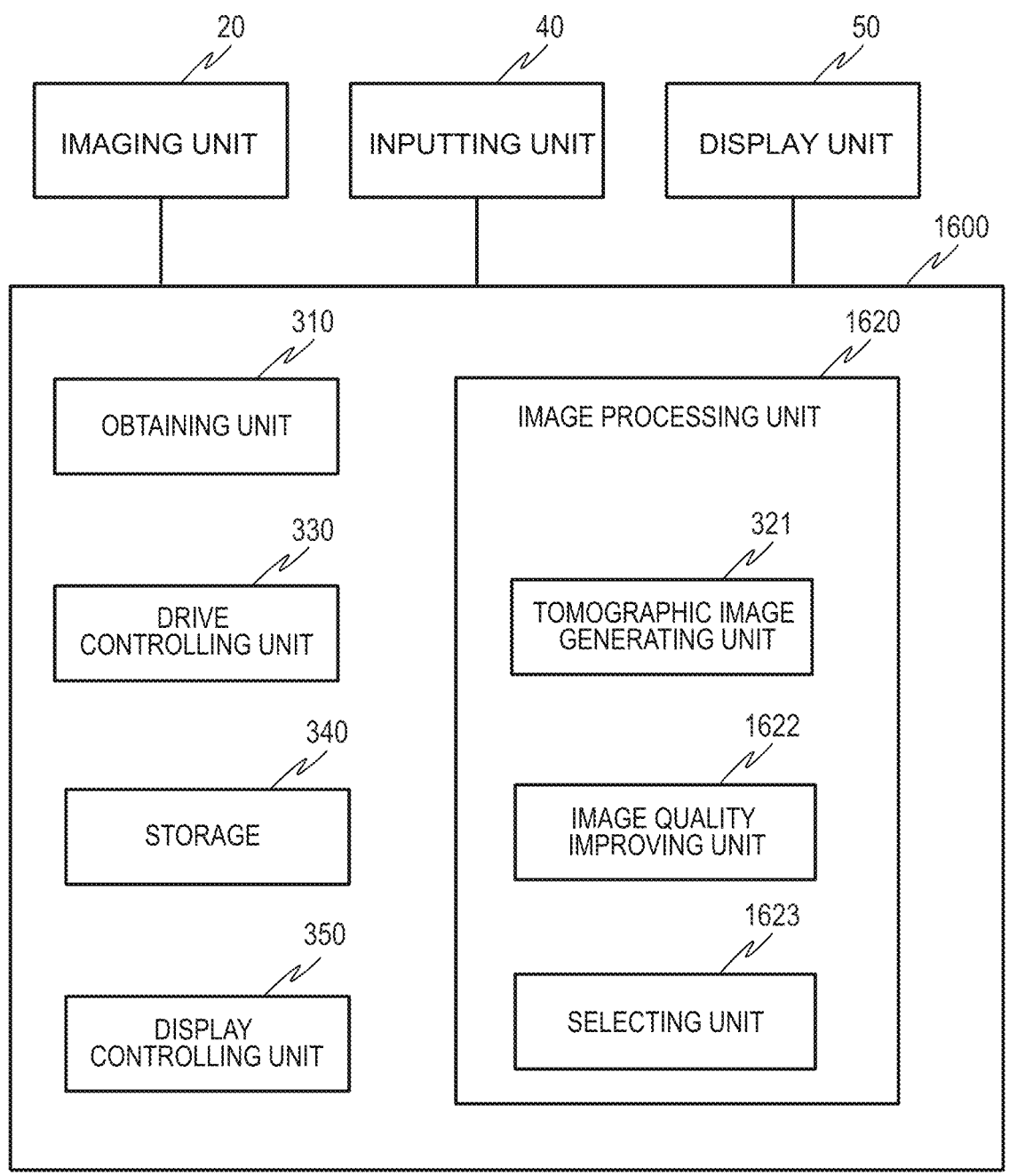
FIG. 16 is a view illustrating a schematic configuration example of a controlling unit according to Embodiment 2.

FIG. 16 illustrates a schematic configuration example of a controlling unit 1600 according to the present embodiment. Note that, in the controlling unit 1600, the configuration other than an image quality improving unit 1622 and a selecting unit 1623 of an image processing unit 1620 is the same as the configuration of the controlling unit 30 according to Embodiment 1, and hence like components are denoted by the same reference numerals as in Embodiment 1, and a description thereof is omitted hereunder.

The image processing unit 1620 includes the image quality improving unit 1622 and the selecting unit 1623, in addition to the tomographic image generating unit 321. The selecting unit 1623 selects image processing to be applied to a tomographic image according to an instruction from the operator that is input through the inputting unit 40.

The image quality improving unit 1622 applies the image processing selected by the selecting unit 1623 to a tomographic image generated by the tomographic image generating unit 321 or a tomographic image obtained by the obtaining unit 310, to thereby generate a high quality tomographic image.

Figure 17:
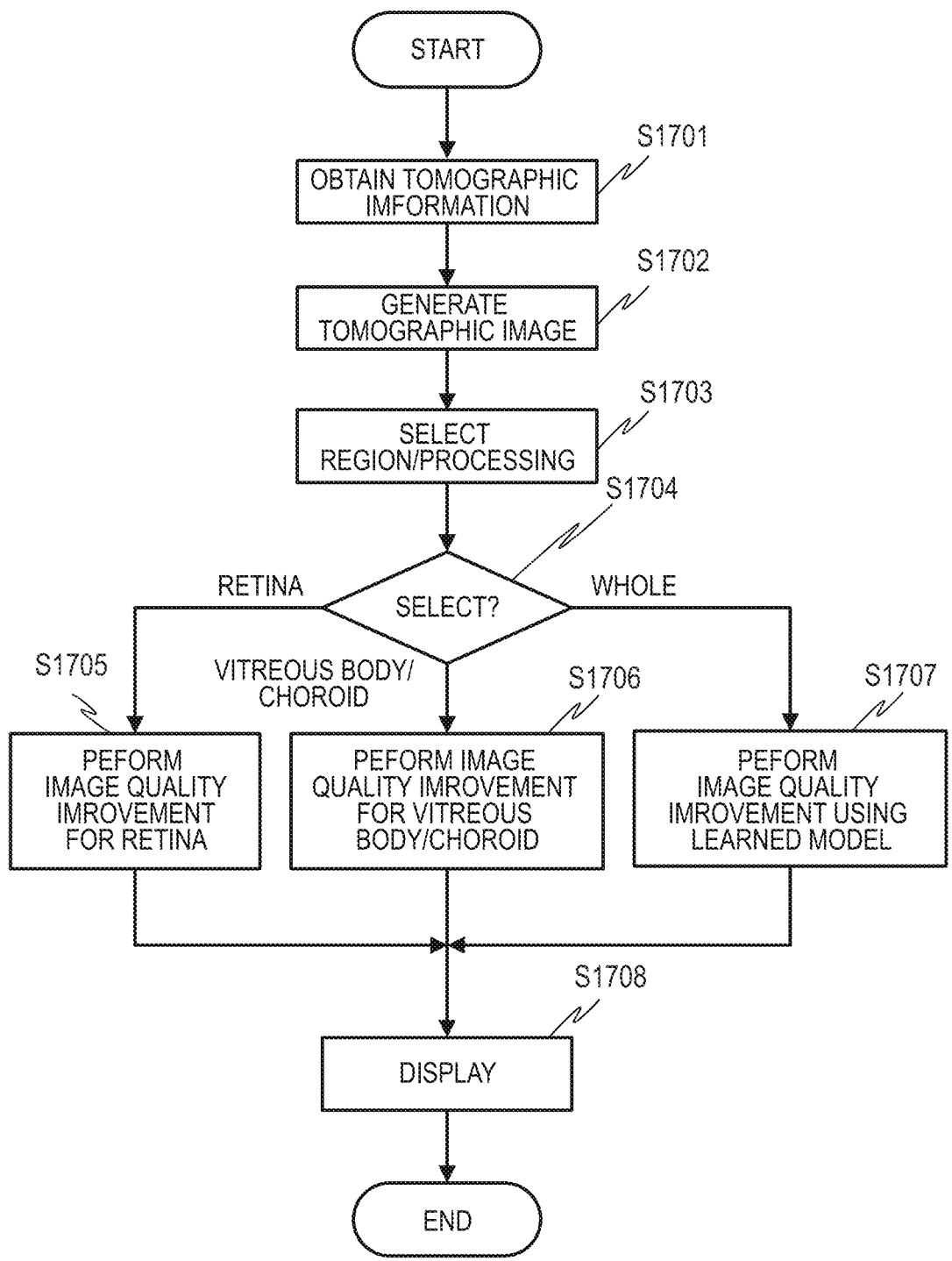
FIG. 17 is a flowchart of a series of image processing operations according to Embodiment 2.

Next, a series of image processing operations according to the present embodiment will be described referring to FIG. 17. FIG. 17 is a flowchart of a series of image processing operations according to the present embodiment. Note that, step S1701 and step S1702 are the same as step S1101 and S1102 according to Embodiment 1, and hence a description of these steps will be omitted here.

Upon the tomographic image generating unit 321 generating an original tomographic image in step S1702, the processing shifts to step S1703. In step S1703, the obtaining unit 310 obtains an instruction from the operator relating to selection of a region it is desired to focus attention on in the tomographic image or processing to be performed with respect to the tomographic image. Note that, at such time, the display controlling unit 350 can cause processing choices to be displayed on the display unit 50 to present the choices to the operator.

In step S1704, the selecting unit 1623 selects the image processing (image quality improving processing) to be applied to the tomographic image according to the instruction from the operator obtained in step S1703. In the present embodiment, according to the instruction from the operator, the selecting unit 1623 selects image quality improving processing with respect to the retina portion, image quality improving processing with respect to the vitreous body/choroid portions, or image quality improving processing with respect to the entire image.

If image quality improving processing with respect to the retina portion is selected in step S1704, the processing shifts to step S1705. In step S1705, the image quality improving unit 1622 subjects the original tomographic image to gradation conversion processing so that the region of the retina portion becomes easy to observe as described above, to thereby generate a high quality tomographic image.

If image quality improving processing with respect to the vitreous body/choroid is selected in step S1704, the processing shifts to step S1706. In step S1706, the image quality improving unit 1622 subjects the original tomographic image to gradation conversion processing so that the regions of the vitreous body portion and the choroid portion become easy to observe as described above, to thereby generate a high quality tomographic image.

If image quality improving processing with respect to the entire image is selected in step S1704, the processing shifts to step S1707. In step S1707, based on the original tomographic image, the image quality improving unit 1622 uses a learned model to generate a high quality tomographic image in which the retina portion, the vitreous body portion and the choroid portion are easy to observe. Note that, the learned model according to the present embodiment is the similar to the learned model according to Embodiment 1, and hence a description regarding the learned model and training data is omitted here.

In step S1708, the display controlling unit 350 causes the high quality tomographic image generated in step S1705, step S1706 or step S1707 to be displayed on the display unit 50. When the display processing by the display controlling unit 350 ends, the series of image processing operations ends.

Figure 18A:
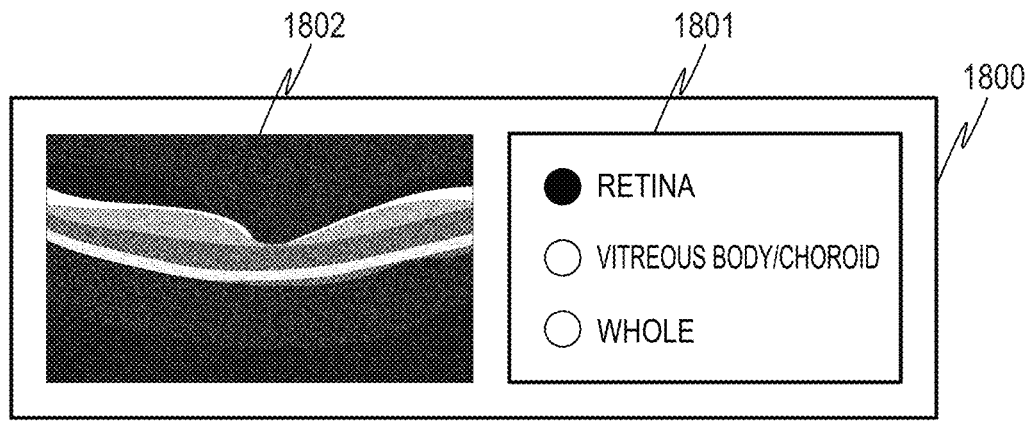
FIG. 18A is a view illustrating an example of a display screen for selecting a region on which it is desired to focus attention.
Figure 18B:
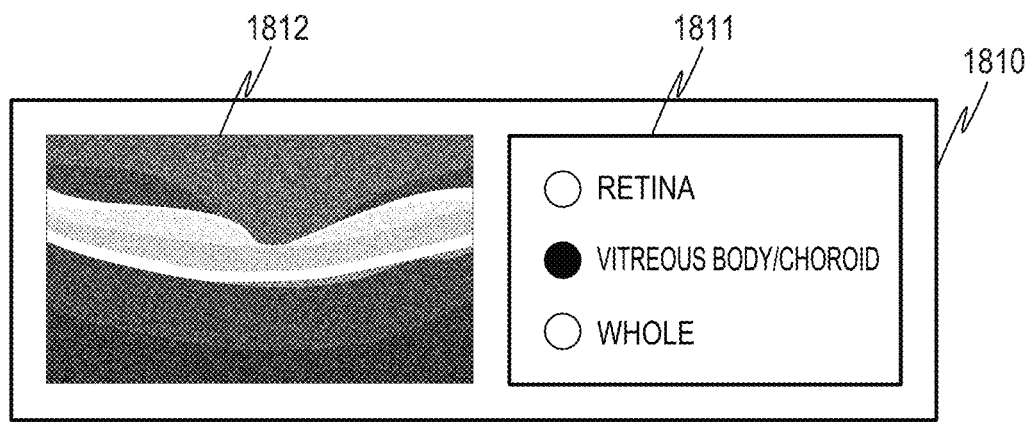
FIG. 18B is a view illustrating an example of a display screen for selecting a region on which it is desired to focus attention.
Figure 18C:
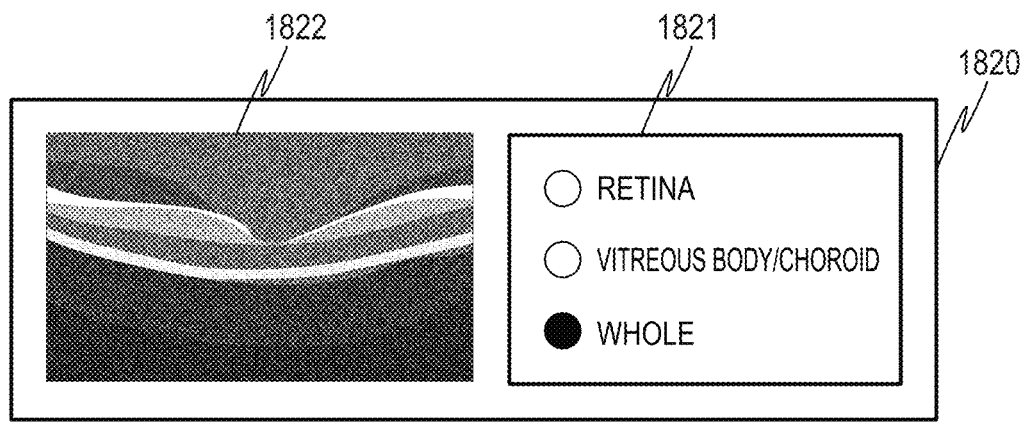
FIG. 18C is a view illustrating an example of a display screen for selecting a region on which it is desired to focus attention.

The operation method according to the present embodiment will now be described referring to FIG. 18A to FIG. 18C. FIG. 18A to FIG. 18C illustrate examples of a display screen that includes choices regarding the region to focus attention on, and a tomographic image which underwent image quality improving processing according to the selected region.

FIG. 18A illustrates a display screen 1800 in a case where the region of the retina portion is selected as the region to focus attention on. On the display screen 1800, choices 1801 and a tomographic image 1802 which underwent gradation conversion processing so that the region of the retina portion became easy to observe are displayed.

In a case where the operator wishes to focus attention on the region of the retina portion, the operator selects "retina" from among the three choices of "retina", "vitreous body/choroid" and "whole" in the choices 1801 through the inputting unit 40. The selecting unit 1623 selects image quality improving processing with respect to the region of the retina portion according to the instruction from the operator, and the image quality improving unit 1622 applies the selected image quality improving processing to the tomographic image to generate the tomographic image 1802 in which the retina portion is easy to observe. The display controlling unit 350 displays the generated tomographic image 1802 in which the retina portion is easy to observe on the display screen 1800.

FIG. 18B illustrates a display screen 1810 in a case where the regions of the vitreous body portion and the choroid portion are selected as regions to focus attention on. On the display screen 1810, choices 1811 and a tomographic image 1812 which underwent gradation conversion processing so that the regions of the vitreous body portion and the choroid portion became easy to observe are displayed.

In a case where the operator wishes to focus attention on the regions of the vitreous body portion and the choroid portion, the operator selects "vitreous body/choroid" from among the three choices of "retina", "vitreous body/choroid" and "whole" in the choices 1801 through the inputting unit 40. The selecting unit 1623 selects image quality improving processing with respect to the regions of the vitreous body portion and the choroid portion according to the instruction from the operator, and the image quality improving unit 1622 applies the selected image quality improving processing to the tomographic image to generate the tomographic image 1812 in which the vitreous body portion and the choroid portion that have high image quality are easy to observe. The display controlling unit 350 displays the generated tomographic image 1812 in which the vitreous body portion and the choroid portion are easy to observe on the display screen 1810.

FIG. 18C illustrates a display screen 1820 in a case where the region of the entire image is selected as the region to focus attention on. On the display screen 1820, choices 1821 and a tomographic image 1822 that seems to be an image which underwent gradation conversion processing so that the region of the entire image became easy to observe are displayed.

In a case where the operator wishes to focus attention on the region of the entire image, the operator selects "whole" from among the three choices of "retina", "vitreous body/choroid" and "whole" in the choices 1821 through the inputting unit 40. The selecting unit 1623 selects image quality improving processing with respect to the entire image according to the instruction from the operator, and the image quality improving unit 1622 applies the selected image quality improving processing to the tomographic image to generate a high quality tomographic image. In this case, the image quality improving unit 1622 generates a high quality tomographic image in which the entire image is easy to observe using the learned model. The display controlling unit 350 displays the generated tomographic image 1822 in which the region of the entire image is easy to observe on the display screen 1820.

As described above, the controlling unit 1600 according to the present embodiment includes the selecting unit 1623 that, according to an instruction from the operator, selects the image processing to be applied to a first tomographic image obtained by the obtaining unit 310. Based on the image processing selected by the selecting unit 1623, the image quality improving unit 1622 generates a third tomographic image (third medical image) by performing gradation conversion processing on the first tomographic image without using the learned model, or generates a second tomographic image from the first tomographic image using the learned model.

According to this configuration, the controlling unit 1600 can generate tomographic images for which different image processing has been performed according to the region that the operator wishes to focus attention on. In particular, as described above, when image quality improving processing using a learned model is performed, in some cases tissue that does not actually exist may be visualized or tissue that originally exists may not be visualized. Therefore, misdiagnosis can be prevented by observing and comparing tomographic images that underwent different image processing.

Further, it is not taken as a premise that gradation conversion processing that is performed so that the region of the retina portion becomes easy to observe or gradation conversion processing that is performed so that the regions of the vitreous body portion and the choroid portion become easy to observe as described above is segmentation processing. Therefore, appropriate image quality improving processing can be expected even with respect to a diseased eye.

In the present embodiment an example has been described in which, after an instruction of the operator regarding the region it is desired to focus attention on is obtained in step S1703, image processing in accordance with the instruction is performed. However, the order of obtaining an instruction from the operator and performing image processing is not limited thereto. The original tomographic image may be subjected to image processing according to each of the choices by the image quality improving unit 1622 beforehand so as to generate the respective high quality tomographic images in advance, and only switching of a high quality tomographic image to be displayed may be performed according to an instruction of the operator. In this case, the selecting unit 1623 can function as a selecting unit for selecting a high quality tomographic image to be displayed.

Further, an instruction from the operator may be obtained after applying image processing (default image processing) that is set in advance to the original tomographic image to generate a high quality tomographic image, and displaying the high quality tomographic image. In this case, if an instruction to perform image processing other than the default image processing is obtained from the operator, a new high quality image generated by performing image processing in accordance with the instruction can be displayed.

Note that, although an example has been described in which the same image processing is performed for the regions of the vitreous body portion and the choroid portion, separate image processing may be performed for the region of the vitreous body portion and the region of the choroid portion.

Furthermore, the image processing is not limited to image quality improving processing with respect to a region of the retina portion, image quality improving processing with respect to regions of the vitreous body portion and the choroid portion, and image quality improving processing using the learned model. For example, as described above, gradation conversion processing so that the regions of the retina portion, the vitreous body portion and the choroid portion become easy to observe that is based on the premise of performing segmentation processing may be included in the image processing choices. In this case, a high quality tomographic image generated by image processing that is based on the premise of performing segmentation processing and a high quality tomographic image generated by image processing using the learned model or the like can be observed and compared. Therefore, the operator can easily determine an erroneous detection caused by segmentation processing, and the authenticity of tissue in a tomographic image that was generated using the learned model.

Embodiment 3

In Embodiment 1, an image subjected to image quality improving processing using a learned model is displayed. In contrast, in the case of an OCT apparatus according to Embodiment 3, image analysis is performed in which a different analysis condition is applied to each of a plurality of regions that are different to each other in a generated high quality tomographic image, and an analysis result is displayed.

Figure 19:
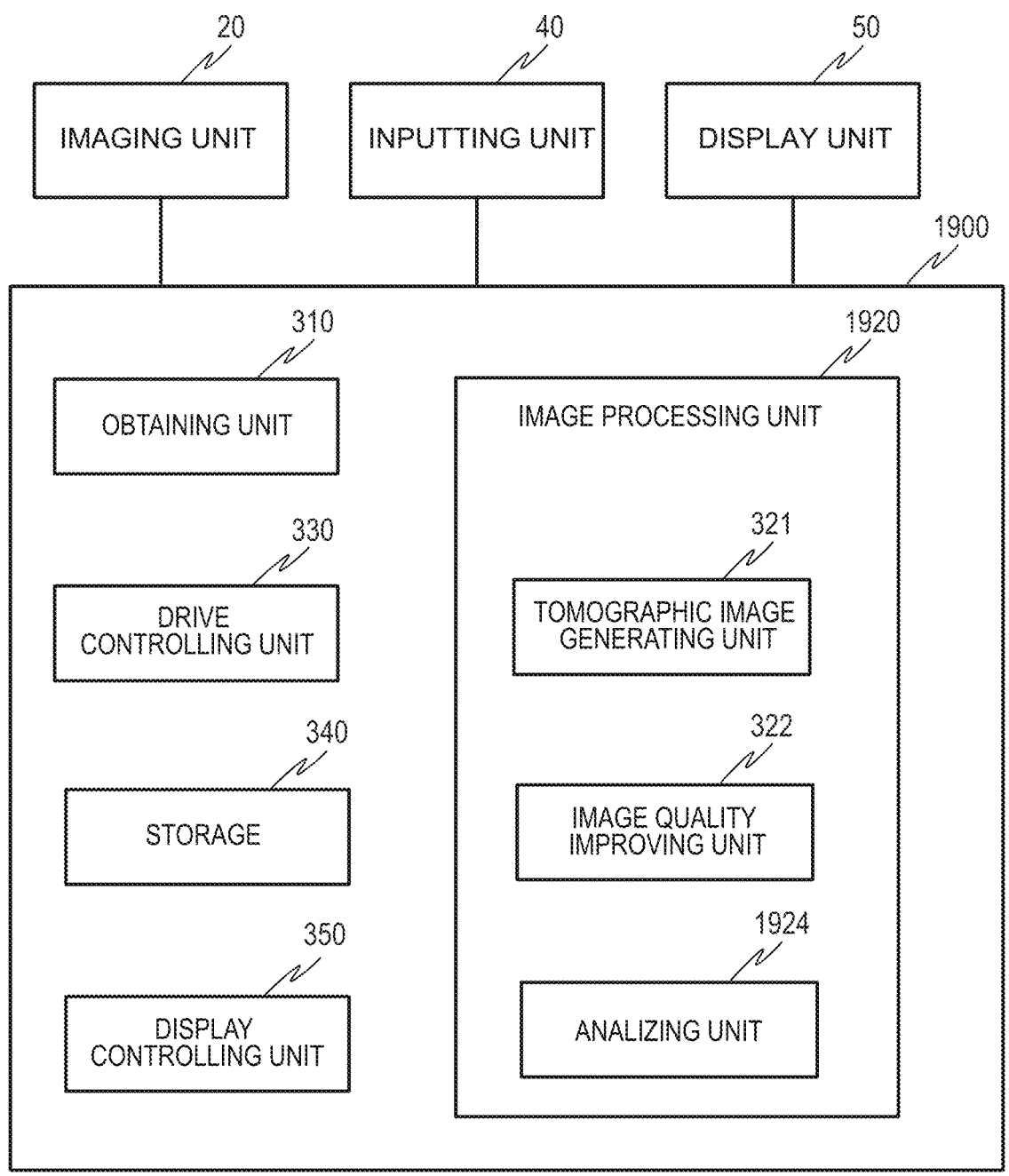
FIG. 19 is a view illustrating a schematic configuration example of a controlling unit according to Embodiment 3.
Figure 20:
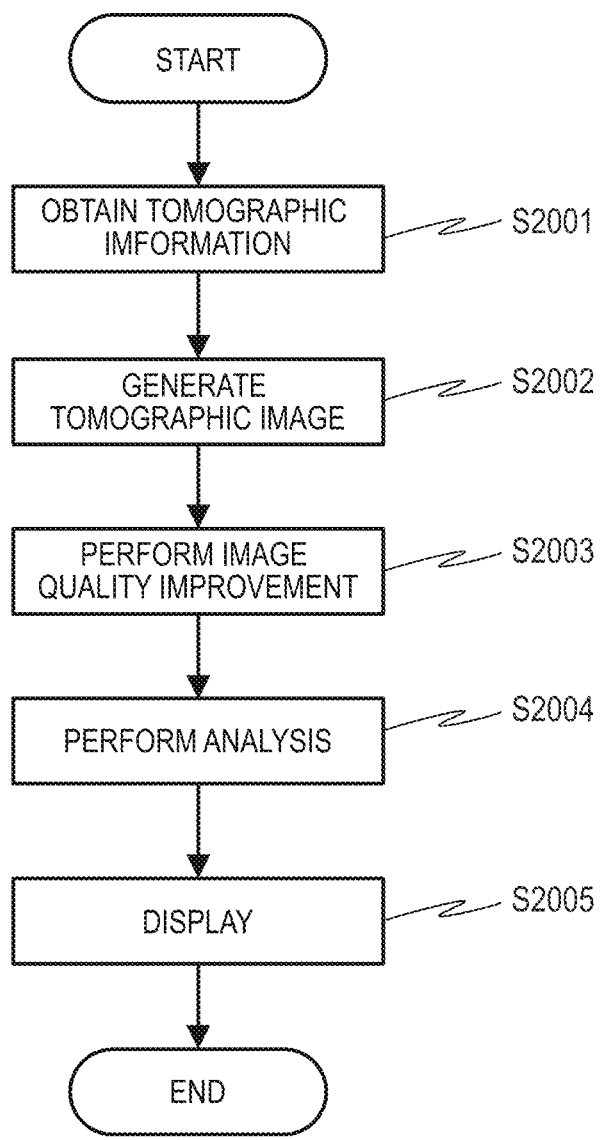
FIG. 20 is a flowchart illustrating a series of image processing operations according to Embodiment 3.

Hereunder, the OCT apparatus according to the present embodiment is described referring to FIG. 19 and FIG. 20. Note that, the configuration other than a controlling unit according to the present embodiment is the same as the configuration of the OCT apparatus 1 according to Embodiment 1, and hence like components are denoted by the same reference numeral as in Embodiment 1, and a description thereof is omitted hereunder. Hereunder, the OCT apparatus according to the present embodiment will be described centering on differences from the OCT apparatus according to Embodiment 1.

FIG. 19 illustrates a schematic configuration example of a controlling unit 1900 according to the present embodiment. Note that, in the controlling unit 1900, the configuration other than an analyzing unit 1924 of an image processing unit 1920 is the same as the configuration of the controlling unit 30 according to Embodiment 1, and hence like components are denoted by the same reference numerals as in Embodiment 1, and a description thereof is omitted hereunder.

The image processing unit 1920 includes the analyzing unit 1924, in addition to the tomographic image generating unit 321 and the image quality improving unit 322. The analyzing unit 1924 subjects a high quality tomographic image generated by the image quality improving unit 322 to image analysis based on an analysis condition that is set for each region. Here, as an analysis condition that is set for each region, for example, layer extraction or blood vessel extraction is set for the region of the retina portion and the region of the choroid portion, and detection of the vitreous body or detachment of the vitreous body is set for the region of the vitreous body portion. Note that, an analysis condition may be set in advance or may be appropriately set by the operator.

In a case where layer extraction is set as an analysis condition, the analyzing unit 1924 performs layer extraction with respect to a region for which the analysis condition in question is set, and can perform layer thickness value measurement or the like with respect to an extracted layer. Further, in a case where blood vessel extraction is set as an analysis condition, the analyzing unit 1924 performs blood vessel extraction with respect to a region for which the analysis condition in question is set, and can perform blood vessel density measurement or the like with respect to an extracted blood vessel. In addition, in a case where detection of the vitreous body or detachment of the vitreous body is set as an analysis condition, the analyzing unit 1924 performs detection of the vitreous body or detachment of the vitreous body with respect to a region for which the analysis condition in question is set. Thereafter, the analyzing unit 1924 can perform quantification with regard to the detected vitreous body or detachment of the vitreous body, and determine a thickness, a width, an area or a volume or the like of the vitreous body or the detachment of the vitreous body.

Note that, the analysis conditions are not limited to the conditions described above, and may be arbitrarily set according to a desired configuration. For example, detection of a fibrous structure of the vitreous body may be set for the region of the vitreous body portion. In this case, the analyzing unit 1924 can perform quantification of the detected fibrous structure of the vitreous body, and determine a thickness, a width, an area or a volume or the like of the fibrous structure. Further, analysis processing according to the analysis conditions is also not limited to the processing described above, and may be arbitrarily set according to the desired configuration.

The display controlling unit 350 can cause the result of image analysis performed by the analyzing unit 1924 to be displayed on the display unit 50 together with the high quality tomographic image or separately from the high quality tomographic image.

Next, a series of image processing operations according to the present embodiment will be described referring to FIG. 20. FIG. 20 is a flowchart of a series of image processing operations according to the present embodiment. Note that, since step S2001 to step S2003 are the same as step S1101 to S1103 according to Embodiment 1, a description of these steps will be omitted hereunder.

Upon the image quality improving unit 322 generating a high quality tomographic image in step S2003, similarly to step S1103, the processing shifts to step S2004. In step S2004, the analyzing unit 1924 performs segmentation processing with respect to the generated high quality tomographic image to thereby detect a plurality of different regions in the tomographic image. As the plurality of regions, the analyzing unit 1924 can detect, for example, a region of a vitreous body portion, a region of a retina portion, and a region of a choroid portion. Note that, any known method can be used as the method of segmentation processing, and for example the segmentation processing may be rule-based segmentation processing. Here, the term "rule-based processing" refers to processing that utilizes, for example, known regularity such as the regularity of the shape of the retina.

Thereafter, the analyzing unit 1924 performs image analysis with respect to each detected region based on an analysis condition set for each detected region. For example, in accordance with an analysis condition, the analyzing unit 1924 performs layer extraction or blood vessel extraction for a region for which the analysis condition in question has been set, and calculates the layer thickness or blood vessel density. Note that, the layer extraction or blood vessel extraction may be performed by any known segmentation processing or the like. Further, in accordance with an analysis condition, the analyzing unit 1924 may detect the vitreous body, detachment of the vitreous body, or the fibrous structure of the vitreous body, and may perform quantification of these. Note that, when detecting the vitreous body, detachment of the vitreous body, or the fibrous structure of the vitreous body, the analyzing unit 1924 can additionally perform contrast enhancement, binarization, morphology processing, boundary tracking processing or the like.

In step S2005, the display controlling unit 350 causes the respective analysis results (for example, layer thickness, blood vessel density, area of the vitreous body) obtained by analysis by the analyzing unit 1924 to be displayed on the display unit 50 together with the high quality tomographic image that the image quality improving unit 322 generated. Note that, the form of displaying the analysis results may be any form according to a desired configuration. For example, the display controlling unit 350 may display the analysis result for the respective regions in association with the respective regions of the high quality tomographic image. Further, the display controlling unit 350 may cause the analysis results to be displayed on the display unit 50 separately from the high quality tomographic image. When the display processing by the display controlling unit 350 ends, the series of image processing operations ends.

Thus, the controlling unit 1900 according to the present embodiment includes the analyzing unit 1924 that performs image analysis by applying different analysis conditions to regions that are different to each other in a high quality tomographic image (second tomographic image) which the image quality improving unit 322 generated. The display controlling unit 350 causes analysis results with respect to each of the plurality of regions that are different to each other in the high quality tomographic image that were obtained by the analyzing unit 1924 to be displayed on the display unit 50.

According to this configuration, in order to perform image analysis with respect to a high quality tomographic image generated by the image quality improving unit 322, the analyzing unit 1924 can more appropriately detect features and the like within the image, and perform image analysis with higher accuracy. Further, by performing image analysis according to an analysis condition that is set for each region with respect to a high quality tomographic image that seems to be an image for which appropriate image processing is performed for each region, the analyzing unit 1924 can output an appropriate analysis result for each region. Therefore, the operator can quickly obtain an appropriate analysis result with respect to the eye to be examined.

In the present embodiment, the analyzing unit 1924 automatically performs image analysis according to an analysis condition for each region with respect to a high quality tomographic image. On the other hand, the analyzing unit 1924 may start image processing with respect to a high quality tomographic image according to an instruction by the operator.

The analyzing unit 1924 according to the present embodiment may also be applied to the controlling unit 1600 according to Embodiment 2. In this case, with respect to the tomographic image generated in step S1705 to step S1707, the analyzing unit 1924 may perform the aforementioned image analysis, or may perform only image processing with respect to a region it is desired to observe that is selected in step S1704. Note that, in a case where segmentation processing is performed when performing image quality improving, the analyzing unit 1924 can use the result of the segmentation processing to perform the aforementioned image analysis with respect to the high quality tomographic image.

In addition, in the present embodiment, the analyzing unit 1924 performs segmentation processing on a high quality tomographic image generated by the image quality improving unit 322, and detects regions that are different to each other. In this regard, for example, in a case where the analyzing unit 1924 is applied to the controlling unit according to Modification 3 of Embodiment 1, the analyzing unit 1924 may ascertain a plurality of different regions in a high quality tomographic image, based on a label image that was obtained using the first learned model.

(Modification 5)

In addition, the image processing unit 320, 1620 or 1920 may, with respect to a tomographic image, use a learned model for segmentation to generate a label image and perform segmentation processing. Here, the term "label image" refers to a label image in which a label of a region has been given to each pixel with respect to a tomographic image as mentioned above. Specifically, the term "label image" refers to an image in which arbitrary regions among a group of regions visualized in an image are classified according to identifiable pixel value (hereunder, referred to as a "label value") groups. Here, a region of interest (ROI) and a volume of interest (VOI) and the like are included in the arbitrary regions that are identified.

When identifying groups of coordinates of pixels having an arbitrary label value from an image, it is possible to identify a group of coordinates of pixels that visualize a corresponding region such as a retinal layer in the image. Specifically, for example, in a case where a label value that indicates the ganglion cell layer forming the retina is "1", a coordinate group for which the pixel value is "1" is identified among the pixel groups of the image, and a pixel group corresponding to the coordinate group is extracted from the image. By this means, the region of the ganglion cell layer in the image can be identified.

Note that, the segmentation processing may include processing in which the label image is subjected to reduction or enlargement processing. At such time, the use of a nearest-neighbor method or the like that does not erroneously generate an undefined label value or a label value that should not exist at the corresponding coordinates may be adopted as an image interpolation processing method that is used for reducing or enlarging the label image.

The segmentation processing will now be described in detail. The term "segmentation processing" refers to processing that identifies a region called an ROI or a VOI such as an organ or a lesion that is visualized in an image, in order to utilize such regions for image diagnosis or image analysis. For example, according to the segmentation processing, a group of regions of a layer group constituting the retina can be identified from an image obtained by OCT imaging for which the posterior segment of the eyeball was taken as the imaging target. Note that, if regions to be identified are not visualized in the relevant image, the number of identified regions is 0. Further, if a group of a plurality of regions to be identified is visualized in the image, the number of identified regions may be a plural, or may be a single region that surrounds a group of regions so as to include the group of regions.

The identified group of regions is output as information that can be utilized in other processing. Specifically, for example, a group of coordinates of pixel groups that constitute the identified group of regions, respectively, can be output as a numerical value data group. Further, for example, a group of coordinates indicating a rectangular region, an elliptical region, a parallelepiped region, an ellipsoidal region or the like including each of the identified groups of regions can also be output as a numerical value data group. In addition, for example, a group of coordinates indicating a straight line, a curved line, a plane, a curved surface or the like that is the boundary of an identified group of regions can be output as a numerical value data group. Further, for example, a label image indicating an identified group of regions can also be output.

In this case, for example, a convolutional neural network (CNN) can be used as a machine learning model for segmentation. Note that, for example, a CNN (U-Net type machine learning model) as illustrated in FIG. 10 or a model obtained by combining a CNN and an LSTM (long short-term memory) can be used as the machine learning model according to the present modification. Further, an FCN (fully convolutional network) or a SegNet or the like can also be used as the machine learning model. In addition, a machine learning model or the like that performs object recognition in region units can be used according to a desired configuration. As a machine learning model for performing object recognition in region units, for example, RCNN (Region CNN), Fast-RCNN, or Faster-RCNN can be used. In addition, YOLO (You Only Look Once) or SSD (Single Shot Detector, or Single Shot MultiBox Detector) can also be used as a machine learning model for performing object recognition in region units. Note that, the machine learning models described as examples here may be applied to the first learned model described in Modification 3.

Further, for the training data of a machine learning model for segmentation, a tomographic image is adopted as input data, and a label image obtained by giving a label of a region to each pixel with respect to the tomographic image is adopted as output data. As the label image, for example, a label image in which labels such as inner limiting membrane (ILM), nerve fiber layer (NFL), ganglion cell layer (GCL), photoreceptor inner segment-outer segment junction (ISOS), retinal pigment epithelium (RPE), Bruch's membrane (BM) and choroid have been given to regions can be used. Note that, as other regions, for example, a label image in which labels such as vitreous body, sclera, outer plexiform layer (OPL), outer nuclear layer (ONL), inner plexiform layer (IPL), inner nuclear layer (INL), cornea, anterior chamber, iris, and crystalline lens have been given to regions may be used. Note that, with regard to a label image described as an example here, the label image may also be used as output data of training data relating to the first learned model mentioned in Modification 3.

Further, the input data of the machine learning model for segmentation is not limited to a tomographic image. The input data may be an anterior ocular segment image, an SLO fundus image, a fundus front image obtained using a fundus camera or the like, or an en-face image or OCTA front image to be described later. In this case, for the training data, various kinds of images can be adopted as input data, and a label image in which region names or the like have been labeled for each pixel of the various kinds of images can be adopted as output data. For example, in a case where the input data of the training data is a fundus front image, the output data may be an image in which labels have been given to regions such as a cup, a disc and a peripheral portion of the optic nerve head. Note that, the input data may be an image that was subjected to image quality improving, or may be an image that was not subjected to image quality improving.

Note that, a label image that is used as output data may be an image in which a label has been given to each region in a tomographic image by a physician or the like, or may be an image in which a label has been given to each region by rule-based region detection processing. However, if machine learning is performed using a label image for which labeling has not been appropriately performed as the output data of training data, there is a probability that an image obtained using a learned model that performed learning using the training data in question will also be a label image for which labeling has not been appropriately performed. Therefore, by excluding pairs including such kind of label images from the training data, the probability that an inappropriate label image will be generated using the learned model can be reduced. Here, the term "rule-based region detection processing" refers to detection processing that utilizes, for example, known regularity such as the regularity of the shape of the retina.

By performing segmentation processing using such a kind of learned model for segmentation, it can be expected that the image processing units 320, 1620 and 1920 will quickly and accurately detect specific regions with respect to various kinds of images. Note that, the learned model for segmentation may be used as the first learned model mentioned in Modification 3. Further, in Embodiment 3, the analyzing unit 1924 may perform segmentation processing using the learned model according to the present modification.

Note that, a learned model for segmentation may be prepared for each kind of image among various kinds of images that are input data. In addition, the learned model for segmentation may be a learned model that has performed learning with respect to images of each imaged site (for example, the center of the macular area and the center of the optic nerve head), or may be a learned model that has performed learning irrespective of the imaged sites.

Further, when generating an en-face image or an OCTA front image, depth ranges are set and specified as described later. Therefore, with regard to an en-face image or an OCTA front image, a learned model may be prepared for each depth range for generating an image.

Note that, the image processing units 320, 1620 and 1920 can perform segmentation processing using rule-based segmentation processing or a learned model with respect to at least one of an image before performing image quality improving processing and an image after performing image quality improving processing by the image quality improving unit 322 or 1622. Thus, the image processing unit 320 can identify different regions in the at least one image in question. In particular, the image processing units 320, 1620 and 1920 perform segmentation processing using a learned model for segmentation (third learned model) that is different from a learned model for generating a high quality image (second medical image). Thus, it can be expected that different regions in the at least one image in question will be quickly and accurately identified.

(Modification 6)

High quality images obtained using a learned model by the image quality improving units 322 and 1622 according to the embodiments and modifications described above may be manually modified according to an instruction from the operator. For example, an image quality improving model may be updated by incremental learning that, as training data, adopts a high quality image for which image processing of a specified region was changed according to an instruction of the examiner. In this case, for example, an image that was modified in a manner in which, in a high quality image generated using the image quality improving model, gradation conversion processing with respect to the retina portion was performed with respect to regions in which gradation conversion processing had been performed with respect to the vitreous body portion or the choroid portion can be adopted as training data for incremental learning. Conversely, an image that was modified in a manner in which, in a high quality image generated using the image quality improving model, gradation conversion processing with respect to the vitreous body portion or the choroid portion was performed with respect to regions in which gradation conversion processing had been performed with respect to the retina portion can be adopted as training data for incremental learning.

In addition, the image quality improving model may be updated by incremental learning in which the value of a ratio that was set (changed) in accordance with an instruction from the examiner is adopted as learning data. For example, if the examiner tends to set the ratio of the input image to the high quality image high when the input image is relatively dark, the learned model performs incremental learning so as to have such a tendency. Thus, for example, the learned model can be customized as a learned model that can obtain a combining ratio that matches the preference of the examiner.

At such time, a button for determining, in accordance with an instruction from the examiner, whether or not to use the set (changed) value of the ratio as training data for incremental learning may be displayed on the display screen. By this means, the controlling unit 30, 1600 or 1900 can determine whether or not incremental learning is necessary according to an instruction of the operator. Further, a configuration may be adopted in which a ratio determined using the learned model is taken as a default value and, thereafter, it is possible to change the ratio value from the default value in accordance with an instruction from the examiner.

Note that, as described later, a learned model can also be provided in an apparatus such as a server. In such a case, the controlling unit 30, 1600 or 1900 can, according to an instruction by an operator to perform incremental learning, transmit and store an input image and a high quality image on which the aforementioned modification was performed as a pair of training data to the relevant server or the like. In other words, the controlling unit 30, 1600 or 1900 can determine whether to transmit training data for incremental learning to an apparatus such as a server which is equipped with a learned model, according to an instruction of the operator.

Note that, with respect to the various learned models described in the foregoing embodiments and other modifications, the respective learned models may also similarly perform incremental learning using data that was manually modified according to an instruction of the operator as training data. Further, a determination as to whether or not incremental learning is necessary and a determination as to whether or not to transmit data to a server may also be performed by similar methods. In these cases also, it can be expected that the accuracy of each kind of processing will be enhanced, and processing in accordance with the tendency of the preference of the examiner can be performed.

For example, with regard to the learned model for segmentation, incremental learning may be performed in which data that was manually modified according to an instruction of the operator is used as training data. Further, a determination as to whether or not incremental learning is necessary and a determination as to whether or not to transmit data to a server can be performed by the same methods as the methods described above. In these cases also, it can be expected that the accuracy of the segmentation processing will be enhanced, and processing in accordance with the tendency of the preference of the examiner can be performed.

(Modification 7)

In the respective embodiments and modifications described above, the image processing units 320, 1620 and 1920 can generate an en-face image or an OCTA front image of the eye to be examined using a three-dimensional tomographic image. In such a case, the display controlling unit 350 can cause the generated en-face image or OCTA image to be displayed on the display unit 50. Further, the analyzing unit 1924 can also perform analysis with respect to the generated en-face image or OCTA image.

An en-face image and an OCTA front image will now be described. An en-face image is a front image generated by projecting data in an arbitrary depth range in a three-dimensional tomographic image obtained by using light interference in the X- and Y-directions. The front image is generated by projecting or integrating data corresponding to a depth range that is at least a partial depth range of volume data (a three-dimensional tomographic image) obtained using light interference and that is defined based on two reference planes onto a two-dimensional plane.

For example, an en-face image can be generated by projecting data corresponding to a depth range which, among volume data, is determined based on retinal layers detected by segmentation processing with respect to a two-dimensional tomographic image, onto a two-dimensional plane. Note that, as a technique for projecting data corresponding to a depth range defined based on two reference planes onto a two-dimensional plane, for example, a technique can be used in which representative values of data within the relevant depth range are adopted as pixel values on a two-dimensional plane. In this case, examples of the representative values can include a value such as an average value, a median value or a maximum value of pixel values within a range in the depth direction (depth range) of the region surrounded by the two reference planes.

The depth range pertaining to the en-face image may be specified based on, for example, two layer boundaries relating to retinal layers detected by the aforementioned technique using rule-based segmentation processing or by segmentation processing using the learned model mentioned in Modification 5. Further, the depth range in question may include only a range corresponding to a predetermined number of pixels in a deeper direction or a shallower direction with reference to one of the two layer boundaries relating to retinal layers detected by these segmentation processing operations. In addition, the depth range pertaining to the en-face image may be, for example, a range that has been changed (offset) according to an instruction of the operator from a range between the two layer boundaries relating to the detected retinal layers. At such time, for example, the operator can change the depth range by moving an indicator indicating the upper limit or the lower limit of the depth range that has been superimposed on a tomographic image subjected to image quality improving by the image quality improving unit 322 or 1622 or on a tomographic image that has not been subjected to image quality improving.

Note that, the generated front image is not limited to an en-face image based on intensity values (intensity en-face image) as described above. The generated front image may be, for example, a motion contrast front image that, with respect to motion contrast data with respect to a plurality of items of volume data, is generated by projecting or integrating data corresponding to the aforementioned depth range on a two-dimensional plane. Here, the term "motion contrast data" refers to data indicating changes between a plurality of items of volume data obtained by controlling so that measuring light is scanned a plurality of times over the same region (same position) of an eye to be examined. At such time, the volume data is composed of a plurality of tomographic images obtained at different positions. The motion contrast data can then be obtained as volume data by, at respective positions that are different to each other, obtaining data showing changes between a plurality of tomographic images that were obtained at approximately the same position. Note that, in relation to OCT angiography that measures blood flow movement, a motion contrast front image is also referred to as an OCTA front image (OCTA en-face image), and motion contrast data is also referred to as OCTA data. The motion contrast data can be obtained, for example, as a variance value or a decorrelation value between two tomographic images or between interference signals corresponding to the two tomographic images, or as a value obtained by dividing a maximum value by a minimum value (maximum value/minimum value), and may be obtained by any known method. At such time, the two tomographic images can be obtained, for example, by controlling so that measuring light is scanned a plurality of times over the same region (same position) of the eye to be examined.

Further, the three-dimensional OCTA data (OCT volume data) that is used when generating the OCTA front image may be generated using at least one part of interference signals which are common with volume data including the tomographic image that is used for image segmentation. In this case, the volume data (three-dimensional tomographic image) and the three-dimensional OCTA data can correspond with each other. Therefore, for example, a motion contrast front image corresponding to a depth range that is determined based on retinal layers detected by image segmentation can be generated by using three-dimensional motion contrast data that corresponds to the volume data.

Note that, the volume data that is used when generating an en-face image or an OCTA front image may be constituted by tomographic images subjected to image quality improving by the image quality improving unit 322 or 1622. In other words, the image processing unit 320, 1620 or 1920 may generate an en-face image or an OCTA front image using volume data composed of a plurality of tomographic images obtained at a plurality of different positions that were subjected to image quality improving. In other words, in a case where the images before and after performing image quality improving processing by the image quality improving unit 322 or 1622 are three-dimensional OCT tomographic images, the image processing unit 320, 1620 or 1920 can generate a front image corresponding to a partial depth range of images after the image quality improving processing. Thus, the image processing unit 320, 1620 or 1920 can generate a high quality front image based on high quality three-dimensional tomographic images.

(Modification 8)

Next, an image processing apparatus according to Modification 8 will be described referring to FIG. 21A to FIG. 23. In the embodiments and modifications described above, the image quality improving units 322 and 1622 perform image quality improving processing with respect to a tomographic image using a learned model for improving image quality (image quality improving model). In this regard, the image quality improving units 322 and 1622 may perform image quality improving processing using an image quality improving model with respect to other images, and the display controlling unit 350 may cause various kinds of images subjected to image quality improving on the display unit 50. For example, the image quality improving unit 322 or 1622 may subject an intensity en-face image or OCTA front image or the like to image quality improving processing. Further, the display controlling unit 350 can cause the display unit 50 to display at least one of a tomographic image, an intensity en-face image and an OCTA front image that underwent image quality improving processing by the image quality improving unit 322 or 1622. Note that, an image that is subjected to image quality improving and displayed may be an SLO fundus image, a fundus image obtained with a fundus camera (not illustrated) or the like, or a fluorescence fundus image or the like.

In this case, for the training data of an image quality improving model for performing image quality improving processing on various kinds of images, with respect to various kinds of images, an image before image quality improving processing is adopted as input data and an image after image quality improving processing is adopted as output data, similarly to the training data of the image quality improving models according to the embodiments and modifications described above. Note that, with regard to image quality improving processing relating to the training data, similarly to the embodiments and modifications described above, the processing may be, for example, arithmetic averaging processing, processing using a smoothing filter, maximum a posteriori processing (MAP estimation processing), or gradation conversion processing. Further, as an image after image quality improving processing, for example, an image on which filter processing such as noise removal and edge enhancement was performed may be used, or an image for which the contrast was adjusted so as to obtain a high-intensity image from a low-intensity image may be used. In addition, with regard to output data of training data pertaining to the image quality improving model, since it suffices that the output data is a high quality image, the output data may be an image that was imaged using an OCT apparatus with higher performance than the OCT apparatus used to image the image that is the input data, or may be an image that was imaged with high load settings.

Further, an image quality improving model may be prepared for each kind of image on which image quality improving processing is to be performed. For example, an image quality improving model for tomographic images, an image quality improving model for intensity en-face images, and an image quality improving model for OCTA front images may be prepared. In addition, an image quality improving model for intensity en-face images or an image quality improving model for OCTA front images may be a learned model that comprehensively learned images at different depth ranges with respect to a depth range (generation range) pertaining to generation of an image. The images at different depth ranges may include, for example, images of a surface layer (Im2110), a deep layer (Im2120), an outer layer (Im2130) and a choroidal vascular network (Im2140) as illustrated in FIG. 21A. Further, with respect to the image quality improving model for intensity en-face images or the image quality improving model for OCTA front images, a plurality of image quality improving models that learned images for each different depth range may be prepared. Note that, an image quality improving model that performs image quality improving processing with respect to an image other than a tomographic image is not limited to an image quality improving model that performs different image processing for each region, and may be an image quality improving model that performs the same image processing with respect to the entire image.

Further, in the case of preparing an image quality improving model for tomographic images, the image quality improving model may be a learned model that comprehensively learned tomographic images obtained at different positions in the subscanning direction (Y-axis direction). Tomographic images Im2151 to Im2153 illustrated in FIG. 21B are examples of tomographic images obtained at different positions in the subscanning direction. However, in the case of images obtained by imaging of locations where the imaged sites (for example, the center of the macular area and the center of the optic nerve head) differ, a configuration may be adopted so as to perform learning separately for each imaged site, or a configuration may be adopted so as to perform learning together without being concerned about the imaged sites. Note that, an intensity tomographic image and a tomographic image of motion contrast data may be included as tomographic images to be subjected to image quality improving. However, since image feature values differ significantly between an intensity tomographic image and a tomographic image of motion contrast data learning may be performed separately as respective image quality improving models for each of these kinds of images.

In the present modification, an example is described in which the display controlling unit 350 displays an image for which the image quality improving unit 322 or 1622 performed image quality improving processing on the display unit 50. Note that, although the present modification is described using FIG. 22A and FIG. 22B, the display screens are not limited to the examples illustrated in FIG. 22A and FIG. 22B. Image quality improving processing (quality improvement processing) can also be similarly applied in a display screen that displays, side-by-side, a plurality of images obtained at different dates and times, as when performing a follow-up observation. Further, image quality improving processing can also be similarly applied in a display screen on which the examiner confirms whether or not the imaging is successful immediately after imaging, as in the case of an imaging confirmation screen. The display controlling unit 350 can cause a plurality of high quality images which the image quality improving unit 322 or 1622 generated or a low quality image which was not subjected to image quality improving to be displayed on the display unit 50. Further, with respect to a plurality of high quality images or a low quality images which were not subjected to image quality improving that are displayed on the display unit 50, the display controlling unit 350 can cause each of a low quality image and a high quality image selected according to an instruction of the examiner to be displayed on the display unit 50. The image processing apparatus can also output a low quality image and a high quality image selected according to an instruction of the examiner to outside of the image processing apparatus.

Figure 22A:
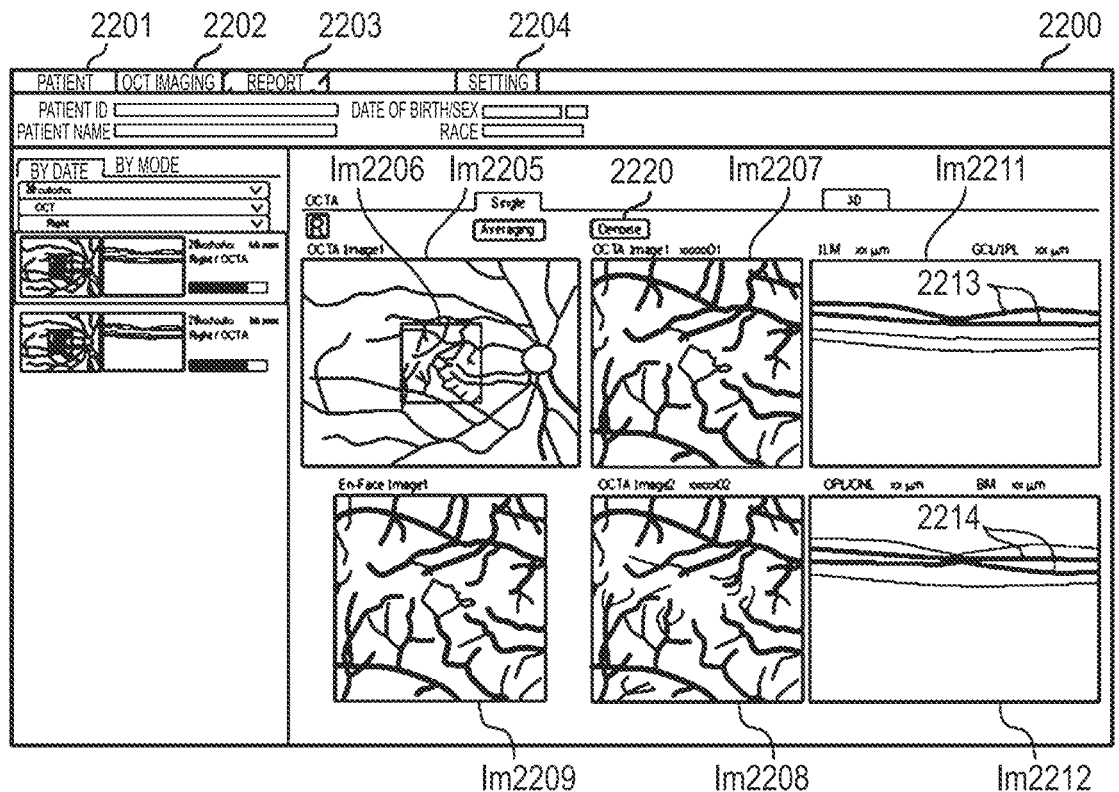
FIG. 22A is a view illustrating an example of a user interface according to Embodiment 4.
Figure 22B:
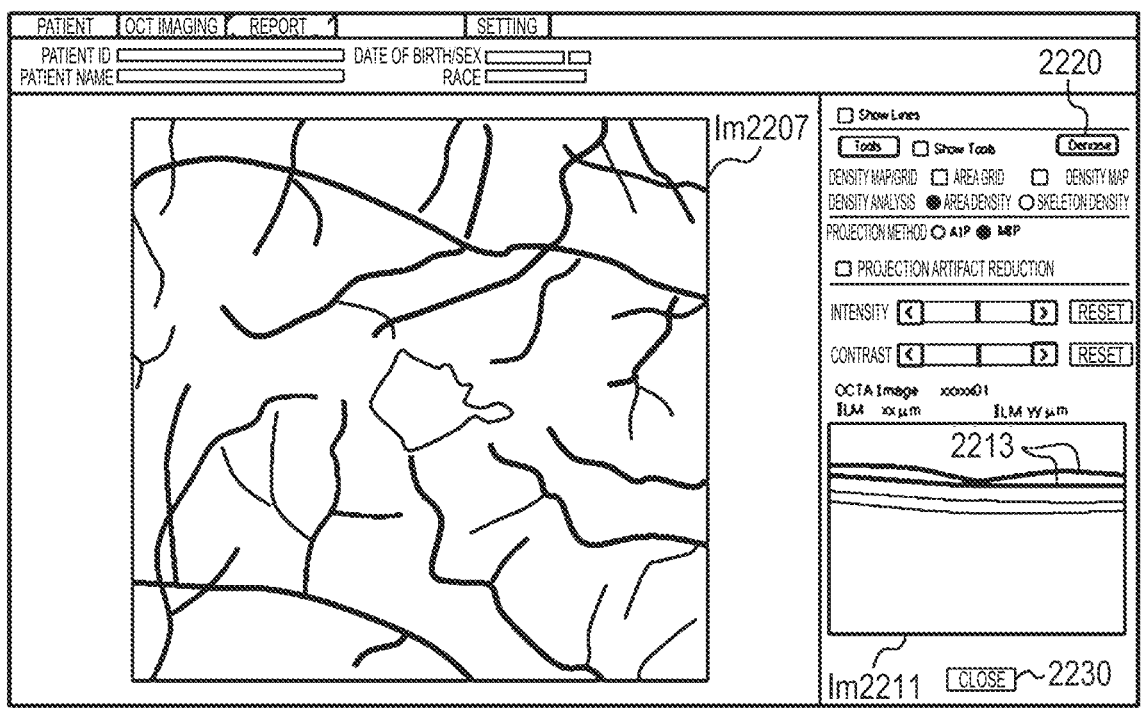
FIG. 22B is a view illustrating an example of the user interface according to Embodiment 4.

Hereunder, one example of a display screen 2200 of an interface according to the present modification is described referring to FIG. 22A and FIG. 22B. The display screen 2200 represents an entire screen, and a "Patient" tab 2201, an "Imaging" tab 2202, a "Report" tab 2203 and a "Setting" tab 2204 are shown in the display screen 2200. Further, diagonal lines in the "Report" tab 2203 indicate an active state of a report screen. In the present modification, an example of displaying the report screen will be described.

In the report screen illustrated in FIG. 22A, an SLO fundus image Im2205, OCTA front images Im2207 and Im2208, an intensity en-face image Im2209, tomographic images Im2211 and Im2212, and a button 2220 are shown. Further, on the SLO fundus image Im2205, an OCTA front image Im2206 corresponding to the OCTA front image Im2207 is displayed in a superimposed manner. In addition, on the tomographic images Im2211 and Im2212, boundary lines 2213 and 2214 of the depth ranges of the OCTA front images Im2207 and Im2208 are displayed in a superimposed manner, respectively. The button 2220 is a button used for designating execution of image quality improving processing. As described later, the button 2220 may be a button for inputting an instruction to display a high quality image.

In the present modification, execution of image quality improving processing is performed when the button 2220 is specified, or whether or not to execute image quality improving processing is determined based on information stored (saved) in a database. First, an example of switching between display of a high quality image and display of a low quality image by the button 2220 being specified in accordance with an instruction from the examiner will be described. Hereunder, an OCTA front image will be described as the target image of the image quality improving processing.

Note that, the depth range of the OCTA front images Im2207 and Im2208 may be determined using information of retinal layers detected by the aforementioned conventional segmentation processing or by segmentation processing using a learned model. The depth range, for example, may be a range between two layer boundaries relating to the detected retinal layers, or may include only a range corresponding to a predetermined number of pixels in a deeper direction or a shallower direction with reference to one of the two layer boundaries relating to the detected retinal layers. In addition, the depth range may be, for example, a range that has been changed (offset) according to an instruction of the operator from a range between the two layer boundaries relating to the detected retinal layers.

When the examiner specifies the "Report" tab 2203 to thereby transition to the report screen, the display controlling unit 350 displays the low-quality OCTA front images Im2207 and Im2208. Thereafter, when the examiner specifies the button 2220, the image quality improving unit 322 or 1622 executes image quality improving processing on the OCTA front images Im2207 and Im2208 displayed on the screen. After the image quality improving processing is completed, the display controlling unit 350 displays a high quality image which the image quality improving unit 322 or 1622 generated on the report screen. Note that, since the OCTA front image Im2206 is an image in which the OCTA front image Im2207 is displayed in a superimposed manner on the SLO fundus image Im2205, the display controlling unit 350 can also cause an image obtained by performing image quality improving processing with respect to the OCTA front image Im2206 to be displayed. Further, the display controlling unit 350 can change the display of the button 2220 to an active state to provide a display from which it can be understood that image quality improving processing was executed.

In this case, execution of processing by the image quality improving unit 322 or 1622 need not be limited to the timing at which the examiner specifies the button 2220. Since the kind of the OCTA front images Im2207 and Im2208 to be displayed when the report screen is opened is known in advance, the image quality improving unit 322 or 1622 may execute image quality improving processing at the time when the displayed screen transitions to the report screen. Subsequently, at the timing at which the button 2220 is pressed, the display controlling unit 350 may display a high quality image on the report screen. In addition, it is not necessary that the number of kinds of image on which image quality improving processing is performed in response to an instruction from the examiner or when transitioning to the report screen is two. A configuration may be adopted so as to perform processing on images for which there is a high possibility of being displayed, for example, processing may be performed on a plurality of OCTA front images such as the images of the surface layer (Im2110), the deep layer (Im2120), the outer layer (Im2130) and the choroidal vascular network (Im2140) illustrated in FIG. 21A. In this case, an image obtained by performing image quality improving processing may be temporarily stored in a memory or may be stored in a database.

Next, a case where image quality improving processing is executed based on information stored (saved) in a database is described. In a case where a state whereby execution of image quality improving processing is to be performed is stored in a database, upon the display transitioning to the report screen, the display controlling unit 350 causes a high quality image obtained as a result of the image quality improving unit 322 or 1622 executing image quality improving processing to be displayed by default on the display unit 50. Further, a configuration can be adopted so that, by the display controlling unit 350 causing the button 2220 to be displayed in an active state by default, the examiner can know that a high quality image obtained by executing image quality improving processing is being displayed. If the examiner wishes to display a low quality image in a state prior to image quality improving processing, the examiner can perform an operation to specify the button 2220 and thereby release the active state, so that the display controlling unit 350 causes the low quality image to be displayed on the display unit 50. At such time, if the examiner wishes to return the image that is displayed to the high quality image, the examiner specifies the button 2220 so as to enter the active state, and thus the display controlling unit 350 causes the high quality image to be displayed once more on the display unit 50.

It is assumed that it can be specified whether or not to execute image quality improving processing on data stored in the database commonly for all of the data stored in the database, and with respect to respective classes of data such as for each set of imaging data (for each examination). For example, in a case where a state whereby image quality improving processing is to be executed for the entire database has been stored, the examiner can store a state whereby image quality improving processing is not to be executed with respect to an individual item of imaging data (individual examination). In this case, for an individual item of imaging data with respect to which a state whereby image quality improving processing is not to be executed was stored, the next time the relevant imaging data is displayed, the imaging data can be displayed in a state in which image quality improving processing has not been executed thereon. According to this configuration, in a case in which whether or not to execute image quality improving processing in imaging data units (examination units) has not been specified, processing can be executed based on information specified with respect to the entire database. Further, in a case where execution of image quality improving processing in imaging data units (examination units) has been specified, processing can be executed individually based on the information in question.

Note that, a user interface (not illustrated) (for example, a "Store" button) may be used to store a state in which image quality improving processing has been executed for each item of imaging data (for each examination). Further, when transitioning to other imaging data (another examination) or other patient data (for example, changing to a display screen other than the report screen in accordance with an instruction from the examiner), based on the display state (for example, the state of the button 2220), a state whereby execution of image quality improving processing is to be performed may be stored.

Although an example has been illustrated in which the OCTA front images Im2207 and Im2208 are displayed as OCTA front images in the present modification, it is possible to change an OCTA front image to be displayed in accordance with a specification of the examiner. Therefore, a description will now be given regarding changing a displayed image in a case where execution of image quality improving processing has been specified (the button 2220 is in an active state).

Changing of a displayed image is performed using a user interface (not illustrated) (for example, a combo box). For example, in a case where the examiner changes the kind of image from a surface layer image to a choroidal vascular network image, the image quality improving unit 322 or 1622 executes image quality improving processing for the choroidal vascular network image, and the display controlling unit 350 displays a high quality image which the image quality improving unit 322 or 1622 generated on the report screen. In other words, in response to an instruction from the examiner, the display controlling unit 350 may change the display of a high quality image of a first depth range to the display of a high quality image of a second depth range that is at least partially different from the first depth range. At this time, in accordance with the first depth range being changed to the second depth range in response to an instruction from the examiner, the display controlling unit 350 may change the display of a high quality image of the first depth range to the display of a high quality image of the second depth range. Note that, in a case where, as described above, high quality images have already been generated with respect to images for which the possibility of being displayed upon transitioning to the report screen is high, the display controlling unit 350 can display a high quality image which has already been generated.

Further, a method for changing the kind of image is not limited to the method described above, and it is also possible to generate OCTA front images for which different depth ranges are set by changing the layer that serves as a reference and an offset value, and to display high quality images obtained by executing image quality improving processing on the generated OCTA front images. In such a case, when the layer that serves as a reference or an offset value is changed, the image quality improving unit 322 or 1622 executes image quality improving processing with respect to an arbitrary OCTA front image, and the display controlling unit 350 displays a high quality image on the report screen. Note that, changing of a layer that serves as a reference or an offset value can be performed using a user interface (not illustrated) (for example, a combo box or a text box). Further, the depth range (generation range) of the OCTA front image can also be changed by dragging any one of the boundary lines 2213 and 2214 (moving the layer boundary) that are displayed in a superimposed manner on the tomographic images Im2211 and Im2212, respectively.

In a case where a boundary line is changed by dragging, execution commands with respect to image quality improving processing are continuously executed. Therefore, the image quality improving unit 322 or 1622 may be configured to always perform processing with respect to an execution command, or may be configured to execute processing after the layer boundary has been changed by dragging. Alternatively, although commands to execute image quality improving processing are issued continuously, the image quality improving unit 322 or 1622 may be configured to cancel the previous command at the time point at which the next command arrives, and execute the most recent command.

Note that, image quality improving processing takes a relatively long time in some cases. Consequently, even when a command is executed at any of the timings described above, it may take a relatively long time until a high quality image is displayed. Therefore, during a period from when a depth range for generating an OCTA front image is set in response to an instruction from the examiner until a high quality image is displayed, a low-quality OCTA front image (low quality image) corresponding to the set depth range may be displayed. In other words, a configuration may be adopted so that when the aforementioned depth range is set, a low-quality OCTA front image (low quality image) corresponding to the set depth range is displayed, and when the image quality improving processing is completed, the display of the low-quality OCTA front image is changed to a display of the high quality image. Further, information indicating that image quality improving processing is being executed may be displayed during the period from when the aforementioned depth range is set until the high quality image is displayed. Note that, these processing operations are not limited to a configuration applied in a case for which it is taken as a premise that the state is one in which execution of image quality improving processing has already been specified (the button 2220 is in an active state). For example, it is also possible to apply these processing operations during a period until a high quality image is displayed when execution of image quality improving processing was instructed in accordance with an instruction from the examiner.

Although in the present modification an example has been illustrated in which the OCTA front images Im2207 and Im2208 relating to different layers are displayed as OCTA front images, and a low quality image and a high quality image are displayed by switching therebetween, the images that are displayed are not limited thereto. For example, a configuration may be adopted so as to display a low-quality OCTA front image as the OCTA front image Im2207 and a high-quality OCTA front image as the OCTA front image Im2208 side by side. In the case of displaying the images by switching therebetween, since images are switched at the same place it is easy to make a comparison of portions at which there is a change, while in the case of displaying images side by side, it is easy to compare the entire images since the images can be displayed at the same time.

Next, FIG. 22A and FIG. 22B will be used to describe execution of image quality improving processing in the case of screen transition. FIG. 22B is an example of a screen on which the OCTA front image Im2207 illustrated in FIG. 22A is displayed in an enlarged manner. In the screen example illustrated in FIG. 22B also, similarly to FIG. 22A, the button 2220 is displayed. A screen transition from the screen illustrated in FIG. 22A to the screen illustrated in FIG. 22B is specified, for example, by double clicking on the OCTA front image Im2207, and a screen transition from the screen illustrated in FIG. 22B to the screen illustrated in FIG. 22A is specified by clicking on a "Close" button 2230. Note that, with regard to screen transition, a method for transitioning from one screen to another is not limited to the method described here, and a user interface (not illustrated) may also be used.

In a case where execution of image quality improving processing has been specified (the button 2220 is active) at the time of screen transition, that state is also maintained when the screen transition occurs. In other words, in a case where the screen illustrated in FIG. 22B is transitioned to in a state in which a high quality image is displayed on the screen illustrated in FIG. 22A, the high quality image is also displayed on the screen illustrated in FIG. 22B. Further, the button 2220 is placed in an active state. The same applies in the case of transitioning from the screen illustrated in FIG. 22B to the screen illustrated in FIG. 22A. On the screen illustrated in FIG. 22B, the display can also be switched to a low quality image by specifying the button 2220.

With regard to the screen transitions, the screen transitions are not limited to the screens described here, and as long as the transition is to a screen displaying the same imaging data, such as a display screen for follow-up observation or a display screen for a panorama image, transition is performed while maintaining the display state of the high quality image. In other words, on the display screen after transition, an image that corresponds to the state of the button 2220 on the display screen before transition can be displayed. For example, if the button 2220 is in an active state on the display screen before transition, a high quality image is displayed on the display screen after transition. Further, for example, if the active state of the button 2220 is released on the display screen before transition, a low quality image is displayed on the display screen after transition. Note that, a configuration may be adopted so that, if the button 2220 is in an active state on the display screen for follow-up observation, a plurality of images obtained at different dates and times (different examination days) that are displayed side by side on the display screen for follow-up observation are switched to high quality images. In other words, a configuration may be adopted so that, if the button 2220 is in an active state on the display screen for follow-up observation, switching to high quality images is collectively performed with respect to the plurality of images obtained at different dates and times.

Figure 23:
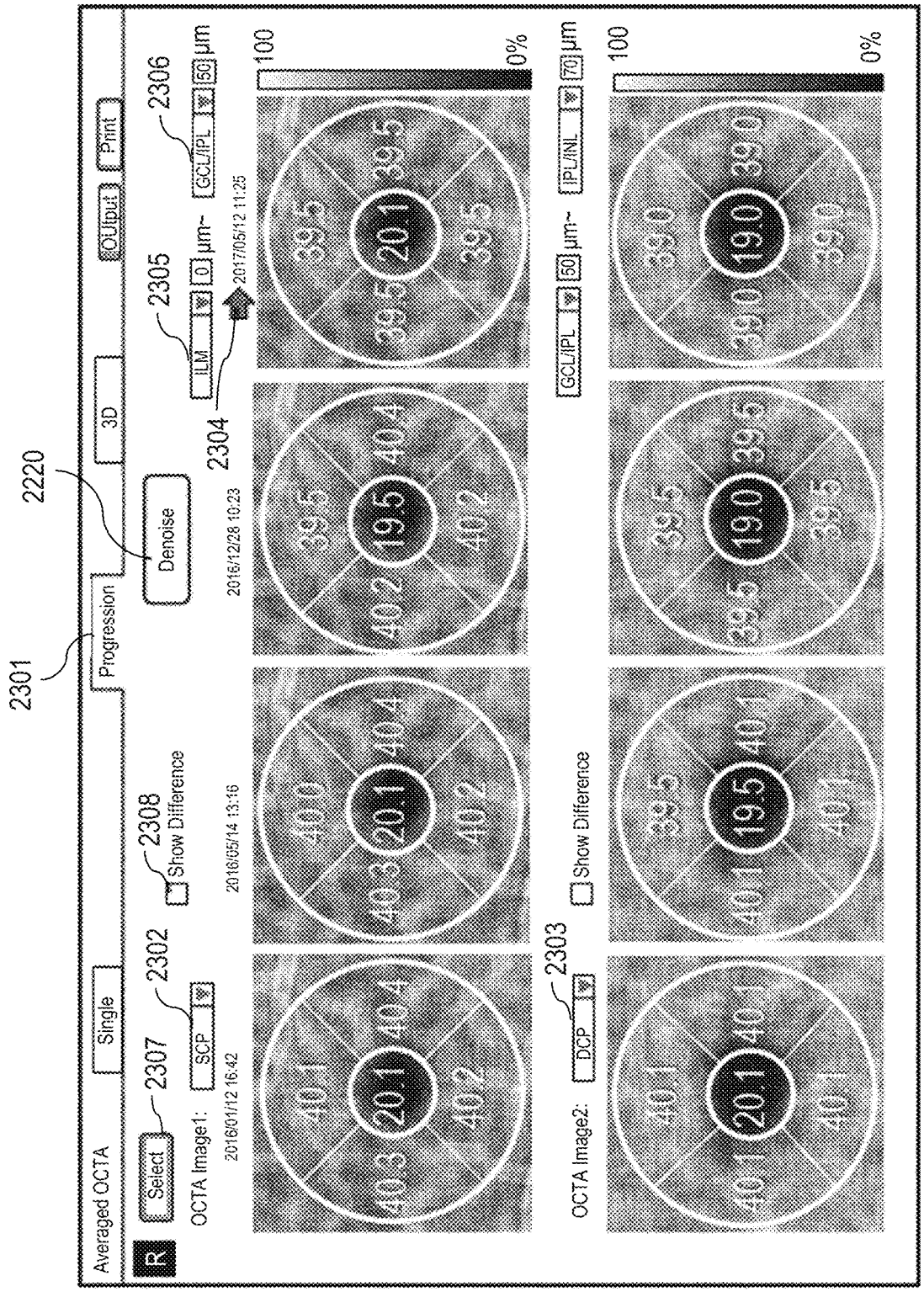
FIG. 23 is a view illustrating an example of the user interface according to Embodiment 4.

An example of a display screen for follow-up observation is illustrated in FIG. 23. Upon a tab 2301 being selected in response to an instruction from the examiner, a display screen for follow-up observation is displayed as illustrated in FIG. 23. At such time, the depth range of OCTA front images can be changed by the examiner selecting a desired set from predefined depth range sets displayed in list boxes 2302 and 2303. For example, superficial capillary is selected in the list box 2302, and deep capillary is selected in the list box 2303. Analysis results for OCTA front images of the superficial capillary are displayed in a display region on the upper side, and analysis results for OCTA front images of the deep capillary are displayed in a display region on the lower side. When a depth range is selected, a plurality of images obtained at different dates and times are collectively changed to a parallel display of analysis results for a plurality of OCTA front images in the selected depth range.

At this time, if the display of analysis results is placed in a non-selected state, the display may be collectively changed to a parallel display of analysis results for a plurality of OCTA front images obtained at different dates and times. If the button 2220 is then specified in accordance with an instruction from the examiner, the display of a plurality of OCTA front images is collectively changed to the display of a plurality of high quality images.

Further, in a case where the display of analysis results is in a selected state, if the button 2220 is specified in accordance with an instruction from the examiner, the display of analysis results for a plurality of OCTA front images is collectively changed to the display of analysis results for a plurality of high quality images. Here, the display of analysis results may be performed such that the analysis results are displayed in a superimposed manner on the images with any degree of transparency. At this time, changing from the display of images to the display of analysis results may be, for example, a change to a state in which the analysis results are superimposed with any degree of transparency on the images that are being displayed. Further, changing from the display of images to the display of analysis results may be, for example, a change to the display of images (for example, two-dimensional maps) obtained by subjecting the respective analysis results and images to blending processing with any degree of transparency.

Further, the kind of layer boundary and the offset position used to specify the depth ranges can each be collectively changed from user interfaces 2305 and 2306. Note that, the user interfaces 2305 and 2306 are one example of interfaces for changing the kind of layer boundary and the offset position, and an interface of any other form may also be used. Note that, the depth ranges of a plurality of OCTA front images obtained at different dates and times may be collectively changed by also causing tomographic images to be displayed together therewith, and moving layer boundary data superimposed on the tomographic images in accordance with an instruction from the examiner. At such time, a plurality of tomographic images obtained at different dates and times may be displayed side by side, and when the aforementioned movement is performed on one tomographic image, the layer boundary data may be similarly moved on the other tomographic images.

Further, the image projection method and whether or not the projection artifact removal processing is to be performed can be changed, for example, by a selection from a user interface such as a context menu.

Further, a selection button 2307 may be selected to display a selection screen (not illustrated), and an image selected from an image list displayed on the selection screen may be displayed. Note that, an arrow 2304 displayed at the upper part of the screen illustrated in FIG. 23 is a mark that indicates the currently selected examination, and the reference examination (baseline) is the examination (leftmost image in FIG. 23) selected at the time of follow-up imaging. Naturally, a mark indicating the reference examination may be displayed on the display unit.

Further, in a case where a "Show Difference" check box 2308 is specified, a measurement value distribution (map or sector map) with respect to the reference image is displayed on the reference image. In addition, in this case, in a region corresponding to an examination date other than the examination date of the reference image, a differential measurement value map is displayed that shows differences between the measurement value distribution calculated for the reference image and a measurement distribution calculated for an image in which the relevant region is displayed. As a measurement result, a trend graph (a graph of measurement values with respect to images for the respective examination dates that is obtained by measuring changes over time) may be displayed on the report screen. In other words, time-series data (for example, a time-series graph) for a plurality of analysis results corresponding to a plurality of images obtained at different dates and times may be displayed. At such time, with regard to analysis results relating to dates and times other than the plurality of dates and times corresponding to the displayed plurality of images also, the analysis results may be displayed as time-series data in a state in which the analysis results can be distinguished (for example, the colors of respective points on a time-series graph differ according to whether or not the corresponding image is displayed) from the plurality of analysis results corresponding to the plurality of images that are being displayed. Further, a regression line (curve) of the trend graph and a corresponding mathematical expression may be displayed on the report screen.

Although a description relating to an OCTA front image has been given in the present modification, an image to which the processing according to the present modification is applied is not limited thereto. An image relating to processing for displaying an image, image quality improving, and image analysis and the like according to the present modification may be an intensity en-face image. In addition, the different kinds of images are not limited to an en-face image, and may be a different image such as a tomographic image obtained by a B-scan, an SLO fundus image, a fundus image, or a fluorescence fundus image. In this case, a user interface for executing image quality improving processing may be a user interface for instructing the execution of image quality improving processing with respect to a plurality of images of different kinds, or may be a user interface for selecting any image from a plurality of images of different kinds and instructing the execution of image quality improving processing.

For example, in the case of subjecting tomographic images obtained by a B-scan to image quality improving and displaying the resultant images, the tomographic images Im2211 and Im2212 illustrated in FIG. 22A may be subjected to image quality improving and displayed. Further, the tomographic images that were subjected to image quality improving may be displayed in the regions in which the OCTA front images Im2207 and Im2208 are displayed. Note that, the number of tomographic images subjected to image quality improving and displayed may be one tomographic image or may be a plurality of tomographic images. In a case where a plurality of tomographic images are displayed, tomographic images obtained at different positions to each other in the subscanning direction may be displayed, and for example in a case where a plurality of tomographic images obtained by cross-scanning or the like are subjected to image quality improving and displayed, the respective images in the different scanning directions may be displayed. Further, for example, in a case where a plurality of tomographic images obtained by radial scanning or the like are subjected to image quality improving and displayed, some selected (plurality of) tomographic images (for example, two tomographic images at positions symmetrical to each other with respect to a reference line) may each be displayed. In addition, a plurality of tomographic images may be displayed on a display screen for follow-up observation as illustrated in FIG. 23, and an instruction for image quality improvement or an analysis result (for example, the thickness of a specific layer) may be displayed by a similar method as the method described above. Further, image quality improving processing may be executed on a tomographic image based on information stored in a database by the same method as the method described above.

Similarly, in the case of subjecting an SLO fundus image to image quality improving and displaying the resultant image, for example, the SLO fundus image Im2205 may be subjected to image quality improving and displayed. In addition, in the case of subjecting an intensity en-face image to image quality improving and displaying the resultant image, for example, the intensity en-face image Im2209 may be subjected to image quality improving and displayed. In addition, a plurality of SLO fundus images or intensity en-face images may be displayed on a display screen for follow-up observation as illustrated in FIG. 23, and an instruction for image quality improvement or an analysis result (for example, the thickness of a specific layer) may be displayed by a similar method as the method described above. Further, image quality improving processing may be executed on an SLO fundus image or an intensity en-face image based on information stored in a database by the same method as the method described above. Note that, the displays of the tomographic images, SLO fundus images, and intensity en-face images are for illustrative purposes, and these images may be displayed in any form according to a desired configuration. Further, at least two or more of OCTA front images, tomographic images, SLO fundus images and intensity en-face images may be subjected to image quality improving and displayed based on a single instruction.

According to the foregoing configuration, the display controlling unit 350 can display an image which the image quality improving unit 322 or 1622 according to the present modification subjected to image quality improving processing on the display unit 50. At such time, as described above, in the case of a state in which at least one condition is selected among a plurality of conditions relating to the display of high quality images, the display of analysis results, and the depth range of a front image to be displayed and the like, even if the display screen is transitioned to another display screen, the selected state may be maintained.

Further, as described above, in the case of a state in which at least one condition among a plurality of conditions is selected, even if another condition is changed to a selected state, the state in which the at least one condition is selected may be maintained. For example, in a case where a display of analysis results is in a selected state, in response to an instruction from the examiner (for example, when the button 2220 is specified), the display controlling unit 350 may change a display of analysis results for a low quality image to a display of analysis results for a high quality image. Further, in a case where a display of analysis results is in a selected state, in response to an instruction from the examiner (for example, when specification of the button 2220 is released), the display controlling unit 350 may change the display of analysis results for a high quality image to a display of analysis results for a low quality image.

In addition, in a case where a display of a high quality image is in a non-selected state, in response to an instruction from the examiner (for example, when specification of a display of analysis results is released), the display controlling unit 350 may change the display of analysis results for a low quality image to a display of a low quality image. Further, in a case where a display of a high quality image is in a non-selected state, in response to an instruction from the examiner (for example, when the display of analysis results is specified), the display controlling unit 350 may change the display of a low quality image to a display of analysis results for a low quality image. Furthermore, in a case where a display of a high quality image is in a selected state, in response to an instruction from the examiner (for example, when specification of a display of analysis results is released), the display controlling unit 350 may change the display of analysis results for a high quality image to a display of a high quality image. Further, in a case where a display of a high quality image is in a selected state, in response to an instruction from the examiner (for example, when the display of analysis results is specified), the display controlling unit 350 may change the display of a high quality image to a display of analysis results for a high quality image.

Furthermore, let us consider a case where the display of a high quality image is in a non-selected state and a display of a first kind of analysis results is in a selected state. In this case, in response to an instruction from the examiner (for example, when the display of a second kind of analysis results is specified), the display controlling unit 350 may change the display of the first kind of analysis results for a low quality image to a display of the second kind of analysis results for a low quality image. Further, let us consider a case where the display of a high quality image is in a selected state and a display of a first kind of analysis results is in a selected state. In this case, in response to an instruction from the examiner (for example, when the display of a second kind of analysis results is specified), the display controlling unit 350 may change the display of the first kind of analysis results for a high quality image to a display of the second kind of analysis results for a high quality image.

Note that, a configuration may be adopted so that, on the display screen for follow-up observation, as described above, changing of these displays is collectively reflected with respect to a plurality of images obtained at different dates and times. Here, the display of analysis results may be performed such that the analysis results are displayed in a superimposed manner on the images with any degree of transparency. At such time, changing to the display of analysis results may be, for example, a change to a state in which the analysis results are superimposed with any degree of transparency on the images that are being displayed. Further, changing to the display of analysis results may be, for example, a change to the display of images (for example, two-dimensional maps) obtained by subjecting the respective analysis results and images to blending processing with any degree of transparency.

Note that, in the present modification the image quality improving unit 322 or 1622 generates a high quality image by improving the image quality of a tomographic image using an image quality improving model. However, a component that generates a high quality image using an image quality improving model is not limited to the image quality improving units 322 and 1622. For example, a second image quality improving unit that is separate from the image quality improving units 322 and 1622 may be provided, and the second image quality improving unit may generate a high quality image using an image quality improving model. In this case, the second image quality improving unit may generate a high quality image for which an entire image has been subjected to the same image processing, and not a high quality image for which different image processing was performed for each region using a learned model. At such time, the output data of the learned model may be an image obtained by performing the same image quality improving processing on an entire image. Note that, the second image quality improving unit or an image quality improving model that the second image quality improving unit uses may be constituted by a software module that is executed by a processor such as a CPU, an MPU, a GPU or an FPGA, or may be constituted by a circuit that serves a specific function such as an ASIC.

(Modification 9)

The display controlling unit 350 can cause the display unit 50 to display an image selected according to an instruction from the examiner among the high quality images generated by the image quality improving unit 322 or 1622 and the input images. Additionally, the display controlling unit 350 may switch the display on the display unit 50 from an imaged image (input image) to a high quality image, according to an instruction from the examiner. In other words, the display controlling unit 350 may change the display of a low quality image to the display of a high quality image, according to an instruction from the examiner. Additionally, the display controlling unit 350 may change the display of a high quality image to the display of a low quality image, according to an instruction from the examiner.

Further, the image quality improving unit 322 and 1622 may perform the start of the image quality improving processing using an image quality improving model (the input of an image to the image quality improving engine) according to an instruction from the examiner, and the display controlling unit 350 may display the generated high quality image on the display unit 50. In contrast, when an input image is imaged by the imaging apparatus (imaging unit 20), the image quality improving unit 322 and 1622 may automatically generate a high quality image based on the input image by using the image quality improving model, and the display controlling unit 350 may cause the display unit 50 to display the high quality image according to an instruction from the examiner.

Note that these pieces of processing can also be similarly performed on the output of an analysis result. In other words, the display controlling unit 350 may change the display of the analysis result of a low quality image to the display of the analysis result of a high quality image, according to an instruction from the examiner. Additionally, the display controlling unit 350 may change the display of the analysis result of a high quality image to the display of the analysis result of a low quality image, according to an instruction from the examiner. Further, the display controlling unit 350 may change the display of the analysis result of a low quality image to the display of the low quality image, according to an instruction from the examiner. Additionally, the display controlling unit 350 may change the display of a low quality image to the display of the analysis result of the low quality image, according to an instruction from the examiner. Further, the display controlling unit 350 may change the display of the analysis result of a high quality image to the display of the high quality image, according to an instruction from the examiner. In addition, the display controlling unit 350 may change the display of a high quality image to the display of the analysis result of the high quality image, according to an instruction from the examiner.

Further, the display controlling unit 350 may change the display of the analysis result of a low quality image to the display of other kind of analysis result of the low quality image, according to an instruction from the examiner. Additionally, the display controlling unit 350 may change the display of the analysis result of a high quality image to the display of other kind of analysis result of the high quality image, according to an instruction from the examiner.

Here, in the display of the analysis result of a high quality image, the analysis result of the high quality image may be displayed superimposed on the high quality image with arbitrary transparency. Additionally, in the display of the analysis result of a low quality image, the analysis result of the low quality image may be displayed superimposed on the low quality image with arbitrary transparency. At this time, the change to the display of the analysis result may be, for example, the change to a state in which the analysis result is superimposed on the displayed images with arbitrary transparency. Additionally, the change to the display of the analysis result may be, for example, the change to the display of an image (for example, a two-dimensional map) obtained by performing blending processing on the analysis result and the image with arbitrary transparency.

Note that, in the present modification, the image quality improving unit 322 and 1622 generates the high quality image obtained by improving the image quality of the tomographic image by using the image quality improving model. However, the component that generates a high quality image by using the image quality improving model is not limited to the image quality improving unit 322 or 1622. For example, a second image quality improving unit different from the image quality improving unit 322 and 1622 may be provided, and the second image quality improving unit may generate a high quality image by using the image quality improving model. In this case, the second image quality improving unit may generate a high quality image for which the entire image has been subjected to the same image processing, and not a high quality image for which different image processing was performed for each region using a learned model. At such time, the output data of the learned model may be an image obtained by performing the same image quality improving processing on an entire image.

Note that, the second image quality improving unit or an image quality improving model that the second image quality improving unit uses may be constituted by a software module that is executed by a processor such as a CPU, an MPU, a GPU or an FPGA, or may be constituted by a circuit that serves a specific function such as an ASIC.

Additionally, in Modification 8, the image is displayed on which the image quality improving processing has been performed by using the image quality improving model, according to the active state of the button 2220 in the display screen. In contrast, the system may be configured such that, according to the active state of the button 2220, an analysis value using the result of the segmentation processing using the learned model is displayed. In this case, for example, when the button 2220 is in a non-active state (the segmentation processing using the learned model is in a non-selected state), the display controlling unit 350 causes the display unit 50 to display the analysis result using the result of the segmentation processing. In contrast, when the button 2220 is turned into the active state, the display controlling unit 350 causes the display unit 50 to display the analysis result using the result of the segmentation processing using the learned model.

In such a configuration, the analysis result using the result of the segmentation processing that does not use the learned model, and the analysis result using the result of the segmentation processing that uses the learned model are switched and displayed according to the active state of the button. Since these analysis results are respectively based on the results of the processing by the learned model and the image processing by a rule base, there may be a difference in both the results. Therefore, by switching and displaying these analysis results, the examiner can compare the both, and can use a more convincing analysis result for diagnosis.

Note that, when the segmentation processing is switched, for example, in a case where a displayed image is a tomographic image, the numerical value of the layer thickness analyzed for each layer may be switched and displayed. Additionally, for example, when a tomographic image divided into layers by colors, hatching patterns, etc., is displayed, a tomographic image in which the shapes of the layers are changed according to the result of the segmentation processing may be switched and displayed. Further, when a thickness map is displayed as an analysis result, the thickness map in which the color indicating the thickness is changed according to the result of the segmentation processing may be displayed. Additionally, a button for specifying the image quality improving processing and a button for specifying the segmentation processing using the learned model may be separately provided, only either one may be provided, or both the buttons may be provided as one button.

Additionally, similar to the switching of the above-described image quality improving processing, the switching of the segmentation processing may be performed based on information saved (recorded) in the database. Note that, also for the processing at the time of screen transition, the switching of the segmentation processing may be performed similarly to the above-described image quality improving processing.

(Modification 10)

The display controlling unit 350 in the various embodiments and modifications described above may cause analysis results such as the thickness of a desired layer or various blood vessel densities to be displayed on the report screen of the display screen. Further, a parameter value (distribution) relating to a site of interest including at least one of the optic nerve head, the macular area, a vascular zone, a nerve fascicle, a vitreous region, a macular region, a choroid region, a sclera region, a lamina cribrosa region, a retinal layer boundary, a retinal layer boundary edge, a photoreceptor cell, a blood cell, a blood vessel wall, a blood vessel inner wall boundary, a blood vessel external boundary, a ganglion cell, a corneal region, a corner region, and Schlemm's canal and the like may be displayed as an analysis result. At such time, for example, an accurate analysis result can be displayed by analyzing a medical image subjected to various kinds of artifact removal processing. Note that, an artifact may be, for example, a false image region caused by light absorption by a vascular zone or the like, a projection artifact, or a band-like artifact in a front image that arises in the main scanning direction of the measurement light due to the state of the eye to be examined (movement or blinking or the like). Further, an artifact may be of any kind as long as the artifact is an imaging failure region that, for example, randomly arises at each imaging on a medical image of a predetermined site of the subject. Further, the display controlling unit 350 may cause the value (distribution) of a parameter relating to a region including at least one of the various kinds of artifacts (imaging failure regions) described above to be displayed as an analysis result on the display unit 50. Furthermore, the value (distribution) of a parameter relating to a region including at least one abnormal site such as drusen, a neovascular site, leucoma (hard exudates), pseudodrusen or the like may be displayed as an analysis result. Note that, image analysis processing may be performed by the analyzing unit 1924, or may be performed by an analyzing unit that is separate from the analyzing unit 1924. In addition, an image on which image analysis is performed may be an image that was subjected to image quality improving, or may be an image that was not subjected to image quality improving.

An analysis result may be displayed using an analysis map, or using sectors which indicate statistical values corresponding to respective divided regions or the like. Note that, an analysis result may be generated by the analyzing unit 1924 or another analyzing unit using a learned model (analysis result generating engine, or a learned model for generating analysis results) obtained by learning the analysis results of a medical image as training data. At such time, the learned model may be a model obtained by learning using training data including a medical image and an analysis result for the medical image, or training data including a medical image and an analysis result for a medical image of a different kind from the relevant medical image or the like.

Further, the training data may include a region label image generated by the segmentation processing and a result of analyzing a medical image using the aforementioned region label image. In this case, the image processing unit 320, 1620 and 1920, for example, can function as one example of an analysis result generating unit that generates an analysis result with respect to a tomographic image from a result (for example, detection result of retina layers) obtained by executing the segmentation processing using a learned model for generating analysis results. In other words, the image processing units 320, 1620 and 1920 can generate an image analysis result for each different region identified by segmentation processing, by using the learned model for generating analysis results (fourth learned model) that is different from the learned model for generating a high quality image (second medical image).

In addition, a learned model may be a model obtained by learning using training data including input data in which a plurality of medical images of different kinds of a predetermined site, such as an intensity front image and a motion contrast front image, are taken as a set. Here, an intensity front image corresponds to an intensity En-face image, and a motion contrast front image corresponds to an OCTA En-face image.

Further, a configuration may be adopted so as to display an analysis result obtained using a high quality image generated using a learned model for improving image quality. In this case, input data included in the training data may be a high quality image generated using a learned model for improving image quality, or may be a set composed of a low quality image and a high quality image. Note that, the training data may be an image obtained by manually or automatically modifying at least one part of an image that was subjected to image quality improving using a learned model.

Further, the training data may be, for example, data obtained by labeling (annotation) input data for which information including at least one kind of information among an analysis value (for example, an average value or a median value) obtained by analyzing an analysis region, a table including analysis values, an analysis map, and a position of an analysis region such as a sector in an image or the like, is adopted as correct answer data (of supervised learning). Note that, a configuration may be adopted so that an analysis result obtained using a learned model for generating analysis results is displayed according to an instruction from the examiner.

The display controlling unit 350 in the embodiments and modifications described above may cause various kinds of diagnosis results such as results relating to glaucoma or age-related macular degeneration to be displayed on the report screen of the display screen. At such time, for example, an accurate diagnosis result can be displayed by analyzing a medical image subjected to various kinds of artifact removal processing as described above. Further, as the diagnosis result, the position of a specified abnormal site may be displayed on the image, and the state of an abnormal site or the like may be displayed using characters or the like. Further, a classification result (for example. Curtin's classification) for an abnormal site may be displayed as a diagnosis result. Further, as a classification result, for example, information (for example, a numerical value indicating a percentage) that indicates the degree of likelihood for each abnormal site may be displayed. In addition, information that is required so that the physician can confirm the diagnosis may be displayed as a diagnosis result. For example, advice such as to perform additional imaging is conceivable as the aforementioned required information. For example, in a case where an abnormal site is detected in a vascular zone in an OCTA image, information on the effect of advising the physician to additionally perform fluorescence imaging using a contrast medium that enables more detailed observation of blood vessels than by OCTA may be displayed.

Note that, a diagnosis result may be a result generated by the controlling unit 30, 1600 or 1900 using a learned model (diagnosis result generating engine, or a learned model for diagnosis result generation) obtained by learning using diagnosis results for medical images as training data. Further, the learned model may be a model obtained by learning using training data including a medical image and a diagnosis result for the medical image, or training data including a medical image and a diagnosis result for a medical image of a different kind from the relevant medical image or the like.

Furthermore, the training data may include a region label image generated by the segmentation processing and a result of diagnosing a medical image using the aforementioned region label image. In this case, the image processing unit 320, 1620 and 1920, for example, can function as one example of a diagnosis result generating unit that generates a diagnosis result with respect to a tomographic image from a result (for example, detection result of retina layers) obtained by executing segmentation processing using a learned model for diagnosis result generation. In other words, the image processing units 320, 1620 and 1920 can generate a diagnosis result for each different region identified by segmentation processing, by using the learned model for generating diagnosis results (fifth learned model) that is different from the learned model for generating a high quality image (second medical image).

In addition, a configuration may be adopted so as to display a diagnosis result obtained using a high quality image generated using a learned model for improving image quality. In this case, input data included in the training data may be a high quality image generated using a learned model for improving image quality, or may be a set composed of a low quality image and a high quality image. Note that, the training data may be an image obtained by manually or automatically modifying at least one part of an image that was subjected to image quality improving using a learned model.

Further, the training data may be, for example, data obtained by labeling (annotation) input data for which information including at least one kind of information among the diagnosis, a kind or state (extent) of a lesion (abnormal site), the position of a lesion in the image, the position of a lesion relative to a region of interest, the findings (interpretation findings or the like), grounds for the diagnosis (affirmative medical support information or the like), and grounds for negating the diagnosis (negative medical support information) and the like is adopted as correct answer data (of supervised learning). Note that, a configuration may be adopted so that a diagnosis result obtained using a learned model for diagnosis result generation is displayed according to an instruction from the examiner.

Further, the display controlling unit 350 according to the various examples and modifications described above may cause an object recognition result (object detection result) or a segmentation result with respect to a site of interest, an artifact, an abnormal site or the like as described above to be displayed on the report screen of the display screen. At such time, for example, a rectangular frame or the like may be superimposed around an object on the image and displayed. Further, for example, a color or the like may be superimposed on an object in the image and displayed. Note that, an object recognition result or a segmentation result may be a result generated using a learned model (object recognition engine, learned model for object recognition, segmentation engine, or learned model for segmentation) obtained by learning using training data in which information that indicates object recognition or segmentation is labeled (annotated) on a medical image as correct answer data. Note that, the aforementioned analysis result generation or diagnosis result generation may be realized by utilizing the aforementioned object recognition result or segmentation result. For example, processing for generating an analysis result or for generating a diagnosis result may be performed with respect to a site of interest obtained by object recognition processing or segmentation processing.

Further, in the case of detecting an abnormal site, the image processing unit 320, 1620 and 1920 may use a generative adversarial networks (GAN) or a variational auto-encoder (VAE). For example, a DCGAN (Deep Convolutional GAN) that is composed of a generator that is obtained by learning to generate a tomographic image, and a discriminator that is obtained by learning to distinguish between a new tomographic image which the generator generated and a real front image of the ocular fundus can be used as a machine learning model.

In the case of using a DCGAN, for example, the discriminator subjects an input tomographic image to encoding to convert the tomographic image into a latent variable, and the generator generates a new tomographic image based on the latent variable. Thereafter, a difference between the input tomographic image and the new tomographic image that was generated can be extracted as an abnormal site. Further, in the case of using a VAE, for example, an input tomographic image is converted into a latent variable by encoding the tomographic image using an encoder, and a new tomographic image is generated by decoding the latent variable using a decoder. Thereafter, a difference between the input tomographic image and the new tomographic image that was generated can be extracted as an abnormal site. Note that, although an example of input data has been described taking a tomographic image as one example, a fundus image or a front image of the anterior ocular segment or the like may also be used as the input data.

In addition, the image processing units 320, 1620 and 1920 may detect an abnormal site using a convolutional auto-encoder (CAE). In the case of using a CAE, the same image is learned as input data and output data during learning. Thus, when an image in which there is an abnormal site is input to the CAE during estimation, an image is output in which there is no abnormal site according to the learning tendency. Thereafter, a difference between the image input to the CAE and the image output from the CAE can be extracted as an abnormal site. Note that, in this case also, not only a tomographic image, but also a fundus image or a front image of the anterior ocular segment or the like may be used as the input data.

In these cases, the image processing units 320, 1620 and 1920 can generate, as information relating to an abnormal site, information relating to a difference between a medical image obtained using a generative adversarial network or an auto-encoder with respect to each different region identified by segmentation processing or the like, and a medical image input to the generative adversarial network or auto-encoder. Thus, it can be expected that the image processing units 320, 1620 and 1920 will quickly and accurately detect an abnormal site. Here, examples of the auto-encoder include a VAE and a CAE.

Further, in the case of a diseased eye, the image features will differ according to the kind of disease. Therefore, learned models used in the various examples and modifications described above may be generated and prepared for each kind of disease or each abnormal site. In this case, for example, the image processing unit 320 can select a learned model to be used for processing, according to an input (instruction) such as the kind disease or the abnormal site of the eye to be examined from the operator. Note that, a learned model that is prepared for each kind of disease or each abnormal site is not limited to a learned model that is to be used for detecting retina layers or for generating a region label image or the like, and for example may be a learned model that is to be used in an engine for evaluating an image or in an engine for analysis or the like. At such time, the image processing unit 320, 1620 and 1920 may identify the kind of disease or an abnormal site of an eye to be examined from an image using a separately prepared learned model. In this case, the image processing unit 320, 1620 and 1920 can automatically select a learned model to be used in the aforementioned processing based on the kind of disease or the abnormal site that was identified using the separately prepared learned model. Note that, a learned model for identifying the kind of disease or an abnormal site of the eye to be examined can perform learning using pairs of training data for which a tomographic image or a fundus image or the like is adopted as input data, and kinds of diseases or abnormal sites in these images are adopted as ground truth. In this case, with respect to the input data of the training data, a tomographic image or a fundus image or the like may be independently adopted as input data, or a combination of these images may be adopted as input data.

Furthermore, particularly a learned model for diagnosis result generation may be a learned model obtained by learning using training data including input data in which a plurality of medical images of different kinds that are images of a predetermined site of a subject are taken as a set. At such time, for example, data in which a motion contrast front image of the fundus and an intensity front image (or intensity tomographic image) are taken as a set is conceivable as input data included in the training data. Further, for example, input data in which a tomographic image (B-scan image) of the fundus and a color fundus image (or fluorescence fundus image) are taken as a set is conceivable as input data included in the training data. In addition, the plurality of medical images of different kinds may be of any kind as long as the medical images were obtained by different modalities, different optical systems, or different principles or the like.

Further, particularly a learned model for diagnosis result generation may be a learned model obtained by learning using training data including input data in which a plurality of medical images of different sites of a subject are taken as a set. At such time, for example, input data in which a tomographic image (B-scan image) of the fundus and a tomographic image (B-scan image) of the anterior ocular segment are taken as a set is conceivable as input data included in the training data. Further, for example, input data in which a three-dimensional OCT image (three-dimensional tomographic image) of the macula of the fundus and a tomographic image obtained by circular scanning (or raster scanning) of the optic nerve head of the fundus are taken as a set is also conceivable as input data included in the training data.

Note that, the input data included in the training data may be a plurality of medical images of different sites of the subject and of different kinds. At such time, for example, input data in which a tomographic image of the anterior ocular segment and a color fundus image are taken as a set is conceivable as input data included in the training data. Further, the learned model described above may be a learned model obtained by learning using training data including input data in which a plurality of medical images of different imaging angles of view that are images of a predetermined site of the subject are taken as a set. Further, input data included in the training data may be data obtained by joining together a plurality of medical images obtained by time-dividing a predetermined site into multiple regions, such as in the case of a panorama image. At such time, by using a wide-angle image such as a panorama image as training data, the result of processing can be enhanced since there is a probability that a feature value of the image can be obtained with good accuracy for reasons such as the fact that the amount of information is greater than in the case of a narrow-angle image. For example, a configuration is adopted so that, at the time of estimation (the time of prediction), in a case where abnormal sites are detected at a plurality of positions in a wide-angle image, enlarged images of the respective abnormal sites can be sequentially displayed. By this means, since abnormal sites at a plurality of positions can be efficiently checked, for example, the convenience of the examiner can be enhanced. For example, a configuration may be adopted so that, at such time, it is possible for the examiner to select the respective positions on the wide-angle image at which an abnormal site was detected, and to display an enlarged image of the abnormal site at a selected position. Further, input data included in the training data may be input data in which a plurality of medical images obtained at different dates and times of a predetermined site of the subject are taken as a set.

Further, a display screen on which at least one result among an analysis result, a diagnosis result, an object recognition result and a segmentation result described above is to be displayed is not limited to the report screen. Such a display screen may be, for example, at least one display screen among an imaging confirmation screen, a display screen for follow-up observation, and a preview screen for performing various kinds of adjustments before imaging (a display screen on which various kinds of live moving images are displayed) and the like. For example, by causing the aforementioned at least one result obtained using a learned model described above to be displayed on the imaging confirmation screen, the examiner can check an accurate result even immediately after imaging. Further, changing the display between a low quality image and a high quality image as described in Example 9 and the like may be, for example, changing the display between an analysis result for a low quality image and an analysis result for a high quality image.

The various kinds of learned models described above can be obtained by machine learning which uses training data. For example, deep learning which is composed of a multi-level neural network is one kind of machine learning. Further, for example, a convolutional neural network (CNN) can be used for at least a part of a multi-level neural network as a machine learning model. In addition, technology pertaining to auto-encoders may be used for at least a part of a multi-level neural network. Furthermore, technology pertaining to back-propagation (error back-propagation method) may be used for learning. However, the machine learning is not limited to deep learning, and any learning may be employed as long as the learning uses a model that is capable of, by itself, extracting (representing) a feature value of training data such as an image by learning. Here, the term "machine learning model" refers to a learning model according to a machine learning algorithm such as deep learning. Further, the term "learned model" refers to a model which, with respect to a machine learning model according to any machine learning algorithm, trained (performed learning) using appropriate training data in advance. However, it is assumed that the learned model is not a model that does not perform further learning, and is a model that can also perform incremental learning. Further, the term "training data" refers to data composed of pairs of input data and output data (correct answer data). Here, training data is also referred to as "teaching data" in some cases, and there are also cases where correct answer data is referred to as "teaching data".

Note that, a GPU can perform efficient arithmetic operations by performing parallel processing of larger amounts of data. Therefore, in a case where learning is performed a plurality of times using a learning model such as deep learning, it is effective to perform processing with a GPU.

Thus, in the present modification, a GPU is used in addition to a CPU for processing by the image processing units 320, 1620 and 1920 that are an example of a learning unit (not illustrated). Specifically, when a learning program including the learning model is executed, learning is performed by the CPU and the GPU cooperating to perform arithmetic operations. Note that, with respect to the processing of the learning unit, arithmetic operations may be performed by only the CPU or the GPU. Further, a processing unit (estimating unit) that executes processing using the various learned models described above may also using a GPU, similarly to the learning unit. The learning unit may also include an error detecting unit and an updating unit (not illustrated). The error detecting unit obtains an error between output data that is output from the output layer of the neural network according to input data that is input to the input layer, and correct answer data. The error detecting unit may be configured to calculate an error between the output data from the neural network and the correct answer data using a loss function. Further, based on an error obtained by the error detecting unit, the updating unit updates combining weighting factors between nodes of the neural network or the like so that the error becomes small. The updating unit updates the combining weighting factors or the like using, for example, the error back-propagation method. The error back-propagation method is a method that adjusts combining weighting factors between the nodes of each neural network or the like so that the aforementioned error becomes small.

Further, a U-Net type machine learning model that has a function of an encoder that is composed of a plurality of levels including a plurality of downsampling layers, and a function of a decoder that is composed of a plurality of levels including a plurality of upsampling layers can be applied as a machine learning model to be used for image quality improving or segmentation or the like. In a U-Net type machine learning model, positional information (spatial information) that has been made ambiguous in a plurality of levels configured as an encoder is configured (for example, using a skip connection) so that the information can be used in levels of the same dimension (levels corresponding to each other) in a plurality of levels configured as a decoder.

In addition, for example, an FCN (fully convolutional network) or a SegNet or the like can also be used as a machine learning model to be used for image quality improving or segmentation or the like. Further, a machine learning model that performs object recognition in region units may be used according to a desired configuration. As a machine learning model that performs object recognition, for example, RCNN (Region CNN), Fast-RCNN, or Faster-RCNN can be used. In addition, YOLO (You Only Look Once) or SSD (Single Shot Detector, or Single Shot Multi-Box Detector) can also be used as a machine learning model that performs object recognition in region units.

Further, the machine learning model may be, for example, a capsule network (CapsNet). In this case, in a common neural network, by configuring each unit (each neuron) so as to output a scalar value, the neural network is configured so that, for example, spatial information relating to spatial positional relationships (relative positions) between features in an image is reduced. By this means, for example, learning can be performed in which the influence of local distortion or parallel displacement in an image is reduced. On the other hand, in a capsule network, each unit (each capsule) is configured so as to output spatial information as a vector, and for example, is configured so that spatial information is held. By this means, for example, learning can be performed in which spatial positional relationships (relative positions) between features in an image is taken into consideration.

Furthermore, the image quality improving model (learned model for improving image quality) may be a learned model obtained by incremental learning using training data including at least one high quality image generated by an image quality improving model. At such time, a configuration may be adopted that enables a selection as to whether a high quality image is to be used as training data for incremental learning to be made by an instruction from the examiner. Note that, these configurations are not limited to a learned model for improving image quality, and are also applicable to various kinds of learned models described above. Further, a learned model for generating correct answer data which generates correct answer data such as labeling (annotation) may be used to generate correct answer data used for learning by the various kinds of learned models described above. At such time, the learned model for generating correct answer data may be a learned model obtained by performing (sequential) incremental learning of correct answer data obtained when the examiner performed labeling (annotation). In other words, the learned model for generating correct answer data may be a learned model obtained by performing incremental learning of training data in which data before labeling is adopted as input data, and data after labeling is adopted as output data. Further, in the case of a plurality of consecutive frames such as a moving image, a configuration may also be adopted so as to modify a result with respect to a frame for which it is determined that the accuracy of the result is low taking into account the results of object recognition or segmentation of the preceding and following frames. At such time, a configuration may be adopted so as to perform incremental learning of the modified result as correct answer data in accordance with an instruction from the examiner.

Note that, in the various embodiments and modifications described above, in a case where regions of an eye to be examined are detected using a learned model for object recognition or a learned model for segmentation, predetermined image processing can also be performed for each detected region. For example, let us consider a case of detecting at least two regions among a vitreous body region, a retina region and a choroid region. In this case, when performing image processing such as contrast adjustment with respect to the at least two regions that were detected, adjustment that is suitable for the respective regions can be performed by using different image processing parameters for the respective regions. By displaying an image on which adjustment suitable for the respective regions was performed, the operator can more appropriately diagnose a disease or the like in each region. Note that, with regard to a configuration that uses image processing parameters that differ for each detected region, for example, such a configuration may also be similarly applied with respect to regions of an eye to be examined which were detected without using a learned model.

(Modification 11)

A configuration may be adopted so that, on a preview screen in the various examples and modifications described above, a learned model for improving image quality described above is used for every at least one frame of a live moving image. At such time, a configuration may be adopted so that, in a case where a plurality of live moving images of different sites or different kinds are displayed on the preview screen, learned models that correspond to the respective live moving images are used. By this means, for example, since the processing time can be shortened even for a live moving image, the examiner can obtain highly accuracy information prior to the start of imaging. Therefore, for example, since failures of re-imaging and the like can be reduced, the accuracy and efficiency of diagnosis can be improved.

Note that, the plurality of live moving images may include, for example, a moving image of the anterior ocular segment for alignment in the XYZ-directions, and a front moving image of the fundus for OCT focus adjustment or focus adjustment of a fundus observation optical system. Further, the plurality of live moving images may also include, for example, a tomographic moving image of the fundus for coherence gate adjustment in OCT (adjustment of the optical path length difference between the measurement optical path length and the reference optical path length) and the like. At such time, a configuration may be adopted so that various kinds of adjustment mentioned above are performed so that a region detected using the learned model for object recognition or learned model for segmentation as described above satisfies a predetermined condition. For example, a configuration may be adopted so that various kinds of adjustment such as OCT focus adjustment are performed so that a value (for example, a contrast value or an intensity value) relating to a vitreous body region or a predetermined retinal layer such as the RPE that was detected using the learned model for object recognition or learned model for segmentation exceeds a threshold value (or becomes a peak value). Further, for example, a configuration may be adopted so that coherence gate adjustment in OCT is performed so that a vitreous body region or a predetermined retinal layer such as the RPE that was detected using the learned model for object recognition or learned model for segmentation is at a predetermined position in the depth direction.

In these cases, the image quality improving unit 322 or 1622 can use a learned model to perform image quality improving processing with respect to a moving image to thereby generate a high quality moving image. Further, in a state in which the high quality moving image is displayed, the drive controlling unit 330 can perform drive control of an optical member that changes an imaging range of the reference mirror 221 or the like so that any one of the different regions identified by the segmentation processing or the like is located at a predetermined position in the display region. In such a case, the controlling unit 30, 1600 or 1900 can automatically perform alignment processing based on highly accurate information so that a desired region is located at a predetermined position in the display region. Note that, the optical member that changes the imaging range may be, for example, an optical member that adjusts the coherence gate position, and specifically may be the reference mirror 221 or the like. Further, the coherence gate position can be adjusted by an optical member that changes the optical path length difference between the measurement optical path length and the reference optical path length, and the optical member in question may be, for example, a mirror (not illustrated) or the like for changing the optical path length of the measuring light. Note that, the optical member that changes the imaging range may also be, for example, the stage unit 25.

Furthermore, a moving image to which a learned model described above can be applied is not limited to a live moving image, and for example the moving image may be a moving image stored (saved) in the storage. At such time, for example, a moving image obtained by performing alignment with respect to every at least one frame of a tomographic moving image of the fundus stored (saved) in the storage may be displayed on the display screen. For example, in a case where it is desired to suitably observe the vitreous body region, first, a reference frame based on conditions such as that the vitreous body region is present as much as possible in the frame may be selected. At such time, each frame is a tomographic image (B-scan image) in the X-Z direction. Subsequently, a moving image in which other frames have been aligned in the X-Z direction with respect to the selected reference frame may be displayed on the display screen. At such time, for example, a configuration may be adopted so as to cause high quality images (high image quality frames) sequentially generated using a learned model for improving image quality for every at least one frame of the moving image to be consecutively displayed.

Note that, as methods for performing alignment among frames described above, the same method may be applied with respect to the method for performing alignment in the X-direction and the method for performing alignment in the Z-direction (depth direction), or the methods that are applied may all be different. In addition, alignment in the same direction may be performed a plurality of times by different methods. For example, a rough alignment may be performed, and thereafter a fine alignment may be performed. Further, as a method for alignment, for example, a method is available that performs (rough Z-direction) alignment using a retinal layer boundary obtained by subjecting a tomographic image (B-scan image) to segmentation processing. In addition, as a method for alignment, for example, a method is also available that performs (fine X-direction or Z-direction) alignment using correlation information (similarity) between a plurality of regions obtained by dividing a tomographic image and a reference image. As further methods for alignment, for example, a method is available that performs (X-direction) alignment using a one-dimensional projection image generated for each tomographic image (B scan image), and a method is available that performs (X-direction) alignment using a two-dimensional front image generated for each tomographic image (B scan image) and the like. Further, a configuration may be adopted so as to perform fine alignment in sub-pixel units after rough alignment was performed in pixel units.

In this case there is a probability that, during various kinds of adjustment, the imaging target such as the retina of the eye to be examined could not yet be successfully imaged. Thus, since there is a large difference between the medical image input to the learned model and the medical image used as training data, there is a probability that a high quality image was not accurately obtained. Therefore, a configuration may be adopted so that when an evaluation value such as a value obtained when the image quality of a tomographic image (B scan) is evaluated exceeds a threshold value, display of a high-quality moving image (consecutive display of high image quality frames) is automatically started. Further, a configuration may be adopted so that when an evaluation value such as a value obtained when the image quality of a tomographic image (B scan) is evaluated exceeds a threshold value, the image quality improving button is changed to a state (active state) in which the button can be designated by the examiner.

Further, a configuration may be adopted in which different learned model for improving image quality are prepared for each imaging mode for which scanning patterns or the like are different, and learned model for improving image quality that corresponds to a selected imaging mode is selected. Further, one learned model for improving image quality obtained by learning using training data including various medical images obtained in different imaging modes may be used.

(Modification 12)

In the various examples and modifications described above, in a case where various kinds of learned model are undergoing incremental learning, there is a probability that it will be difficult to output (infer/predict) using a learned model which is undergoing incremental learning itself. Therefore, input of a medical image to a learned model which is undergoing incremental learning may be prohibited. Further, a learned model that is the same as a learned model which is undergoing incremental learning may be prepared as another auxiliary learned model. At such time, a configuration may be adopted so that input of a medical image to the auxiliary learned model can be executed while incremental learning is being performed. Subsequently, after the incremental learning is completed, the learned model which underwent the incremental learning is evaluated, and if there is no problem, it suffices to switch from the auxiliary learned model to the learned model which underwent the incremental learning. Further, a configuration may be adopted so that the auxiliary learned model is used if there is a problem.

Further, a configuration may be adopted so that learned models obtained by learning for respective imaged sites can be selectively utilized. Specifically, a plurality of learned models can be prepared that include a first learned model obtained using training data including a first imaged site (lung, eye to be examined, or the like), and a second learned model obtained using training data including a second imaged site that is different from the first imaged site. Further, the image processing unit 320, 1620 and 1920 may have a selecting unit for selecting any one of this plurality of learned models. At such time, the image processing unit 320, 1620 and 1920 may have a control unit for executing incremental learning with respect to a selected learned model. The control unit can, in accordance with an instruction from the examiner, retrieve data in which an imaged site corresponding to a selected learned model and an image obtained by imaging the relevant imaged site form a pair, and execute learning in which the retrieved and obtained data is adopted as training data, as incremental learning with respect to the selected learned model. Note that, an imaged site corresponding to a selected learned model may be a site obtained based on header information of data, or a site that is manually input by the examiner. Further, retrieval of data may be performed, for example, through a network from a server or the like of an external facility such as a hospital or a laboratory. By this means, incremental learning can be efficiently performed for each imaged site by using an image obtained by imaging an imaged site that corresponds to the learned model.

Note that, the selecting unit and the control unit may be constituted by a software module that is executed by a processor such as an MPU or a CPU of the controlling unit 30, 1600 or 1900. Further, the selecting unit and the control unit may be constituted by a circuit that serves a specific function such as an ASIC or by an independent apparatus or the like.

Further, when obtaining training data for incremental learning through a network from a server or the like of an external facility such as a hospital or a laboratory, it is useful to reduce a decrease in reliability due to falsification or system trouble during incremental learning or the like. Therefore, the correctness of the training data for incremental learning may be detected by confirming the consistency by a digital signature or hashing. By this means the training data for incremental learning can be protected. At such time, in a case where the correctness of the training data for incremental learning could not be detected as the result of confirming the consistency by a digital signature or hashing, a warning to that effect is given and incremental learning is not performed using the training data in question. Note that, the server may be any form of server, such as a cloud server, a FOG server, or an edge server, regardless of the installation location thereof.

(Modification 13)

In the various examples and modifications described above, an instruction from the examiner may be a voice instruction or the like in addition to a manual instruction (for example, an instruction using a user interface or the like). At such time, for example, a machine learning model including a speech recognition model (a speech recognition engine or a learned model for speech recognition) obtained by machine learning may be used. In addition, a manual instruction may be an instruction by character input using a keyboard, a touch panel, or the like. At such time, for example, a machine learning model including a character recognition model (a character recognition engine or a learned model for character recognition) obtained by machine learning may be used. Further, an instruction from the examiner may be an instruction by a gesture or the like. At such time, a machine learning model including a gesture recognition model (a gesture recognition engine or a learned model for gesture recognition) obtained by machine learning may be used.

Further, an instruction from the examiner may be a result of detection of the line of sight of the examiner on a display screen of the display unit 50. The line-of-sight detection result may be, for example, a pupil detection result using a moving image of the examiner obtained by imaging from around the display screen of the display unit 50. At such time, the pupil detection from the moving image may use an object recognition engine as described above. Further, an instruction from the examiner may be an instruction by brain waves, or a faint electric signal flowing through the body or the like.

In such a case, for example, the training data may be training data in which character data or voice data (waveform data) or the like indicating an instruction to display a result obtained by processing of various learned models as described above is adopted as input data, and an execution command for causing a result obtained by processing of various learned models to be actually displayed on a display unit is adopted as correct answer data. Further, the training data may be training data in which, for example, character data or voice data or the like indicating an instruction to display a high quality image obtained with a learned model for improving image quality is adopted as input data, and an execution command for displaying a high quality image and an execution command for changing the button 2220 as illustrated in FIG. 22A and FIG. 22B to an active state are adopted as correct answer data. Note that, any kind of training data may be used as long as, for example, the instruction content indicated by the character data or voice data or the like and the execution command content correspond with each other. Further, voice data may be converted to character data using an acoustic model or a language model or the like. Further, processing that reduces noise data superimposed on voice data may be performed using waveform data obtained with a plurality of microphones. Further, a configuration may be adopted so that a selection between an instruction issued by characters or voice or the like and an instruction input using a mouse or a touch panel or the like can be made according to an instruction from the examiner. In addition, a configuration may be adopted so that a selection can be made to turn instruction by characters or voice or the like on or off according to an instruction from the examiner.

In this case, the machine learning includes deep learning as described above, and for example, a recurrent neural network (RNN) can be used as at least a part of the multi-layer neural network. Here, as an example of the machine learning model according to the present modification, an RNN that is a neural network that handles time-series information will be described with reference to FIGS. 24A and 24B. Further, a long short-term memory (hereinafter referred to as an "LSTM"), which is a kind of RNN, will be described with reference to FIG. 25A and FIG. 25B.

Figure 24A:
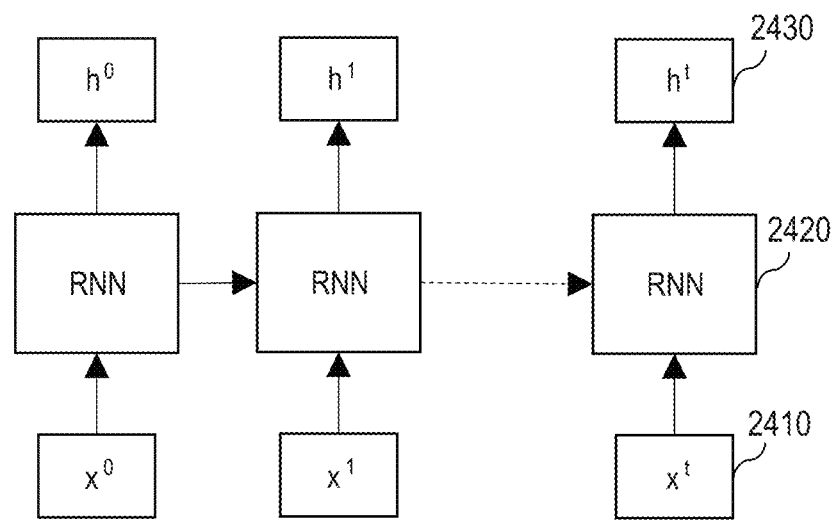
FIG. 24A is a view illustrating an example of a configuration of a neural network used as a machine learning model according to Modification 13.
Figure 24B:
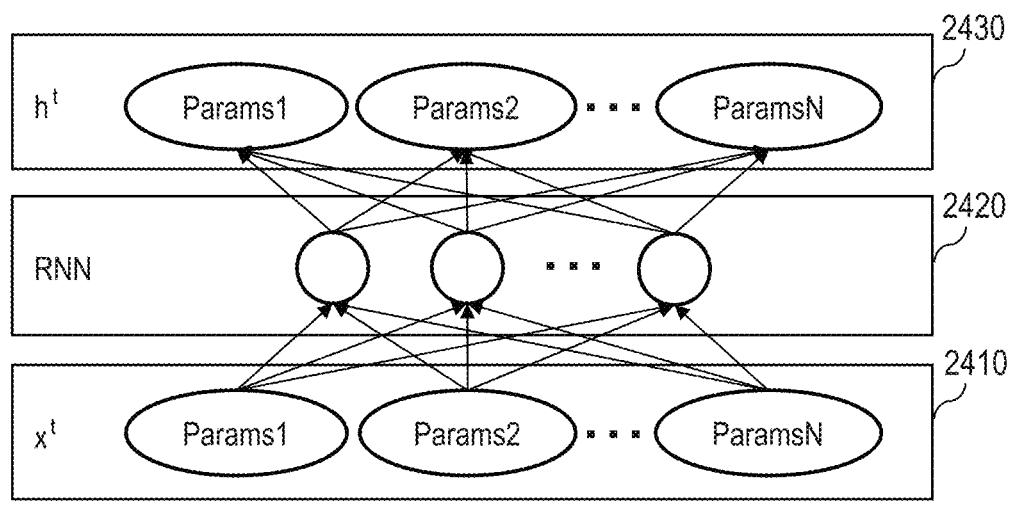
FIG. 24B is a view illustrating an example of the configuration of the neural network used as the machine learning model according to Modification 13.

FIG. 24A illustrates a structure of an RNN that is a machine learning model. An RNN 2420 has a loop structure in the network, and data $x^t$ 2410 is input to the RNN 2420 at time t, and the RNN 2420 outputs data $h^t$ 2430. Since the RNN 2420 has a loop function in the network, the state at the current time can be taken over to the next state, and hence time-series information can be handled. FIG. 24B illustrates an example of the input/output of parameter vectors at time t. The data $x^t$ 2410 includes N pieces of data (Params 1 to Params N). Further, the data $h^t$ 2430 output by the RNN 2420 includes N pieces of data (Params 1 to Params N) corresponding to the input data.

Figure 25A:
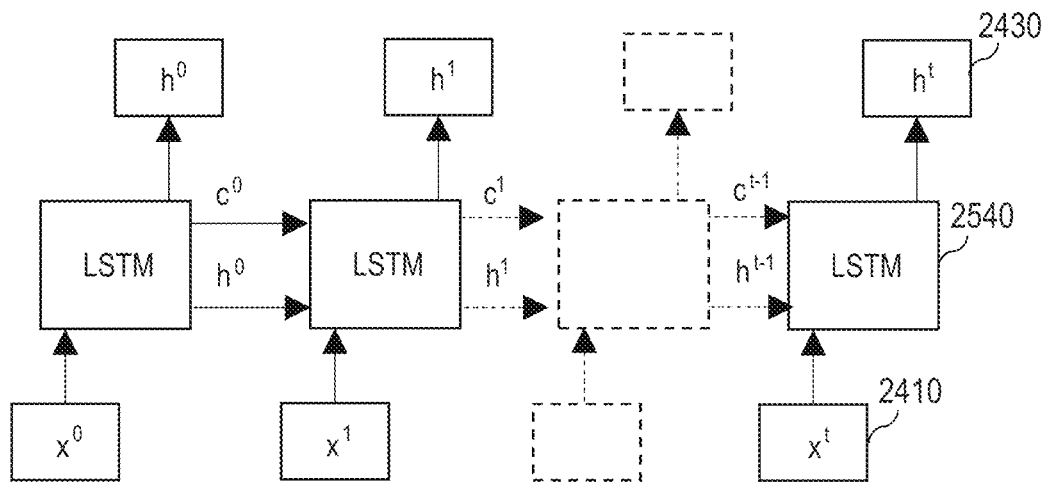
FIG. 25A is a view illustrating an example of the configuration of the neural network used as the machine learning model according to Modification 13.

However, since the RNN cannot handle long-term information during back propagation, the LSTM may be used. The LSTM can learn long-term information by providing a forget gate, an input gate, and an output gate. FIG. 25A illustrates a structure of the LSTM. In an LSTM 2540, information that the network takes over at the next time t is an internal state $c^{t-1}$ of the network called a cell and output data $h^{t-1}$. Note that lowercase letters (c, h, x) in the figure represent vectors.

Figure 25B:
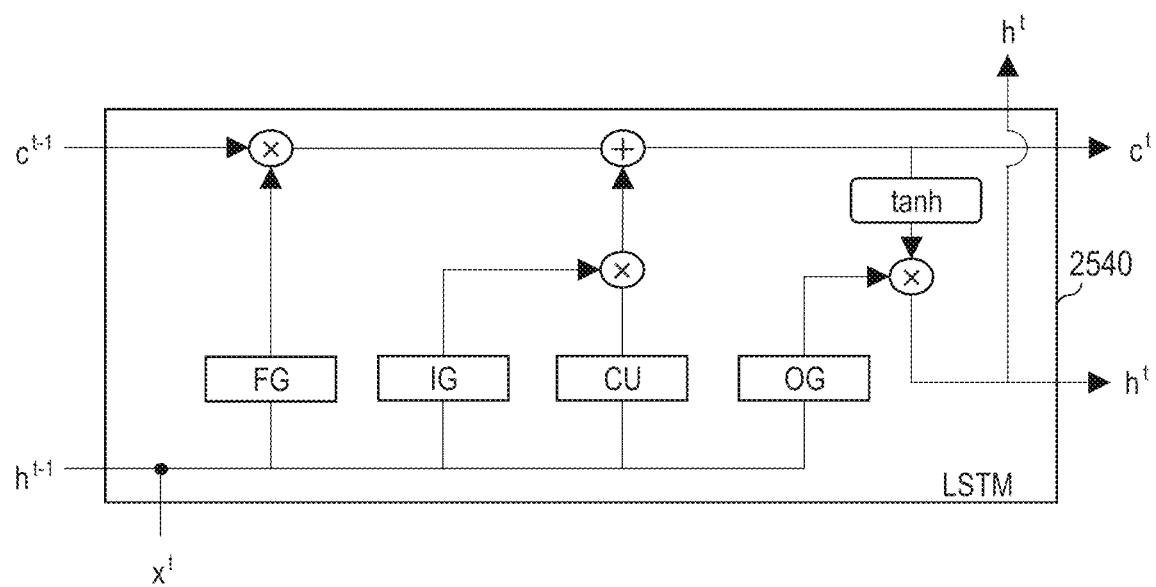
FIG. 25B is a view illustrating an example of the configuration of the neural network used as the machine learning model according to Modification 13.

Next, the LSTM 2540 is illustrated in detail in FIG. 25B. A forget gate network FG, an input gate network IG and an output gate network OG are illustrated in FIG. 25B, and each of these networks is a sigmoid layer. Therefore, a vector in which each element has a value from 0 to 1 is output. The forget gate network FG determines how much past information is held, and the input gate network IG determines which value is to be updated. A cell update candidate network CU is also illustrated in FIG. 25B, and the cell update candidate network CU is an activation function tan h layer. This creates a vector of new candidate values to be added to the cell. The output gate network OG selects an element of a cell candidate and selects how much information is to be transmitted at the next time.

Note that, the LSTM model described above is a basic form, and the present invention is not limited to the network illustrated here. The coupling between networks may be changed. A QRNN (quasi-recurrent neural network) may be used instead of an LSTM. In addition, the machine learning model is not limited to a neural network, and Boosting or Support Vector Machine or the like may be used. Further, in a case where an instruction from the examiner is input by characters or voice or the like, a technique relating to natural language processing (for example, Sequence to Sequence) may be applied. Further, a dialogue engine (a dialogue model or a learned model for dialogue) that responds to the examiner with an output such as text or voice may be applied.

(Modification 14)

In the various examples and modifications described above, a high quality image, a label image or the like may be stored in the storage in accordance with an instruction from the operator. At such time, for example, after an instruction from the operator to save a high quality image, when registering a file name, a file name that includes information (for example, characters) indicating that the image is an image generated by processing using a learned model for improving image quality (image quality improving processing) at any part of the file name (for example, the first part or the last part) may be displayed as a recommended file name in a state in which the file name can be edited according to an instruction from the operator. Note that, with respect to a boundary image or a region label image or the like also, a file name including information indicating that the image is an image generated by processing using a learned model may be displayed in a similar manner.

Further, when causing the display unit 50 to display a high quality image on various display screens such as the report screen, a display indicating that the image being displayed is a high quality image generated by processing using a learned model for improving image quality may be displayed together with the high quality image. In this case, since the operator can easily discern by the relevant display that the displayed high quality image is not the actual image obtained by imaging, misdiagnosis can be reduced and the diagnosis efficiency can be improved. Note that, a display indicating that a high quality image was generated by processing that used a learned model for improving image quality may be of any form as long as it is a display which makes it possible to distinguish between the input image and the high quality image generated by the relevant processing. Further, with regard to processing using various learned models as described above also, and not just processing using a learned model for improving image quality, a display indicating that the result being displayed was generated by processing using the relevant kind of learned model may be displayed together with the relevant result. Further, when displaying an analysis result with respect to segmentation results obtained using a learned model for segmentation processing also, a display indicating that the analysis result is based on results obtained using a learned model for segmentation may be displayed together with the analysis result.

At such time, the display screen such as a report screen may be stored in the storage as an image data in accordance with an instruction from the operator. For example, a report screen may be stored in the storage as a single image in which high quality images or the like and a display indicating that these images are images generated by processing using a learned model are displayed side by side.

Further, with respect to the display indicating that a high quality image was generated by processing that used a learned model for improving image quality, a display indicating what kind of training data the learned model for improving image quality used when performing learning may be displayed on the display unit. The display in question may include a display of a description of the kinds of input data and correct answer data of the training data, or any display relating to the input data and the correct answer data such as an imaged site included in the correct answer data. Note that, with regard to processing using the various kinds of learned models as described above such as segmentation processing also, a display indicating what kind of training data the relevant kind of learned model used when performing learning may be displayed on the display unit.

A configuration may also be adopted so that information (for example, characters) indicating that an image was generated by processing using a learned model is displayed or stored in a state in which the information is superimposed on the image or the like. At such time, a place at which the information is superimposed on the image may be any place as long as the place is in a region (for example, at an edge of the image) which does not overlap with a region in which the site of interest or the like that is the imaging target is displayed. Further, a non-overlapping region may be determined, and the information may be superimposed in the determined region. Note that, processing may be performed in a similar manner with respect to, for example, an image obtained by processing that used the various kinds of learned models described above such as segmentation processing, and not just processing that used a learned model for improving image quality.

Further, a configuration may be adopted so that in a case where, as an initial display screen of the report screen, the default setting is set so that the button 2220 as illustrated in FIG. 22A and FIG. 22B enters an active state (image quality improving processing is set to "on"), a report image corresponding to the report screen that includes a high quality image or the like is transmitted to a server in accordance with an instruction from the examiner. Further, a configuration may be adopted so that in a case where the default setting is set so that the button 2220 enters an active state, when an examination ends (for example, in a case where the imaging confirmation screen or the preview screen is changed to the report screen in accordance with an instruction from the examiner), a report image corresponding to the report screen that includes a high quality image or the like is (automatically) transmitted to a server. At such time, a configuration may be adopted so that a report image generated based on various kinds of settings of the default settings (for example, settings relating to at least one of the depth range for generating an en-face image on the initial display screen of the report screen, whether or not to superimpose an analysis map, whether or not the image is a high quality image, and whether or not to show a display screen for follow-up observation and the like) is transmitted to a server. Note that, similar processing may be performed in relation to a case where the button 2220 represents switching of segmentation processing also.

(Modification 15)

In the various examples and modifications described above, among the aforementioned various kinds of learned models, an image obtained with a first kind of learned model (for example, a high quality image, an image showing an analysis result such as an analysis map, an image showing an object recognition result or an image showing a segmentation result) may be input to a second kind of learned model that is different from the first kind. At such time, a configuration may be adopted so that a result (for example, an analysis result, a diagnosis result, an object recognition result or a segmentation result) is generated by processing of the second kind of learned model.

Further, among the various kinds of learned models described above, an image to be input to a second kind of learned model that is different from a first kind of learned model may be generated from an image input to the first kind of learned model by using a result (for example, an analysis result, a diagnosis result, an object recognition result or a segmentation result) obtained by processing of the first kind of learned model. At such time, there is a high probability that the generated image is an image that is suitable as an image for processing using the second kind of learned model. Therefore, the accuracy of an image (for example, a high quality image, an image showing an analysis result such as an analysis map, an image showing an object recognition result or an image showing a segmentation result) obtained when the generated image is input to the second kind of learned model can be enhanced.

Further, retrieval of similar case images utilizing an external database that is stored in a server or the like may be performed using, as a search key, an analysis result or a diagnosis result or the like obtained by processing of a learned model that is described above. Note that, in a case where a plurality of images stored in the database are already being managed in a state in which respective feature values of the plurality of images have been attached as supplementary information by machine learning or the like, a similar case image search engine (a similar case image search model, or a learned model for similar case image searching) that utilizes an image itself as a search key may be used. For example, the image processing units 320, 1620 and 1920 can perform a search for a similar case image with respect to each different region identified by segmentation processing or the like, by using a learned model for similar case image searching (sixth learned model) that is different from the learned model for generating a high quality image (second medical image).

(Modification 16)

Note that, processing for generating motion contrast data in the aforementioned examples and modifications is not limited to a configuration in which processing is performed based on intensity values of a tomographic image. The various kinds of processing described above may be applied with respect to an interference signal obtained with the imaging unit 20, a signal obtained by subjecting an interference signal to Fourier transformation, a signal obtained by subjecting the relevant signal to any processing, and tomographic data including a tomographic image or the like based on these signals. In these cases also, similar effects as the effects of the aforementioned configurations can be obtained.

Further, image processing such as gradation conversion processing in the aforementioned embodiments and modifications is not limited to a configuration in which the processing is performed based on intensity values of a tomographic image. The various kinds of processing described above may be applied with respect to tomographic data including an interference signal obtained with the imaging unit 20, a signal obtained by subjecting an interference signal to Fourier transformation, and a signal obtained by subjecting the relevant signal to any processing or the like. In these cases also, similar effects as the effects of the aforementioned configurations can be obtained.

In addition, while a spectral domain OCT (SD-OCT) apparatus which uses the SLD as a light source is described as the OCT apparatus in the foregoing examples and modifications, the configuration of the OCT apparatus according to the present invention is not limited thereto. For example, the present invention can also be applied to a swept source OCT (SS-OCT) apparatus which uses a wavelength swept light source capable of sweeping a wavelength of emitted light, or any other kind of OCT apparatus. Further, the present invention can also be applied to a Line-OCT apparatus (or SS-Line-OCT apparatus) that uses line light. Furthermore, the present invention can also be applied to a Full Field-OCT apparatus (or SS-Full Field-OCT apparatus) that uses area light.

Further, although in the aforementioned examples and modifications an optical fiber optical system that uses a coupler as a splitting unit is used, a spatial optical system that uses a collimator and a beam splitter may also be used. Further, the configuration of the imaging unit 20 is not limited to the above-described configuration, and some of the components included in the imaging unit 20 may be provided as separate components from the imaging unit 20.

Furthermore, in the aforementioned examples and modifications, the obtaining unit 310 obtains an interference signal that was obtained by the imaging unit 20, a tomographic image generated by an image processing unit 320, or the like. However, a configuration with which the obtaining unit 310 obtains these signals or images is not limited to the above-described configuration. For example, the obtaining unit 310 may obtain these signals from a server or imaging apparatus connected to the controlling unit 30, 1600 or 1900 through a LAN, a WAN, or the Internet or the like.

Further, the learning data of the various kinds of learned models is not limited to data obtained using the ophthalmic apparatus itself that performs the actual imaging, and according to a desired configuration, the learning data may be data obtained using an ophthalmic apparatus of the same model, or may be data obtained using an ophthalmic apparatus of the same kind.

Note that, the various kinds of learned models according to the above embodiments and modifications can be provided in the controlling units 30, 1600 and 1900. These learned models, for example, may be constituted by a software module that is executed by a processor such as a CPU, an MPU, a GPU or an FPGA, or may be constituted by a circuit that serves a specific function such as an ASIC. Further, these learned models may be provided in a different apparatus such as a server that is connected to the controlling unit 30, 1600 or 1900. In this case, the controlling unit 30, 1600 or 1900 can use the learned models by connecting to the server or the like that includes the learned models through any network such as the Internet. The server that includes the learned models may be, for example, a cloud server, a FOG server, or an edge server.

Note that, although a tomographic image relating to the fundus portion of an eye to be examined is described in the above embodiments and modifications, the image processing described above may also be performed with respect to a tomographic image relating to the anterior ocular segment of an eye to be examined. In this case, regions such as the crystalline lens, cornea, iris and anterior chamber are included in regions to be subjected to different image processing in the tomographic image. Note that, the regions in question may also include other regions of the anterior ocular segment. Furthermore, the regions with respect to a tomographic image relating to the fundus portion are not limited to the vitreous body portion, the retina portion and the choroid portion, and may also include other regions relating to the fundus portion. In this regard, since the gradation range of a tomographic image relating to the fundus portion is wider than that of a tomographic image relating to the anterior ocular segment, the image quality improving by image processing according to the above embodiments and modifications can be performed more effectively.

Further, although an eye to be examined is described as an example of a subject in the above embodiments and modifications, a subject is not limited thereto. For example, a subject may be skin or another organ. In this case, the OCT apparatus according to the above embodiments and modifications can be applied in a medical instrument other than an ophthalmic apparatus, such as an endoscope.

(Modification 17)

Further, images to be processed by an image processing apparatus or image processing method according to the various examples and modifications described above include medical images obtained using an arbitrary modality (imaging apparatus or imaging method). The medical images to be processed can include a medical image obtained by any imaging apparatus or the like, and images created by an image processing apparatus or an image processing method in accordance with the examples and modifications described above.

In addition, a medical image to be processed is an image of a predetermined site of a subject (examinee), and the image of the predetermined site includes at least one part of the predetermined site of the subject. The medical image may also include another site of the subject. The medical image may be a still image or a moving image, and may be a black and white image or a color image. In addition, the medical image may be an image representing the structure (form) of the predetermined site or may be an image representing a function of the predetermined site. Images that represent a function include, for example, an image representing hemodynamics (blood flow volume, blood flow velocity or the like) such as an OCTA image, a Doppler OCT image, an fMRI image, and an ultrasound Doppler image. Note that, the predetermined site of the subject may be determined according to the imaging target, and the predetermined site includes any site such as an organ such as the human eye (eye to be examined), brain, lung, intestine, heart, pancreas, kidney, and liver, and the head, chest, legs and arms.

Further, the medical image may be a tomographic image of the subject, or may be a front image. Examples of a front image include a front image of the ocular fundus, a front image of the anterior ocular segment, a fundus image obtained by fluorescence imaging, and an en-face image generated using at least a partial range of data in the depth direction of the imaging target with respect to data obtained by OCT (three-dimensional OCT data). Note that, an en-face image may be an OCTA en-face image (motion contrast front image) generated using at least a partial range of data in the depth direction of the imaging target with respect to three-dimensional OCTA data (three-dimensional motion contrast data). Further, three-dimensional OCT data or three-dimensional motion contrast data is an example of three-dimensional medical image data.

Here, the term "motion contrast data" refers to data showing changes between a plurality of items of volume data obtained by controlling so that measuring light is scanned a plurality of times over the same region (same position) of an eye to be examined. At such time, the volume data is composed of a plurality of tomographic images obtained at different positions. The motion contrast data can then be obtained as volume data by, at respective positions that are different to each other, obtaining data showing changes between a plurality of tomographic images that were obtained at approximately the same position. Note that, in relation to OCT angiography (OCTA) that measures blood flow movement, a motion contrast front image is also referred to as an OCTA front image (OCTA en-face image), and motion contrast data is also referred to as OCTA data. The motion contrast data can be obtained, for example, as a variance value or a decorrelation value between two tomographic images or between interference signals corresponding to the two tomographic images, or as a value obtained by dividing a maximum value by a minimum value (maximum value/minimum value), and may be obtained by any known method. At such time, the two tomographic images can be obtained, for example, by controlling so that measuring light is scanned a plurality of times over the same region (same position) of the eye to be examined.

Further, an en-face image is, for example, a front image generated by projecting data of a range between two layer boundaries in the X- and Y-directions. At such time, the front image is generated by projecting or integrating data corresponding to a depth range that is at least a partial depth range of volume data (a three-dimensional tomographic image) obtained using light interference and that is defined based on two reference planes onto a two-dimensional plane. The en-face image is a front image generated by, among volume data, projecting data corresponding to a depth range which is determined based on detected retinal layers onto a two-dimensional plane. Note that, as a technique for projecting data corresponding to a depth range defined based on two reference planes onto a two-dimensional plane, for example, a technique can be used in which representative values of data within the relevant depth range are adopted as pixel values on a two-dimensional plane. In this case, the representative values can include values such as an average value, a median value or a maximum value of pixel values within a range in the depth direction of the region surrounded by the two reference planes. Further, the depth range pertaining to the en-face image may be, for example, a range that includes only a range corresponding to a predetermined number of pixels in a deeper direction or a shallower direction with reference to one of the two layer boundaries relating to the detected retinal layers. In addition, the depth range pertaining to the en-face image may be, for example, a range that has been changed (offset) according to an instruction of the operator from a range between the two layer boundaries relating to the detected retinal layers.

In addition, the term "imaging apparatus" refers to an apparatus for performing imaging to obtain an image to be used for diagnosis. Examples of an imaging apparatus include an apparatus that obtains an image of a predetermined site of the subject by irradiating the predetermined site with light, radioactive rays such as X-rays, electromagnetic waves, or ultrasonic waves or the like, and an apparatus that obtains an image of a predetermined site by detecting radioactive rays emitted from the subject. More specifically, examples of an imaging apparatus according to the various examples and modifications described above include at least an X-ray imaging apparatus, a CT apparatus, an MRI apparatus, a PET apparatus, a SPECT apparatus, an SLO apparatus, an OCT apparatus, an OCTA apparatus, a fundus camera and an endoscope.

Note that, a time domain OCT (TD-OCT) apparatus and a Fourier domain OCT (FD-OCT) apparatus may be included as examples of an OCT apparatus. Further, examples of a Fourier domain OCT apparatus may include a spectral domain OCT (SD-OCT) apparatus and a swept source OCT (SS-OCT) apparatus. Further, an adaptive optics SLO (AO-SLO) apparatus and an adaptive optics OCT (AO-OCT) apparatus that use an adaptive optics system and the like may be included as examples of an SLO apparatus or an OCT apparatus, respectively. Furthermore, a polarization-sensitive SLO (PS-SLO) apparatus and a polarization-sensitive OCT (PS-OCT) apparatus and the like for visualizing information relating to polarization phase differences or depolarization may be included as examples of an SLO apparatus or an OCT apparatus, respectively.

Further, in the learned models for improving image quality according to the various examples and modifications described above, it is conceivable for the magnitude of intensity values of a tomographic image, and the order and slope, positions, distribution, and continuity of bright sections and dark sections and the like of a tomographic image to be extracted as a part of the feature values and used for estimation processing. Similarly, in the case of the learned models for segmentation processing, for image analysis, and for generating diagnosis results also, it is conceivable for the magnitude of intensity values of a tomographic image, and the order and slope, positions, distribution, and continuity of bright sections and dark sections and the like of a tomographic image to be extracted as a part of the feature values and used for estimation processing. On the other hand, in the case of the learned models for speech recognition, for character recognition, for gesture recognition and the like, since learning that uses time-series data is performed, it is conceivable to extract a slope between consecutive time-series data values that are input, as a part of the feature values, and to use the slope for estimation processing. Therefore, it is expected that such learned models can be utilized to perform estimation with excellent accuracy by using influences caused by changes over time in specific numerical values in estimation processing.

According to the embodiments and the modifications described above, an image that seems to be an image for which appropriate image processing has been performed for each region that is an observation target can be generated.

OTHER EXAMPLES

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

Examples of the processor or circuit may include a central processing unit (CPU), a microprocessing unit (MPU), a graphics processing unit (GPU), an application specific integrated circuit (ASIC), or a field programmable gateway (FPGA). Further, examples of the processor or circuit may include a digital signal processor (DSP), a data flow processor (DFP) or a neural processing unit (NPU).

The present invention is not limited to the embodiments and the modifications described above, and various changes and modifications can be made without departing from the spirit and scope of the present invention. Therefore, to apprise the public of the scope of the present invention, the following claims are appended.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. An image processing apparatus comprising at least one of (a) one or more processors connected to one or more memories storing a program including instructions executed by the one or more processors and (b) circuitry, each of (a) and (b) configured to function as:
   an obtaining unit configured to obtain a first tomographic image of an eye to be examined obtained by using optical coherence; and
   an image quality improving unit configured to generate, using the obtained first tomographic image as input data that is input into a learned model, a second tomographic image having a plurality of regions including a region of a retina and a region of a vitreous body with contrast higher than contrast of the plurality of regions in the obtained first tomographic image, the learned model being obtained by using training data including a third tomographic image of an eye to be examined obtained by using optical coherence that has at least one of a plurality of regions including a region of a retina and a region of a vitreous body and a fourth tomographic image that has the at least one of the plurality of regions with contrast higher than contrast of the at least one of the plurality of regions in the third tomographic image, and training data including a fifth tomographic image of an eye to be examined obtained by using optical coherence that has at least the other one of the plurality of regions and a sixth tomographic image that has at least the other one of the plurality of regions with contrast higher than contrast of at least the other one of the plurality of regions in the fifth tomographic image.

2. The image processing apparatus according to claim 1, the at least one of (a) and (b) further configured to function as:
   a selecting unit configured to select image processing to be applied to the first tomographic image according to an instruction from an operator;
   wherein, based on image processing that is selected by the selecting unit, the image quality improving unit performs gradation conversion processing without using the learned model with respect to the first tomographic image to generate a seventh tomographic image, or generates the second tomographic image from the first tomographic image using the learned model.

3. The image processing apparatus according to claim 1, wherein:
   in the second tomographic image, the image quality improving unit modifies pixel values of a connecting portion between a plurality of regions that are different to each other in the first tomographic image based on pixel values of pixels surrounding the connecting portion, or modifies pixel values of the surrounding pixels based on pixel values of the connecting portion.

4. The image processing apparatus according to claim 1, wherein:
   the plurality of regions further include a region of a choroid.

5. The image processing apparatus according to claim 1, wherein:
training data of the learned model includes a tomographic image obtained by subjecting a tomographic image obtained in an imaging mode corresponding to a region of a retina in a tomographic image which is obtained by imaging an eye to be examined to gradation conversion processing corresponding to a region of a vitreous body in the tomographic image-which is obtained by imaging an eye to be examined.

6. The image processing apparatus according to claim 1, wherein:
training data of the learned model includes a tomographic image obtained by subjecting a tomographic image obtained by using optical coherence to image processing for heightening contrast for each region; and
the image processing for heightening contrast is one kind of processing among averaging processing, maximum a posteriori processing, smoothing filter processing and gradation conversion processing.

7. The image processing apparatus according to claim 1, the at least one of (a) and (b) further configured to function as:
an analyzing unit configured to apply different analysis conditions to the respective plurality of regions in the second tomographic image; and
a display controlling unit configured to cause the second tomographic image and analysis results with respect to each of the plurality of regions that are obtained by the analyzing unit to be displayed on the display unit.

8. The image processing apparatus according to claim 1, the at least one of (a) and (b) further configured to function as:
a display controlling unit configured to control a display of a display unit;
wherein the display controlling unit causes information indicating that the second tomographic image is an image generated using the learned model to be displayed together with the second tomographic image on the display unit.

9. The image processing apparatus according to claim 1, wherein the image quality improving unit:
generates, from the first tomographic image, a label image in which different label values are given to the plurality of regions by using a learned model that is different from a learned model for generating the second tomographic image; and
generates the second tomographic image from the label image by using a learned model for generating the second tomographic image.

10. The image processing apparatus according to claim 1, the at least one of (a) and (b) further configured to function as:
an image processing unit configured to identify a plurality of regions in at least one image of the first tomographic image and the second tomographic image, wherein:
the image processing unit identifies the plurality of regions in the at least one image using the at least one image as input data that is input into a learned model that is different from a learned model for generating the second tomographic image.

11. The image processing apparatus according to claim 1, the at least one of (a) and (b) further configured to function as:
an image processing unit configured to identify a plurality of regions in at least one image of the first tomographic image and the second tomographic image; and
a drive controlling unit configured to, in a state in which the second tomographic image is displayed as a moving image, perform drive control of an optical member that changes an imaging range so that any of the identified plurality of regions is located at a predetermined position in a display region.

12. The image processing apparatus according to claim 1, the at least one of (a) and (b) further configured to function as:
an image processing unit configured to identify a plurality of regions in at least one image of the first tomographic image and the second tomographic image, wherein:
the image processing unit generates an image analysis result with respect to each of the identified plurality of regions or a diagnosis result with respect to each of the identified plurality of regions by using the at least one image as input data that is input into a learned model that is different from a learned model for generating the second tomographic image.

13. The image processing apparatus according to claim 1, the at least one of (a) and (b) further configured to function as:
an image processing unit configured to identify a plurality of regions in at least one image of the first tomographic image and the second tomographic image, wherein:
the image processing unit generates, as information relating to an abnormal site, information relating to a difference between a tomographic image obtained using a generative adversarial network or an auto-encoder with respect to each of the identified plurality of regions, and the tomographic image input to the generative adversarial network or the auto-encoder.

14. The image processing apparatus according to claim 1, the at least one of (a) and (b) further configured to function as:
An image processing unit configured to identify a plurality of regions in at least one image of the first tomographic image and the second tomographic image, wherein:
the image processing unit performs a search for a similar case image with respect to each of the identified plurality of regions by using the at least one image as input data that is input into a learned model that is different from a learned model for generating the second tomographic image.

15. The image processing apparatus according to claim 1, wherein:
the first tomographic image and the second tomographic image are three-dimensional OCT tomographic images; and
the at least one of (a) and (b) is further configured to function as a generating unit configured to generate an en-face image corresponding to a partial depth range of the second tomographic image.

16. An image processing method comprising:
obtaining a first tomographic image of an eye to be examined obtained by using optical coherence; and
generating, using the obtained first tomographic image as input data that is input into a learned model, a second tomographic image having a plurality of regions including a region of a retina and a region of a vitreous body with contrast higher than contrast of the plurality of regions in the obtained first tomographic image, the learned model being obtained by using training data including a third tomographic image of an eye to be examined obtained by using optical coherence that has at least one of a plurality of regions including a region of a retina and a region of a vitreous body and a fourth tomographic image has the at least one of the plurality of regions with contrast higher than contrast of the at least one of the plurality of regions in the third tomographic image, and training data including a fifth tomographic image of an eye to be examined obtained by using optical coherence that has at least the other one of the plurality of regions and a sixth tomographic image that has at least the other one of the plurality of regions with contrast higher than contrast of at least the other one of the plurality of regions in the fifth tomographic image.

17. A non-transitory computer-readable medium having stored thereon a program that, upon being executed by a processor, causes the processor to execute each process of the image processing method according to claim 16.

18. The image processing apparatus according to claim 4, wherein:
- the training data includes:
    - training data including a partial image that includes a region of one of a vitreous body and a choroid in a tomographic image of an eye to be examined obtained in an imaging mode corresponding to the one, as input data, and a partial image that includes a region of the one in a tomographic image obtained by subjecting the tomographic image obtained in the imaging mode to image processing for heightening contrast of the region of the one, as correct answer data;
    - training data including a partial image that includes a region of one of a vitreous body and a choroid in a tomographic image of an eye to be examined obtained in an imaging mode corresponding to the other one of the vitreous body and the choroid, as input data, and an image that is obtained by vertically inverting a partial image including a region of the one in a tomographic image obtained by subjecting a tomographic image of an eye to be examined obtained in an imaging mode corresponding to the one to image processing for heightening contrast of the region of the one, as correct answer data; and
    - training data including a partial image that includes a region of retina in a tomographic image of an eye to be examined obtained in an imaging mode corresponding to one of a vitreous body and a choroid, as input data, and a partial image that includes a region of a retina in a tomographic image obtained by subjecting the tomographic image obtained in the imaging mode to image processing for heightening contrast of the region of the retina, as correct answer data, or an image that is obtained by vertically inverting a partial image including a region of a retina in a tomographic image obtained by subjecting a tomographic image of an eye to be examined obtained in an imaging mode corresponding to the other one of the vitreous body and the choroid to image processing for heightening contrast of the region of the retina, as correct answer data.

19. The image processing apparatus according to claim 1, wherein:
- the third tomographic image and the fourth tomographic image have the one of the plurality of regions and do not have the other one of the plurality of regions, and the fifth tomographic image and the sixth tomographic image have the other one of the plurality of regions and does not have the one of the plurality of regions.

* * * * *